(12) United States Patent
Ohlmann et al.

(10) Patent No.: US 12,049,480 B2
(45) Date of Patent: *Jul. 30, 2024

(54) METHODS AND PRODUCTS FOR GENETIC ENGINEERING

(71) Applicants: Institut National de la Sante et de la Recherche Medicale (INSERM), Paris (FR); Centre National de la Recherche Scientifique (CNRS), Paris (FR); Ecole Normale Superieure de Lyon, Lyons (FR); Universite Claude Bernard Lyon 1, Villeurbanne (FR)

(72) Inventors: Théophile Ohlmann, Tassin la Demi-Lune (FR); Philippe Mangeot, Lyons (FR); Emiliano Ricci, Lyons (FR)

(73) Assignees: Institut National De La Sante Et De La Recherche Medicale (INSERM) Paris, FRANCE; Ecole Normale Superieure de Lyon Lyon (FR); Centre National De La Recherche Scientifique (CNRS) Paris, FRANCE; Universite Claude Bernard Lyon 1 Villeurbanne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/518,304

(22) Filed: Nov. 22, 2023

(65) Prior Publication Data

US 2024/0109940 A1    Apr. 4, 2024

Related U.S. Application Data

(63) Continuation of application No. 18/130,375, filed on Apr. 3, 2023, which is a continuation of application No. 17/174,405, filed on Feb. 12, 2021, now Pat. No. 11,649,264, which is a continuation of application No. 15/769,534, filed as application No. PCT/EP2016/075289 on Oct. 20, 2016, now Pat. No. 10,968,253.

(30) Foreign Application Priority Data

Oct. 20, 2015  (EP) .................................. 15306678

(51) Int. Cl.
| | | |
|---|---|---|
| *C07K 14/005* | (2006.01) | |
| *C12N 7/00* | (2006.01) | |
| *C12N 9/22* | (2006.01) | |
| *C12N 15/10* | (2006.01) | |
| *C12N 15/113* | (2010.01) | |

(52) U.S. Cl.
CPC .............. *C07K 14/005* (2013.01); *C12N 7/00* (2013.01); *C12N 9/22* (2013.01); *C12N 15/102* (2013.01); *C12N 15/113* (2013.01); *C07K 2319/00* (2013.01); *C07K 2319/43* (2013.01); *C07K 2319/50* (2013.01); *C12N 2310/20* (2017.05); *C12N 2740/10023* (2013.01); *C12N 2740/10042* (2013.01); *C12N 2740/13023* (2013.01); *C12N 2740/13042* (2013.01); *C12N 2800/80* (2013.01)

(58) Field of Classification Search
CPC .............. C07K 14/005; C07K 2319/00; C07K 2319/43; C07K 2319/50; C12N 7/00; C12N 15/102; C12N 15/113; C12N 9/22; C12N 2310/20; C12N 2800/80; C12N 2740/10023; C12N 2740/13023; C12N 2740/13042; C12N 2740/10042; C12N 15/90

See application file for complete search history.

(56) References Cited

U.S. PATENT DOCUMENTS

| | | | |
|---|---|---|---|
| 6,060,064 A | 5/2000 | Elizabeth et al. | |
| 6,204,059 B1 | 3/2001 | Samulski et al. | |
| 10,968,253 B2 | 4/2021 | Ohlmann et al. | |
| 11,649,264 B2 | 5/2023 | Ohlmann et al. | |
| 2011/0189159 A1 | 8/2011 | Chatterjee et al. | |
| 2011/0262483 A1 | 10/2011 | Haynes et al. | |
| 2012/0269840 A1 | 10/2012 | Barnett et al. | |
| 2016/0074427 A1 | 3/2016 | Kishimoto et al. | |
| 2016/0340661 A1 | 11/2016 | Cong et al. | |
| 2016/0367702 A1 | 12/2016 | Hoge et al. | |
| 2019/0010518 A1 | 1/2019 | Quake et al. | |
| 2024/0132547 A1 | 4/2024 | Ohlmann et al. | |

FOREIGN PATENT DOCUMENTS

| | | |
|---|---|---|
| WO | WO 1992/012237 | 7/1992 |
| WO | WO 1995/022617 | 8/1995 |
| WO | WO 2013/068847 | 5/2013 |
| WO | WO 2013/163628 | 10/2013 |
| WO | WO 2013/176772 | 11/2013 |
| WO | WO 2014/093595 | 6/2014 |
| WO | WO 2014/131833 | 9/2014 |
| WO | WO 2014/200659 | 12/2014 |

(Continued)

OTHER PUBLICATIONS

Abe et al., "In vitro cell-free conversion of noninfectious moloney retrovirus particles to an infectious form by the addition of the vesicular stomatitis virus surrogate envelope G protein," J. Virol. 72(8):6356-6361 (1998) XP00913189C.

(Continued)

*Primary Examiner* — Rachel B Gill
(74) *Attorney, Agent, or Firm* — Morrison & Foerster LLP

(57) ABSTRACT

The present invention relates to a virus-derived particle comprising one or more Cas protein(s), as well as to kits and methods using the same for altering a target nucleic acid.

16 Claims, 25 Drawing Sheets

Specification includes a Sequence Listing.

(56) References Cited

FOREIGN PATENT DOCUMENTS

| WO | WO 2015/089247 | 6/2015 |
|---|---|---|
| WO | WO 2015/089486 | 6/2015 |
| WO | WO 2016/073433 | 5/2016 |
| WO | WO 2017/001570 | 1/2017 |
| WO | WO 2017/106822 | 6/2017 |

OTHER PUBLICATIONS

Aliyari et al., "RNA-based viral immunity initiated by the Dicer family of host immune receptors," Immunol Rev. (2009) 227(1):176-88.
Anastasov et al., Lentiviral vectors and exosomes as gene and protein delivery tools, in Methods in Molecular Biology, (2016) 1448: 49-61.
Aoki et al., "Protein transduction by pseudotyped lentivirus-like nanoparticles," Gene Therapy (2011) 1-6.
Brandler et al. "Recombinant vector derived from live attenuated measles virus: potential for flavivirus vaccines," Comp Immunol Microbiol Infect Dis. (2008) 31(No. 2-3): 271-291.
Brown et al., "Assembly of hybrid bacteriophage Qbeta virus-like particles," Biochemistry. (2009) 48(47):11155-11157.
Cai et al., "Targeted genome editing by lentiviral protein transduction of ZFN and Cas9 proteins," Selected oral presentation (2014) A31:OR021.
Cai et al., "Targeted genome editing by lentiviral protein transduction of zinc-finger and TAL-effector nucleases." (2014) Elife sciences publications Ltd. 3: 1-19.
Cass et al., "The role of Cas8 in type I CRISPR interference," Biosci Rep. (2015) 5;35(3):e00197. (doi:10.1042/BSR20150043).
Cervera et al., "Generation of HIV-1 Gag VLPs by transient transfection of HEK 293 suspension cell cultures using an optimized animal-derived component free medium," J Biotechnol. (2013) 166(4): 152-65.
Choi JG, Dang Y, Abraham S, Ma H, Zhang J, Guo H, Cai Y, Mikkelsen JG, Wu H, Shankar P, Manjunath N. Lentivirus prepacked with Cas9 protein for safer gene editing. Gene Ther. Jul. 2016 ;23(7) :627-33. doi: 10.1038/gt.2016.27. Epub Apr. 7, 2016.
Chylinski et al. "The tracrRNA and Cas9 families of type II CRISPR-Cas immunity systems," RNA Biol. May 1, 2013; 10(5): 726-737.
Chylinski et al., "Classification and evolution of type II CRISPR-Cas systems," Nucleic Acids Res. (2014) 42(10):6091-105.
Cong et al., "Multiplex Genome Engineering Using CRISPR/Cas Systems," Science (2013) 339(6121): 819-823.
Cronin et al., "Altering the tropism of lentiviral vectors through pseudotyping," Curr Gene Ther. (2005) 5(4):387-98.
Dale et al.: "Tracking and quantitation of fluorescent HIV during cell-cell transmission", Methods. Jan. 2011; 53(1): 20-26. doi:10.1016/j.ymeth.2010.06.018.
DiCarlo et al., "Genome engineering in *Saccharomyces cerevisiae* using CRISPR-Cas systems," Nucleic Acids Res. (2013) 41(7):4336-43.
Esvelt et al., "Orthogonal Cas9 proteins for RNA-guided gene regulation and editing," Nat Methods. (2013) 10(11):1116-21. doi: 10.1038/nmeth.2681.
Fabre et al., "CRISPR is an optimal target for the design of specific PCR assays for *Salmonella enterica* serotypes Typhi and Paratyphi A," PLoS Negl Trop Dis. (2014) 8(1):e2671.
Farboud et al. "Dramatic Enhancement of Genome Editing by CRISPR/Cas9 Through Improved Guide RNA Design," Genetics, (2015) 199(4); 959-971, (doi 10.1534/genetics.115.175166).
Fenard et al., "Vectofusin-1, a new viral entry enhancer, strongly promotes lentiviral transduction of human hematopoietic stem cells," Mol Ther Nucleic Acids. May 7, 2013;2(5):e90.
Fontana et al., "Rabies virus-like particles expressed in HEK293 cells," Vaccine. (2014) 32(24); 2799-804.

Fu A, Tang R, Hardie J, Farkas ME, Rotella VM. Promises and pitfalls of intracellular delivery of proteins. Bioconjug Chem. Sep. 17, 2014;25(9):1602-8. Epub Sep. 2, 2014.
Garrone et al.: "A prime-boost Strategy Using Virus-Like Particles Pseudotyped for HGV Proteins Triggers Broadly Neutralizing Antibodies in Macaques", Science Translation Medicine. Aug. 3, 2011. vol. 3 Issue.
Gasiunas et al., "Cas9-crRNA ribonucleoprotein complex mediates specific DNA cleavage for adaptive immunity in bacteria," Proc Natl Acad Sci USA. (2012) 109(39):E2579-86.
Girard-Gagnepain et al., "Baboon envelope pseudotyped LVs outperform VSV-G-LVs for gene transfer into early-cytokine-stimulated and resting HSCs," Blood.(2014) 124 (8):1221-1231.
Gong et al., "Mechanism of nonhomologous end-joining in mycobacteria: a low-fidelity repair system driven by Ku, ligase D and ligase C," Nat Struct Mol Biol. (2005) 12(4):304-12.
Gori JL, Hsu PD, Maeder ML, Shen S, Welstead GG, Bumcrot D. Delivery and Specificity of CRISPR-Cas9 Genome Editing Technologies for Human Gene Therapy. Hum Gene Ther. Jul. 2015;26(7):443-51.
Gratz et al., "Highly specific and efficient CRISPR/Cas9-catalyzed homology-directed repair in *Drosophila*," Genetics. (2014) 196(4):961-71. doi:10.1534/genetics.113.160713.
Guibingua et al., "Cell surface heparan sulfate is a receptor for attachment of envelope protein-free retrovirus-like particles and VSV-G pseudotyped MLV-derived retrovirus vectors to target cells," Mol Ther. (2002) 5(5 Pt 1):538-46.
Guo et al., Efficient RNA/Cas9-mediated genome editing in Xenopus tropicalis, 2014, Development. (2014) 141(3):707-14.
Hackett et al., Delivering the second revolution in seite-specififc nucleases, Elife 2014 e02904.
Hai et al., "One-step generation of knockout pigs by zygote injection of CRISPR/Cas system," (2014) Cell Res. 24: 372-375. doi: 10.1038/cr.2014.11.
Heler et al., "Cas9 specifies functional viral targets during CRISPR-Cas adaptation," Nature. (2015) 519(7542): 199-202.
Herbst-Kralovetz et al., "Norwalk virus-like particles as vaccines," Expert Rev Vaccines. (2010) 9(3): 299-307.
Hill BD, Zak A, Khera E, Wen F. Engineering Virus-like Particles for Antigen and Drug Delivery. Curr Protein Pept Sci. 2018;19(1): 112-127.
Hochstrasser et al., "CasA mediates Cas3-catalyzed target degradation during CRISPR RNA-guided interference," PNAS (2014) 111(18):6618-6623.
Hong et al.,"Novel recombinant hepatitis B virus vectors efficiently deliver protein and RNA encoding genes into primary hepatocytes," J Virol. (2013) 87(12):6615-24.
Horii et al: "Efficient generation of knockin mice by CRISPR/Cas system", Experimental Animals vol. 64, abstract, 2015.
Hwang et al., "Heritable and precise zebrafish genome editing using a CRISPR-Cas system," PLoS One. (2013) 8(7):e68708.
Jalaguier et al., "Efficient production of HIV-1 virus-like particles from a mammalian expression vector requires the N-terminal capsid domain," PLoS One. (2011) 6(11):e28314.
Jao et al., "Efficient multiplex biallelic zebrafish genome editing using a CRISPR nuclease system," Proc Natl Acad Sci U S A. (2013) 110(34):13904-13909.
Jinek et al., "A Programmable Dual-RNA-Guided DNA Endonuclease in Adaptive Bacterial Immunity," Science. (2012) 337(6096) :816-21.
Jinek et al., "RNA-programmed genome editing in human cells," Elife. (2013) 2:e00471. doi: 10.7554/eLife.00471.
Johnston et al., "High-throughput screening identifies compounds that enhance lentiviral transduction," Gene Ther. (2014) 21(12): 1008-20.
Kabadi et al., "Multiplex CRISPR/Cas9-based genome engineering from a single lentiviral vector," Nucleic Acids Res. (2014) 42(19):e147.
Kaczmarczyk SJ, Sitaraman K, Young HA, Hughes SH, Chatterjee DK. Protein delivery using engineered virus-like particles. Proc Natl Acad Sci U SA. Oct. 11, 2011; 108(41): 16998-7003. Epub Sep. 26, 2011.

(56) References Cited

OTHER PUBLICATIONS

Kajigaya et al., "Self-assembled B19 parvovirus capsids, produced in a baculovirus system, are antigenically and immunogenically similar to native virions," Proc Natl Acad Sci USA. (1991) 88(11):4646-50.
Kang et al., "Chimeric rabies virus-like particles containing membrane-anchored GM-CSF enhances the immune response against rabies virus," Viruses. (2015) 7(3): 1134-52. doi: 10.3390/v7031134.
Kieusseian et al., "Expression of Pitx2 in stromal cells is required for normal hematopoiesis," Blood. (2006) 107(2):492-500.
Kim et al., "Highly efficient Genome RNA-guided Research, genome vol. 24, editing pages in human 1012-1019, cells via 2014 delivery of purified Cas9 ribonucleoproteins," Genome Research (2014) 24:1012-1019.
Kirnbauer et al., "Virus-like particles of bovine papillomavirus type 4 in prophylactic and therapeutic immunization," Virology. (1996) 219(1):37-44.
Kushnir et al., "Virus-like particles as a highly efficient vaccine platform: diversity of targets and production systems and advances in clinical development," Vaccine. (2012) 31(1):58-83.
Lafountaine Justin S et al: "Delivery and therapeutic applications of gene editing technologies ZFNs, TALENs, and CRISPR/Cas9", International Journal of Pharmaceutics, vol. 494, No. 1, 2015 (Aug. 13, 2015.
Latham et al., "Formation of wild-type and chimeric influenza virus-like particles following simultaneous expression of only four structural proteins," J Virol. (2001) 75(13):6154-65.
Li et al., "Expression and self-assembly of empty virus-like particles of hepatitis E virus," J Virol. (1997) 71(10):7207-13.
Lin et al., "Enhanced homology-directed human genome engineering by controlled timing of CRISPR/Cas9 delivery," Elife. (2014) 15;3:e04766.
Lombardo et al., "TLR4-mediated survival of macrophages is MyD88 dependent and requires TNF-alpha autocrine signalling," J Immunol. (2007) 178(6): 3731-3739.
Ludwig et al., "Virus-like particles-universal molecular toolboxes," Curr Opin Biotechnol. (2007) 18(6):537-45.
Ma et al., "A guide RNA sequence design platform for the CRISPR/Cas9 system for model organism genomes," Biomed Res Int. (2013) ;2013:270805. doi: 10.1155/2013/270805.
Ma et al., "Generating rats with conditional alleles using CRISPR/Cas9," Cell Res. (2014) 24(1):122-5.
Maeder et al., "CRISPR RNA-guided activation of endogenous human genes," Nat Methods. (2013) 10(10):977-9.
Maetzig et al., "Retroviral protein transfer: falling apart to make an impact," Curr Gene Ther. (2012) 12(5):389-409.
Makarova et al., "Unification of Cas protein families and a simple scenario for the origin and evolution of CRISPR-Cas systems," Biol Direct. 2011; 6: 38.
Mali et al., "RNA-guided human genome engineering via Cas9," Science. (2013) 339(6121): 823-826.
Mangeot et al. (2011, Mol Ther J Am Soc Gene Ther, vol. 19: 1656-1666.
Mangeot et al., "A universal transgene silencing method based on RNA interference," Nucleic Acids Res. (2004) 32(12):e102.
Mangeot et al., "Development of minimal lentivirus vectors derived from simian immunodeficiency virus (SIVmac251) and their use for gene transfer into human dendritic cells," J Virol. (2000) 74(18): 8307-8315.
Markowitz et al., "A safe packaging line for gene transfer: separating viral genes on two different plasmids," J. Virol. (1988) 62(4): 1120.
Mashiko et al., "Feasibility for a large scale mouse mutagenesis by injecting CRISPR/Cas plasmid into zygotes," Dev Growth Differ. (2014) 56(1):122-9.
Mateu MG. Assembly, Engineering and Applications of Virus-Based Protein Nanoparticles. Adv Exp Med Biol. 2016;940:83-120. Review. PubMed PMID: 27677510.

Mselli-Lakhal et al., "Gene transfer system derived from the caprine arthritis-encephalitis lentivirus," J Virol Methods. (2006) 136(1-2):177-184.
Murawski et al., "Newcastle disease virus-like particles containing respiratory syncytial virus G protein induced protection in BALB/c mice, with no evidence of immunopathology," J Virol. (2010) 84(2):1110-23.
Naskalska et al., "Virus Like Particles as Immunogens and Universal Nanocarriers," Pol J Microbiol. (2015) 64(1): 3-13.
Negre et al., "Characterization of novel safe lentiviral vectors derived from simian immunodeficiency virus (SIVmac251) that efficiently transduce mature human dendritic cells," (2000) Gene Ther. 7(19): 1613-1623.
Niu et al., "Generation of gene-modified cynomolgus monkey via Cas9/RNA-mediated gene targeting in one-cell embryos," Cell. (2014) 156(4): 836-43.
O'Connell et al., "Programmable RNA recognition and cleavage by CRISPR/Cas9," Nature. (2014) 516(7530): 263-266.
Ogasawara et al., "Recombinant viral-like particles of parvovirus B19 as antigen carriers of anthrax protective antigen," In Vivo. (2006) 20(3): 319-24.
Oji et al: "Complex genome editing in mouse ES cells using the CRISPR/Cas system", Experimental Animals.
Okimoto et al., "VSV-G envelope glycoprotein forms complexes with plasmid DNA and MLV retrovirus-like particles in cell-free conditions and enhances DNA transfection," Mol Ther. (2001) 4(3): 232-8.
Olsen, "Gene transfer vectors derived from equine infectious anemia virus," Gene Ther. (1998) 5(11):1481-1487.
Overballe-Petersen et al., "Bacterial natural transformation by highly fragmented and damaged DNA," Proc Natl Acad Sci USA. (2013) 110(49):19860-19865.
Peifang et al., "Enhanced activation of human T cell clones specific for virus-like particles expressing the HIV V3 loop in the presence of HIV V3 loop-specific polyclonal antibodies," Clin Exp Immunol. (1994) 97(3): 361-6.
Qazi et al: "Programmed Self-Assembly of an Active P22-Cas9 Nanocarrier System", Molecular Pharmaceutics, vol. 13, No. 3, Mar. 7, 2016 (Mar. 7, 2016), pp. 1191-1196, XP055268807.
Qi et al., "Repurposing CRISPR as an RNA-guided platform for sequence-specific control of gene expression," Cell. (2013) 152(5): 1173-83.
Quan et al., "Influenza M1 VLPs containing neuraminidase induce heterosubtypic cross-protection," Virology. (2012) 430(2): 127-35.
Ramakrishna et al: "Gene disruption by cell-penetrating peptide-mediated delivery of Cas9 protein and guide RNA", Genome Research, vol. 24, pp. 1020-1027, Apr. 2, 2014.
Ran et al., "Double nicking by RNA-guided CRISPR Cas9 for enhanced genome editing specificity," Cell. (2013) 154(6): 1380-9.
Rasmussen et al., "Characterization of virus-like particles produced by a recombinant baculovirus containing the gag gene of the bovine immunodeficiency-like virus," Virology. (1990) 178(2): 435-51.
Rohovie MJ, Nagasawa M, Swartz JR. Virus-like particles: Next-generation nanoparticles for targeted therapeutic delivery. Bioeng Transl Med. Jan. 19, 2017;2(1):43-57.
Ruffing et al., "Assembly of viruslike particles by recombinant structural proteins of adeno-associated virus type 2 in insect cells," J Virol. (1992) 66(12):6922-6930.
Saenz et al., "Feline immunodeficiency virus-based lentiviral vectors," Cold Spring Harb Protoc. (2012) 2012(1):71-6.
Saenz et al., "Production and harvest of feline immunodeficiency virus-based lentiviral vector from cells grown in T75 tissue-culture flasks," Cold Spring Harb Protoc. (2012) 2012(1):124-125.
Saenz et al., "Production, harvest, and concentration of feline immunodeficiency virus-based lentiviral vector from cells grown in CF10 or CF2 devices," Cold Spring Harb Protoc. (2012) 2012(1): 118-23.
Sakuma et al., Multiplex genome engineering in human cells using all in one CRISPR/Cas9 vector system. Sci Rep. 4: 5400, 2014.
Samulski et al., "Helper-free stocks of recombinant adeno-associated viruses: normal integration does not require viral gene expression," J Virol. (1989) 63(9): 3822-8.

(56) References Cited

OTHER PUBLICATIONS

Sanjana et al., "Improved vectors and genome-wide libraries for CRISPR screening," Nat Methods. (2014) 11(8):783-784.

Shalem et al., "Genome-scale CRISPR-Cas9 knockout screening in human cells," Science. (2014) 343(6166): 84-87.

Sharma et al., "Noninfectious virus-like particles produced by Moloney murine leukemia virus-based retrovirus packaging cells deficient in viral envelope become infectious in the presence of lipofection reagents," Proc Natl Acad Sci USA. (1997) 94(20): 10803-10808.

Sinkunas et al., "Cas3 is a single-stranded DNA nuclease and ATP-dependent helicase in the CRISPR/Cas immune system," EMBO J. (2011) 30(7):1335-42.

Skipper et al., "Delivering the goods for genome engineering and editing." Hum Gene Therapy. (2015) 26(8):486-497.

Sun et al.: 11 Self-Assembled DNA Nanoclews for the Efficient Delivery of CRISPR-Cas9 for Genome Editing11 , Angewandte Chemie International Edition, vol. 54, No. 41, Oct. 5, 2015 (Oct. 5, 2015).

Takahara et al., "A new retrovirus packaging cell for gene transfer constructed from amplified long terminal repeat-free chimeric proviral genes," J Virol. (1992) 66(6): 3725-3732.

Tomé-Amat et al., "Secreted production of assembled Norovirus virus-like particles from Pichia pastoris," Microb Cell Fact. (2014) 13:134-142.

Voelkel C, Galla M, Maetzig T, Warlich E, Kuehle J, Zychlinski D, Bode J, Cantz T, Schambach A, Baum C. Protein transduction from retroviral Gag precursors. Proc Natl Acad Sci U SA. Apr. 27, 2010; 107(17):7805-10. doi: 10. 1073/pnas.0914517107. Epub Apr. 12, 2010.

Wagner et al., "Transfer of genes into embryonal carcinoma cells by retrovirus infection: efficient expression from an internal promoter," EMBO J. (1985) 4(3):663-6.

Walpita et al., "Mammalian Cell-Derived Respiratory Syncytial Virus-Like Particles Protect the Lower as well as the Upper Respiratory Tract," PLoS One. (2015) 10(7): e0130755.

Wang et al., "One-step generation of mice carrying mutations in multiple genes by CRISPR/Cas-mediated genome engineering," Cell. (2013) 153(4):910-918.

Wang et al., "Virus-like particles for the prevention of human papillomavirus-associated malignancies," Expert Rev Vaccines. (2013) 12(2):129-41.

Yang et al., "Effective gene targeting in rabbits using RNA-guided Cas9 nucleases," J Mol Cell Biol. (2014) 6(1):97-99.

Yang et al., "HIV-1 virus-like particles produced by stably transfected *Drosophila* S2 cells: a desirable vaccine component," J Virol. (2012) 86(14):7662-7676.

Yee et al., "A general method for the generation of high-titer, pantropic retroviral vectors: highly efficient infection of primary hepatocytes," Proc Natl Acad Sci USA. (1994) 91(20):9564-9568.

Yee et al., "Generation of high-titer pseudotyped retroviral vectors with very broad host range," Methods Cell Biol. (1994);43 Pt A: 99-112.

Zeltins, Andris. "Construction and characterization of virus-like particles: a review." Mol Biotechnol. (2013) 53(1): 92-107.

Zetsche et al., "Cpf1 is a single RNA-guided endonuclease of a class 2 CRISPR-Cas system," Cell. (2015) 163(3):759-71. http://dx.doi.org/10.1016/j.cell.2015.09.038.

Zhao et al., "BPV1 E2 protein enhances packaging of full-length plasmid DNA in BPV1 pseudovirions," Virology. (2000) 272(2): 382-93.

Zhu et al., "CRISPRseek: a bioconductor package to identify target-specific guide RNAs for CRISPR-Cas9 genome-editing systems," PLoS One. (2014) 9(9):e108424.

Zuris et al., "Efficient delivery of genome-editing proteins in vitro and in vivo," Nat Biotechnol (2015) 33(1):73-80.

Zuris, John A., et al. "Cationic lipid-mediated delivery of proteins enables efficient protein-based genome editing in vitro and in vivo." Nature biotechnology 33.1 (2015): 73-80.

Mazurov et al., "Packaging and Uncoating of CRISPR/Cas Ribonucleoproteins for Efficient Gene Editing with Viral and Non-Viral Extracellular Nanoparticles," Viruses. (2023) 15(3):690 (23 pages).

Shalem et al., "Genome-scale CRISPR-Cas9 knockout screening in human cells," Science. (2014) 343(6166): 84-87. Supplementary Information (78 pages).

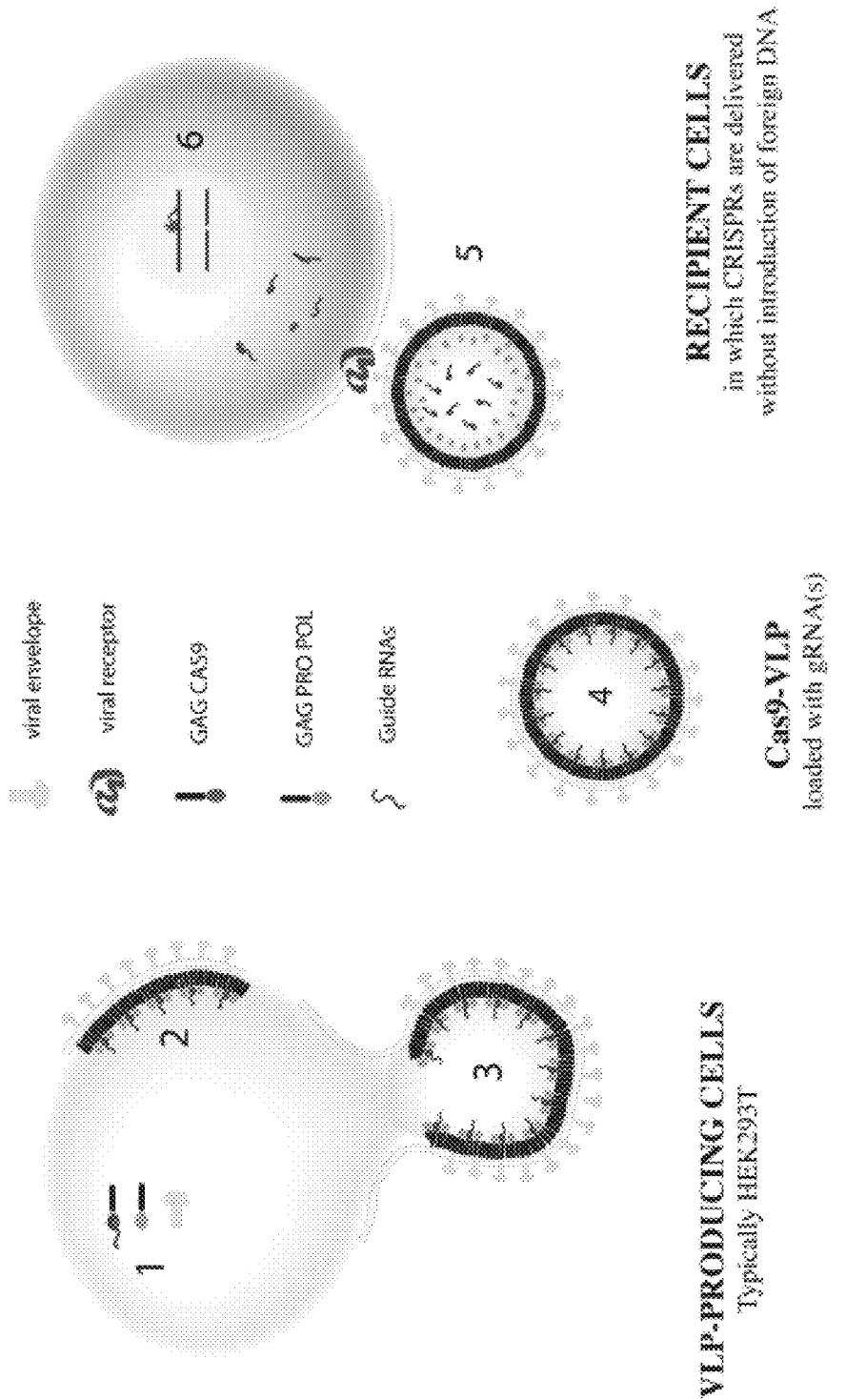

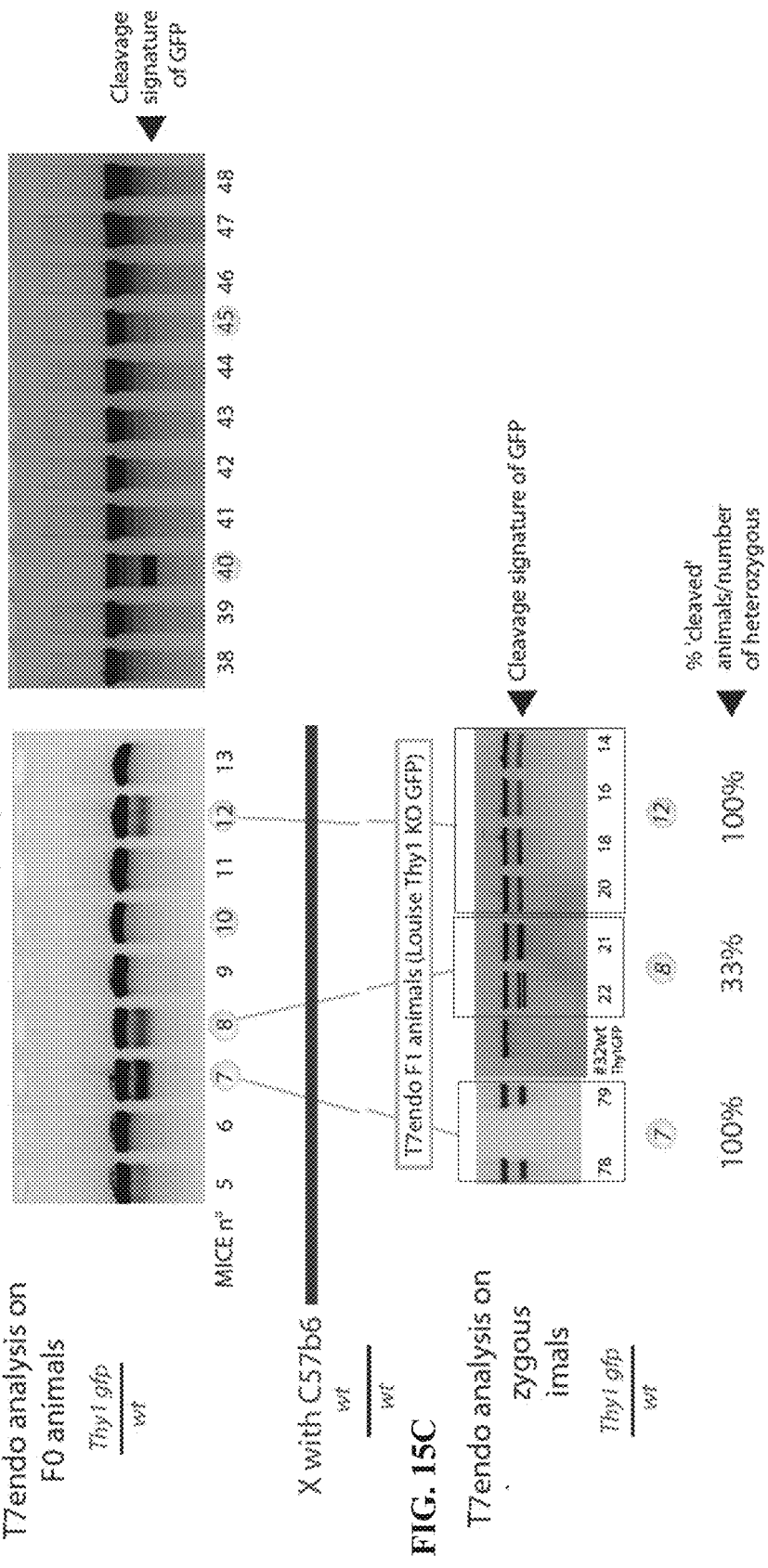

SEQUENCE LISTING

```
Sequence total quantity: 40
SEQ ID NO: 1              moltype = DNA  length = 25
FEATURE                   Location/Qualifiers
misc_feature              1..25
                          note = Synthetic YFPgRNA1f primer
misc_feature              1..25
                          note = YFPgRNA1f primer
source                    1..25
                          mol_type = other DNA
                          organism = synthetic construct
SEQUENCE: 1
caccgcgagg agctgttcac cgggg                                        25

SEQ ID NO: 2              moltype = DNA  length = 25
FEATURE                   Location/Qualifiers
misc_feature              1..25
                          note = Synthetic YFPgRNA1r primer
misc_feature              1..25
                          note = YFPgRNA1r primer
source                    1..25
                          mol_type = other DNA
                          organism = synthetic construct
SEQUENCE: 2
aaacccccgg tgaacagctc ctcgc                                        25

SEQ ID NO: 3              moltype = DNA  length = 25
FEATURE                   Location/Qualifiers
misc_feature              1..25
                          note = Synthetic YFPgRNA2f primer
misc_feature              1..25
                          note = YFPgRNA2f primer
source                    1..25
                          mol_type = other DNA
                          organism = synthetic construct
SEQUENCE: 3
caccgtcacc ataccggtag ccagc                                        25

SEQ ID NO: 4              moltype = DNA  length = 25
FEATURE                   Location/Qualifiers
misc_feature              1..25
                          note = Synthetic YFPgRNA2r primer
misc_feature              1..25
                          note = YFPgRNA2r primer
source                    1..25
                          mol_type = other DNA
                          organism = synthetic construct
```

```
SEQUENCE: 4
aaacgctggc taccggtatg gtgac                                              25

SEQ ID NO: 5             moltype = DNA   length = 25
FEATURE                  Location/Qualifiers
misc_feature             1..25
                         note = Synthetic hMyd88gRNA1f primer
misc_feature             1..25
                         note = hMyd88gRNA1f primer
source                   1..25
                         mol_type = other DNA
                         organism = synthetic construct
SEQUENCE: 5
caccggagac ctcaagggta gaggt                                              25

SEQ ID NO: 6             moltype = DNA   length = 25
FEATURE                  Location/Qualifiers
misc_feature             1..25
                         note = Synthetic hMyd88gRNA1r primer
misc_feature             1..25
                         note = hMyd88gRNA1r primer
source                   1..25
                         mol_type = other DNA
                         organism = synthetic construct
SEQUENCE: 6
aaacacctct acccttgagg tctcc                                              25

SEQ ID NO: 7             moltype = DNA   length = 25
FEATURE                  Location/Qualifiers
misc_feature             1..25
                         note = Synthetic hMyd88gRNA2f primer
misc_feature             1..25
                         note = hMyd88gRNA2f primer
source                   1..25
                         mol_type = other DNA
                         organism = synthetic construct
SEQUENCE: 7
caccggcagc catggcgggc ggtcc                                              25

SEQ ID NO: 8             moltype = DNA   length = 25
FEATURE                  Location/Qualifiers
misc_feature             1..25
                         note = Synthetic hMyd88gRNA2r primer
misc_feature             1..25
                         note = hMyd88gRNA2r primer
source                   1..25
                         mol_type = other DNA
                         organism = synthetic construct
SEQUENCE: 8
aaacggaccg cccgccatgg ctgcc                                              25

SEQ ID NO: 9             moltype = DNA   length = 25
FEATURE                  Location/Qualifiers
misc_feature             1..25
                         note = Synthetic mMyd88gRNA1f primer
misc_feature             1..25
                         note = mMyd88gRNA1f primer
source                   1..25
                         mol_type = other DNA
                         organism = synthetic construct
SEQUENCE: 9
caccggagcg tactggacgg caccg                                              25

SEQ ID NO: 10            moltype = DNA   length = 25
FEATURE                  Location/Qualifiers
misc_feature             1..25
                         note = Synthetic mMyd88gRNA1r primer
misc_feature             1..25
                         note = mMyd88gRNA1r primer
source                   1..25
                         mol_type = other DNA
                         organism = synthetic construct
SEQUENCE: 10
aaaccggtgc cgtccagtac gctcc                                              25

SEQ ID NO: 11            moltype = DNA   length = 25
FEATURE                  Location/Qualifiers
misc_feature             1..25
                         note = Synthetic mMyd88gRNA2f primer
```

```
misc_feature           1..25
                       note = mMyd88gRNA2f primer
source                 1..25
                       mol_type = other DNA
                       organism = synthetic construct
SEQUENCE: 11
caccggccca tctcctccgc cagca                                             25

SEQ ID NO: 12          moltype = DNA  length = 25
FEATURE                Location/Qualifiers
misc_feature           1..25
                       note = Synthetic mMyd88gRNA2r primer
misc_feature           1..25
                       note = mMyd88gRNA2r primer
source                 1..25
                       mol_type = other DNA
                       organism = synthetic construct
SEQUENCE: 12
aaactgctgg cggaggagat gggcc                                             25

SEQ ID NO: 13          moltype = DNA  length = 25
FEATURE                Location/Qualifiers
misc_feature           1..25
                       note = Synthetic DDX3gRNA1f primer
misc_feature           1..25
                       note = DDX3gRNA1f primer
source                 1..25
                       mol_type = other DNA
                       organism = synthetic construct
SEQUENCE: 13
caccgaggga tgagtcatgt ggcag                                             25

SEQ ID NO: 14          moltype = DNA  length = 25
FEATURE                Location/Qualifiers
misc_feature           1..25
                       note = Synthetic DDX3gRNA1r primer
misc_feature           1..25
                       note = DDX3gRNA1r primer
source                 1..25
                       mol_type = other DNA
                       organism = synthetic construct
SEQUENCE: 14
aaacctgcca catgactcat ccctc                                             25

SEQ ID NO: 15          moltype = DNA  length = 51
FEATURE                Location/Qualifiers
misc_feature           1..51
                       note = Synthetic YFPf primer
misc_feature           1..51
                       note = YFPf primer
source                 1..51
                       mol_type = other DNA
                       organism = synthetic construct
SEQUENCE: 15
tctaatacga ctcactatag ggagaggtct atataagcag agctcgttta g                51

SEQ ID NO: 16          moltype = DNA  length = 25
FEATURE                Location/Qualifiers
misc_feature           1..25
                       note = Synthetic YFPr primer
misc_feature           1..25
                       note = YFPr primer
source                 1..25
                       mol_type = other DNA
                       organism = synthetic construct
SEQUENCE: 16
ggccatgata tagacgttgt ggctg                                             25

SEQ ID NO: 17          moltype = DNA  length = 23
FEATURE                Location/Qualifiers
misc_feature           1..23
                       note = Synthetic hMyd88f2 primer
misc_feature           1..23
                       note = hMyd88f2 primer
source                 1..23
                       mol_type = other DNA
                       organism = synthetic construct
SEQUENCE: 17
ttacgccccc cacatcaccc gcc                                               23
```

```
SEQ ID NO: 18              moltype = DNA  length = 24
FEATURE                    Location/Qualifiers
misc_feature               1..24
                           note = Synthetic hMyd88r1 primer
misc_feature               1..24
                           note = hMyd88r1 primer
source                     1..24
                           mol_type = other DNA
                           organism = synthetic construct
SEQUENCE: 18
gtctccagtt gccggatctc caag                                              24

SEQ ID NO: 19              moltype = DNA  length = 23
FEATURE                    Location/Qualifiers
misc_feature               1..23
                           note = Synthetic mMyd88f2 primer
misc_feature               1..23
                           note = mMyd88f2 primer
source                     1..23
                           mol_type = other DNA
                           organism = synthetic construct
SEQUENCE: 19
ggaaactcca caggcgagcg tac                                               23

SEQ ID NO: 20              moltype = DNA  length = 26
FEATURE                    Location/Qualifiers
misc_feature               1..26
                           note = Synthetic mMyd88r2 primer
misc_feature               1..26
                           note = mMyd88r2 primer
source                     1..26
                           mol_type = other DNA
                           organism = synthetic construct
SEQUENCE: 20
ggcagtcctc ctcgatgcgc gacttc                                            26

SEQ ID NO: 21              moltype = DNA  length = 119
FEATURE                    Location/Qualifiers
misc_feature               1..119
                           note = Synthetic Flag-DDX3 primer
misc_feature               1..119
                           note = Flag-DDX3 primer
source                     1..119
                           mol_type = other DNA
                           organism = synthetic construct
SEQUENCE: 21
actcgcttag cagcggaaga ctccgagttc tcggtactct tcagggatgg actacaagga       60
cgacgatgac aagagtcatg tggcagtgga aaatgcgctc gggctggacc agcaggtga      119

SEQ ID NO: 22              moltype = AA  length = 1958
FEATURE                    Location/Qualifiers
REGION                     1..1958
                           note = Synthetic GAG-Cas9 fusion protein
REGION                     1..1958
                           note = GAG-Cas9 fusion protein
source                     1..1958
                           mol_type = protein
                           organism = synthetic construct
SEQUENCE: 22
MGQAVTTPLS LTLDHWKDVE RTAHNLSVEV RKRRWVTFCS AEWPTFNVGW PRDGTFNPDI        60
ITQVKIKVFS PGPHGHPDQV PYIVTWEAIA VDPPPWVRPF VHPKPPLSLP PSAPSLPPEP       120
PLSTPPQSSL YPALTSPLNT KPRPQVLPDS GGPLIDLLTE DPPPYRDPGP SPSPDGNGDSG      180
EVAPTEGAPD PSPMVSRLRG RKEPPVADST TSQAFPLRLG GNGQYQYWPF SSSDLYNWKN       240
NNPSFSEDPA KLTALIESVL LTHQPTWDDC QQLLGTLLTG EEKQRVLLEA RKAVRGEDGR       300
PTQLPNDIND AFPLERPDWD YNTQRGRNHL VHYRQLLLAG LQNAGRSPTN LAKVKGITQG       360
PNESPSAFLE RLKEAYRRYT PYDPEDPGQE TNVAMSFIWQ SAPDIGRKLE RLEDLKSKTL       420
GDLVREAEKI FNKRETPEER EERIRRETEE KEERRRAEDV QREKERDRRR HREMSKLLAT       480
VVSGQRQDRQ GGERRRPQLD HDQCAYCKEK GHWARDCPKK PRGPRGPRPQ ASLLTRSSLY       540
PALTPTGDYK DDDDKMAPKK KRKVGIHGVP AADKKYSIGL DIGTNSVGWA VITDEYKVPS       600
KKFKVLGNTD RHSIKKNLIG ALLFDSGETA EATRLKRTAR RRYTRRKNRI CYLQEIFSNE       660
MAKVDDSFFH RLEESFLVEE DKKHERHPIF GNIVDEVAYH EKYPTIYHLR KKLVDSTDKA       720
DLRLIYLALA HMIKFRGHFL IEGDLNPDNS DVDKLFIQLV QTYNQLFEEN PINASGVDAK       780
AILSARLSKS RRLENLIAQL PGEKKNGLFG NLIALSLGLT PNFKSNFDLA EDAKLQLSKD       840
TYDDDLDNLL AQIGDQYADL FLAAKNLSDA ILLSDILRVN TEITKAPLSA SMIKRYDEHH       900
QDLTLLKALV RQQLPEKYKE IFFDQSKNGY AGYIDGGASQ EEFYKFIKPI LEKMDGTEEL       960
LVKLNREDLL RKQRTFDNGS IPHQIHLGEL HAILRRQEDF YPFLKDNREK IEKILTFRIP      1020
YYVGPLARGN SRFAWMTRKS EETITPWNFE EVVDKGASAQ SFIERMTNFD KNLPNEKVLP      1080
KHSLLYEYFT VYNELTKVKY VTEGMRKPAF LSGEQKKAIV DLLFKTNRKV TVKQLKEDYF      1140
```

```
KKIECFDSVE ISGVEDRFNA SLGTYHDLLK IIKDKDFLDN EENEDILEDI VLTLTLFEDR  1200
EMIEERLKTY AHLFDDKVMK QLKRRRYTGW GRLSRKLING IRDKQSGKTI LDFLKSDGFA  1260
NRNFMQLIHD DSLTFKEDIQ KAQVSGQGDS LHEHIANLAG SPAIKKGILQ TVKVVDELVK  1320
VMGRHKPENI VIEMARENQT TQKGQKNSRE RMKRIEEGIK ELGSQILKEH PVENTQLQNE  1380
KLYLYLQNG  RDMYVDQELD INRLSDYDVD HIVPQSFLKD DSIDNKVLTR SDKNRGKSDN  1440
VPSEEVVKKM KNYWRQLLNA KLITQRKFDN LTKAERGGLS ELDKAGFIKR QLVETRQITK  1500
HVAQILDSRM NTKYDENDKL IREVKVITLK SKLVSDFRKD FQFYKVREIN NYHHAHDAYL  1560
NAVVGTALIK KYPKLESEFV YGDYKVYDVR KMIAKSEQEI GKATAKYFFY SNIMNFFKTE  1620
ITLANGEIRK RPLIETNGET GEIVWDKGRD FATVRKVLSM PQVNIVKKTE VQTGGFSKES  1680
ILPKRNSDKL IARKKDWDPK KYGGFDSPTV AYSVLVVAKV EKGKSKKLKS VKELLGITIM  1740
ERSSFEKNPI DFLEAKGYKE VKKDLIIKLP KYSLFELENG RKRMLASAGE LQKGNELALP  1800
SKYVNFLYLA SHYEKLKGSP EDNEQKQLFV EQHKHYLDEI IEQISEFSKR VILADANLDK  1860
VLSAYNKHRD KPIREQAENI IHLFTLTNLG APAAFKYFDT TIDRKRYTST KEVLDATLIH  1920
QSITGLYETR IDLSQLGGDK RPAATKKAGQ AKKKKARA                         1958

SEQ ID NO: 23           moltype = AA  length = 511
FEATURE                 Location/Qualifiers
REGION                  1..511
                        note = VSV-G protein
REGION                  1..511
                        note = VSV-G protein
source                  1..511
                        mol_type = protein
                        organism = Vesicular stomatitis virus
SEQUENCE: 23
MKCLLYLAFL FIGVNCKFTI VFPHNQKGNW KNVPSNYHYC PSSSDLNWHN DLIGTAIQVK   60
MPKSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 24           moltype = AA  length = 1742
FEATURE                 Location/Qualifiers
REGION                  1..1742
                        note = Synthetic GAG PRO POL polyprotein
REGION                  1..1742
                        note = GAG PRO POL polyprotein
source                  1..1742
                        mol_type = protein
                        organism = synthetic construct
SEQUENCE: 24
MGQAVTTPLS LTLDHWKDVE RTAHNLSVEV RKRRWVTFCS AEWPTFNVGW PRDGTFNPDI   60
ITQVKIKVFS PGPHGHPDQV PYIVTWEAIA VDPPPWVRPF VHPKPPLSLP PSAPSLPPEP  120
PLSTPPQSSL YPALTSPLNT KPRPQVLPDS GGPLIDLLTE DPPPYRDPGP PSPDNGNDSG  180
EVAPTEGAPD PSPMVSRLRG RKEPPVADST TSQAFPLRLG GNGQYQYWPF SSSDLYNWKN  240
NNPSFSEDPA KLTALIESVL LTHQPTWDDC QQLLGTLLTG EEKQRVLLEA RKAVRGEDGR  300
PTQLPNDIND AFPLERPDWD YNTQRGRNHL VHYRQLLLAG LQNAGRSPTN LAKVKGITQG  360
PNESPSAFLE RLKEAYRRYT PYDPEDPGQE TNVAMSFIWQ SAPDIGRKLE RLEDLKSKTL  420
GDLVREAEKI FNKRETPEER EERIRRETEE KEERRRAEDV QREKERDRRR HREMSKLLAT  480
VVSGQRDRQ  GGERRRPQLD HDQCAYCKEK GHWARDCPKK PRGPRGPRPQ ASLLTLDDTL  540
DDQGGQGQEP PPEPRITLRV GGQPVTFLVD TGAQHSVLTQ NPGPLSDKSA WVQGATGGKR  600
YRWTTDRRVH LATGKVTHSF LHVPDCPYPL LGRDLLTKLK AQIHFEGSGA QVVGPMGQPL  660
QVLTLNIEDE YRLHETSKGP DVPLGSTWLS DFPQAWAETG GMGLAVRQAP LIIPLKATST  720
PVSIKQYPMS QEARLGIKPH IQRLLDQGIL VPCQSPWNTP LLPVKKPGTN DYRPVQDLRE  780
VNKRVEDIHP TVPNPYNLLS GLPPSHQWYT VLDLKDAFFC LRLHPTSQSL FAFEWRDPEM  840
GISGQLTWTR LPQGFKNSPT LFDEALHRDL ADFRIQHPDL ILLQYVDDLL LAATSELDCQ  900
QGTRALLQTL GDLGYRASAK KAQICQKQVK YLGYLLKEGQ RWLTEARKET VMGQPTPKTP  960
RQLREFLGTA GFCRLWIPGF AEMAAPLYPL TKTGTLFEWG PDQQKAYQEI KQALLTAPAL 1020
GLPDLTKPFE LFVDEKQGYA KGVLTQKLGP WRRPVAYLSK KLDPVAAGWP PCLRMVAAIA 1080
VLTKDAGKLT MGQPLVILAP HAVEALVKQP PDRWLSNARM THYQALLLDT DRVQFGPIVA 1140
LNPATLLPLP EEGLQHDCLD ILAEAHGTRP DLTDQPLPDA DHTWYTDGSS FLQEGQRKAG 1200
AAVTTETEVV WAKALPAGTS AQRAELIALT QALKMAEGKK LNVYTDSRYA FATAHIHGEI 1260
YRRRGLLTSE GKEIKNKDEI LALLKALFLP KRLSIIHCPG HQKGNRAEAR GNRMADQAAR 1320
EVATRETPET STLLIENSAP YTHEHFHYTV TDIKDLTKLG AYDDAKKCW  VYQGKPVMPD 1380
QFTFELLDFL HQLTHLSFSK TKALLERNYC PYYMLNRDRT LKDITETCQA CAQVNASKSA 1440
VKQGTRVRGH RPGTHWEIDF TEVKPGLYGY KYLLVFIDTF SGWVEAFPTK KETAKVVTKK 1500
LLEEIFPRFG MPQVLGTDNG PAFVSKVSQT VADLLGVDWK LHCAYRPQSS GQVERMNRTI 1560
KETLTKLTLA TGSRDWVLLL PLALYRARNT PGPHGLTPYE ILYGAPPPLV NFPDPDMAKV 1620
THNPSLQAHL QALYLVQHEV WRPLAAAYQE QLDRPVVPHP FRVGDTVWVR RHQTKNLEPR 1680
WKGPYTVLLT TPTALKVDGI AAWIHAAHVK AADTRIEPPS ESTWRVQRSQ NPLKIRLTRG 1740
TS                                                              1742

SEQ ID NO: 25           moltype = AA  length = 546
FEATURE                 Location/Qualifiers
REGION                  1..546
```

|  | note = BAEV-G protein |  |
| --- | --- | --- |
| REGION | 1..546 |  |
|  | note = BAEV-G protein |  |
| source | 1..546 |  |
|  | mol_type = protein |  |
|  | organism = Baboon endogenous retrovirus |  |

SEQUENCE: 25
```
MGFTTKIIFL YNLVLVYAGF DDPRKAIELV QKRYGRPCDC SGGQVSEPPS DRVSQVTCSG   60
KTAYLMPDQR WKCKSIPKDT SPSGPLQECP CNSYQSSVHS SCYTSYQQCR SGNKTYYTAT  120
LLKTQTGGTS DVQVLGSTNK LIQSPCNGIK GQSICWSTTA PIHVSDGGGP LDTTRIKSVQ  180
RKLEEIHKAL YPELQYHPLA IPKVRDNLMV DAQTLNILNA TYNLLLMSNT SLVDDCWLCL  240
KLGPPTPLAI PNFLLSYVTR SSDNISCLII PPLLVQPMQF SNSSCLFSPS YNSTEEIDLG  300
HVAFSNCTSI TNVTGPICAV NGSVFLCGNN MAYTYLPTNW TGLCVLATLL PDIDIIPGDE  360
PVPIPAIDHF IYRPKRAIQF IPLLAGLGIT AAFTTGATGL GVSVTQYTKL SNQLISDVQI  420
LSSTIQDLQD QVDSLAEVVL QNRRGLDLLT AEQGGICLAL QEKCCFYVNK SGIVRDKIKT  480
LQEELERRRK DLASNPLWTG LQGLLPYLLP FLGPLLTLLL LLTIGPCIFN RLTAFINDKL  540
NIIHAM                                                              546
```

| SEQ ID NO: 26 | moltype = DNA  length = 5877 |
| --- | --- |
| FEATURE | Location/Qualifiers |
| misc_feature | 1..5877 |
|  | note = Synthetic sequence encoding Gag-Cas9 fusion protein |
| misc_feature | 1..5877 |
|  | note = sequence encoding Gag-Cas9 fusion protein |
| source | 1..5877 |
|  | mol_type = other DNA |
|  | organism = synthetic construct |

SEQUENCE: 26
```
atgggccagg ctgttaccac ccccttaagt ttgactttag accactggaa ggatgtcgaa   60
cggacagccc acaacctgtc ggtagaggtt agaaaaaggc gctgggttac attctgctct  120
gcagaatggc caaccttcaa cgtcggatgg ccacgagacg gcacttttaa cccagacatt  180
attacacagg ttaagatcaa ggtccttctca cctggcccac atggacatcc ggatcaggtc  240
ccctacatcg tgacctggga agctatagca gtagaccccc ctccctgggt cagacccttc  300
gtgcacccta aacctcccct ctctcttccc ccttcagcct cctctctccc acctgaaccc  360
ccactctcga ccccgcccca gtcctccctc tatccggctc tcacttctcc tttaaacacc  420
aaacctaggc tcaagtcct tcctgatagc ggaggaccac tcattgatct actcacggag  480
gaccctccgc cttaccggga cccagggcca ccctctcctg acgggaacgg cgatagcgga  540
gaagtggccc tacagaagg agcccctgac ccttccccaa tggtatcccg cctgcgggga  600
agaaaagaac cccccgtggc ggattctact acctctcagg cgttccccct tcgcctggga  660
gggaatggac agtatcaata ctggccattt tcctcctctg acctctataa ctggaaaaat  720
aacaacccct ctttctccga ggaccagct aaattgacag ctttgatcga gtccgttctc  780
cttactcatc agcccacttg ggatgactgc aacagctat tagggaccct gctgacggga  840
gaagaaaaac agcgagtgct cctagaagcc cgaaaggccg ttcgagggga ggacggacgg  900
ccaactcagc tgcccaatga cattaatgat gcttttccct ggaacgtcc cgactggac   960
tacaacaccc aacgagtag gaaccaccta gtccactatc gccagttgct cctagcgggt  1020
ctccaaaacg cgggcagaag ccccaccaat ttggccaagg taaagggat aacccaggga  1080
cctaatgagt ctccctcagc cttttagag agactcagg aggcctatcg cagatacact  1140
ccttatgacc ctgaggaccc agggcaagaa accaatgtgg ccatgtcatt catctggcag  1200
tccgccccgg atatcgggcg aaagttagag cggttagaag atttgaagag taagaccta  1260
ggagacttag tgagggaagc tgaaaagatc tttaataaac gagaaacccc ggaagaaaga  1320
gaggaacgta ttaggagaga aacagaggaa aaggaagaac gccgtagggc agaggatgtg  1380
cagagagaga aggagaggga ccgcagaaga catagaaaa tgagtaagtt gctggcctact  1440
gtcgttagcg ggcagagaca ggatagacag ggaggagagc gaaggaggcc caactcgac  1500
cacgaccagt gtgcctactg caaagaaaag ggacattggg ctagagattg ccccaagaag  1560
ccaagaggac cccggggacc acgaccccag gcctccctcc tgacgcgtag ttccctgtat  1620
ccagccctca cacctaccgg tgattacaaa gacgatgacg ataagatggc cccaaagaag  1680
aagcggaagg tcggtatcca cggagtccca gcagccgaca gaagtacag catcggcctg  1740
gacatcggca ccaactctgt gggctgggcc gtgatcaccg acgagtacaa ggtgcccagc  1800
aagaaattca aggtgctggg caacaccgac cggcacagca tcaagaagaa cctgatcgga  1860
gccctgctgt tcgacagcgg cgaaacagcc gaggccaccc ggctgaagag aaccgccaga  1920
agaagataca ccagacggaa gaaccggatc tgctatctgc aagagatctt cagcaacgag  1980
atggccaagg tggacgacag cttcttccac agactggaag agtccttcct ggtggaagag  2040
gataagaagc acgagcggca cccatcttc ggcaacatcg tggacgaggt ggcctaccac  2100
gagaagtacc caccatcta ccacctgaga aagaaactgg tggacagcac cgacaaggcc  2160
gacctgcggc tgatctatct ggccctggcc cacatgatca agttccgggg ccacttcctg  2220
atcgagggcg acctgaaccc cgacaacagc gacgtggaca gctgttcat ccagctggtg  2280
cagacctaca accagctgtt cgaggaaac ccatcaacg ccagcggcgt ggacgccaag  2340
gccatcctgt ctgccagact gagcaagagc agacggctgg aaaatctgat cgcccagctg  2400
cccggcgaga agaagaatgg cctgttcggc aacctgattg ccctgagcct gggcctgacc  2460
cccaacttca gagcaactt cgacctggcc gaggatgcca aactgcagct gagcaaggac  2520
acctacgacg acgacctgga caacctgctg gcccagatcg cgaccagta cgccgacctg  2580
tttctggccg ccaagaacct gtccgacgcc atcctgctga gcgacatcct gagagtgaac  2640
accgagatca ccaaggcccc cctgagcgcc tctatgatca gagatacga cgagcaccac  2700
caggacctga cccctgtgaa agtctctgtg cggcacgaa tgcctgaga gtacaaggac  2760
atttttcttcg accagagcaa gaacggctac gccggctaca ttgacggcgg agccagccag  2820
gaagagttct acaagttcat caagcccatc ctggaaaaga tggacggcac cgaggaactg  2880
ctcgtgaagc tgaacagaga ggacctgctg cggaagcagc ggaccttcga caacggcagc  2940
atcccccacc agatccacct gggagagctg cacgccattc tgcggcggca ggaagatttt  3000
taccccattcc tgaaggacaa ccgggaaaag atcgagaaga tcctgacctt cgcatcccc  3060
```

-continued

```
tactacgtgg gccctctggc caggggaaac agcagattcg cctggatgac cagaaagagc  3120
gaggaaacca tcacccccctg gaacttcgag gaagtggtgg acaagggcgc ttccgcccag  3180
agcttcatcg agcggatgac caacttcgat aagaacctgc ccaacgagaa ggtgctgccc  3240
aagcacagcc tgctgtacga gtacttcacc gtgtataacg agctgaccaa agtgaaatac  3300
gtgaccgagg gaatgagaaa gcccgccttc ctgagcggcg agcagaaaaa ggccatcgtg  3360
gacctgctgt tcaagaccaa ccggaaagtg accgtgaagc agctgaaaga ggactacttc  3420
aagaaaatcg agtgcttcga ctccgtggaa atctccggcg tggaagatcg gttcaacgcc  3480
tccctgggca cataccacga tctgctgaaa attatcaagg acaaggactt cctggacaat  3540
gaggaaaacg aggacattct ggaagatatc gtgctgaccc tgacactgtt tgaggacaga  3600
gagatgatcg aggaacggct gaaaacctat gcccacctgt tcgacgacaa agtgatgaag  3660
cagctgaagc ggcggagata caccggctgg ggcaggctga gccggaagct gatcaacggc  3720
atccgggaca agcagtccgg caagacaatc ctggatttcc tgaagtccga cggcttcgcc  3780
aacagaaact tcatgcagct gatccacgac gacagcctga cctttaaaga ggacatccag  3840
aaagcccagg tgtccggcca gggcgatagc ctgcacgagc acattgccaa tctggccggc  3900
agccccgcca ttaagaaggg catcctgcag acagtgaagg tggtggacga gctcgtgaaa  3960
gtgatgggcc ggcacaagcc cgagaacatc gtgatcgaaa tggccagaga gaaccagacc  4020
acccagaagg gacagaagaa cagccgcgag agaatgaagc ggatcgaaga gggcatcaaa  4080
gagctgggca gccagatcct gaaagaacac cccgtggaaa acacccagct gcagaacgag  4140
aagctgtacc tgtactacct gcagaatggg cgggatatgt acgtggacca ggaactggac  4200
atcaaccggc tgtccgacta cgatgtggac catatcgtgc ctcagagctt tctgaaggac  4260
gactccatcg acaacaaggt gctgaccaga agcgacaaga accggggcaa gagcgacaac  4320
gtgccctccg aagaggtcgt gaagaagatg aagaactact ggcggcagct gctgaacgcc  4380
aagctgatta cccagagaaa gttcgacaat ctgaccaagg ccgagagagg cggcctgagc  4440
gaactggata aggccggctt catcaagaga cagctggtgg aaacccggca gatcacaaag  4500
cacgtggcac agatcctgga ctcccggatg aacactaagt acgacgagaa tgacaagctg  4560
atccgggaag tgaaagtgat caccctgaag tccaagctgg tgtccgattt ccggaaggat  4620
ttccagtttt acaaagtgcg cgagatcaac aactaccacc acgcccacga cgcctacctg  4680
aacgccgtcg tgggaaccgc cctgatcaaa aagtacccta agctggaaag cgagttcgtg  4740
tacggcgact acaaggtgta cgacgtgcgg aagatgatcg ccaagagcga gcaggaaatc  4800
ggcaaggcta ccgccaagta cttcttctac agcaacatca tgaacttttt caagaccgag  4860
attaccctgg ccaacggcga gatccggaag cggcctctga tcgagacaaa cggcgaaacc  4920
ggggagatcg tgtgggataa gggccgggat tttgccaccg tgcggaaagt gctgagcatg  4980
ccccaagtga atatcgtgaa aaagaccgag gtgcagacag gcggcttcag caaagagtct  5040
atcctgccca agaggaacag cgataagctg atcgccagaa agaaggactg ggaccctaag  5100
aagtacggcg gcttcgacag ccccaccgtg gcctattctg tgctggtggt ggccaaagtg  5160
gaaaagggca agtccaagaa actgaagagt gtgaaagagc tgctggggat caccatcatg  5220
gaaagaagca gcttcgagaa gaatcccatc gactttctgg aagccaaggg ctacaaagaa  5280
gtgaaaaagg acctgatcat caagctgcct aagtactccc tgttcgagct ggaaaacggc  5340
cggaagagaa tgctggcctc tgccggcgaa ctgcagaagg gaaacgaact ggccctgccc  5400
tccaaatatg tgaacttcct gtacctggcc agccactatg agaagctgaa gggctccccc  5460
gaggataatg agcagaaaca gctgtttgtg gaacagcaca agcactacct ggacgagatc  5520
atcgagcaga tcagcgagtt ctccaagaga gtgatcctgg ccgacgctaa tctggacaaa  5580
gtgctgtccg cctacaacaa gcaccgggat aagcccatca gagagcaggc cgagaatatc  5640
atccacctgt ttaccctgac caatctggga gcccctgccg ccttcaagta ctttgacacc  5700
accatcgacc ggaagaggta caccagcacc aaagaggtgc tggacgccac cctgatccac  5760
cagagcatca ccggcctgta cgagacacgg atcgacctgt ctcagctggg aggcgacaag  5820
cgtcctgctg ctactaagaa agctggtcaa gctaagaaaa agaaagctag agcttga     5877
```

```
SEQ ID NO: 27          moltype = DNA  length = 1641
FEATURE                Location/Qualifiers
misc_feature           1..1641
                       note = sequence encoding BAEV-G
misc_feature           1..1641
                       note = sequence encoding BAEV-G
source                 1..1641
                       mol_type = unassigned DNA
                       organism = baboon endogenous retrovirus
SEQUENCE: 27
atgggcttta ccaccaagat tatttttctg tataacctgg tgctggtgta tgcgggcttt  60
gatgatccgc gcaaagcgat tgaactggtg cagaaacgct atggccgccc gtgcgattgc  120
agcggcggcc aggtgagcga accgccgagc gatcgcgtga gccaggtgac ctgcagcggc  180
aaaaccgcgt atctgatgcc ggatcagcgc tggaaatgca aaagcattcc gaaagatacc  240
agcccgagcg gcccgctgca ggaatgcccg tgcaacagct atcagagcag cgtgcatagc  300
agctgctata ccagctatca gcagtgccgc agcggcaaca aaacctatta taccgcgacc  360
ctgctgaaaa cccagaccgg cggcaccagc gatgtgcagg tgctgggcag caccaacaaa  420
ctgattcaga gcccgtgcaa cggcattaaa ggccagagca tttgctggag caccaccgcg  480
ccgattcatg tgagcgatgg cggcggcccg ctggatacca cccgcattaa aagcgtgcag  540
cgcaaactgg aagaaattca taaagcgctg tatccggaac tgcagtatca tccgctggcg  600
attccgaaag tgcgcgataa cctgatggtg gatgcgcaga ccctgaacat tctgaacgcg  660
acctataacc tgctgctgat gagcaacacc agcctggtgg atgattgctg gctgtgcctg  720
aaactgggcc cgccgacccc gctggcgatt ccgaactttc tgctgagcta tgtgacccgc  780
agcagcgata acattagctg cctgattatt ccgccgctgc tggtgcagcc gatgcagttt  840
agcaacagca gctgcctgtt tagcccgagc tataacagca ccgaagaaat tgatctgggc  900
catgtggcgt ttagcaactg caccagcatt accaacgtga ccggcccgat ttgcgcggtg  960
aacggcagcg tgtttctgtg cggcaacaac atggcgtata cctatctgcc gaccaactgg  1020
accggcctgt gcgtgctggc gaccctgctg ccggatattg atattattcc gggcgatgaa  1080
ccggtgccga ttccggcgat tgatcatttt atttatcgcc cgaaacgcgc gattcagttt  1140
attccgctgc tggcgggcct gggcattacc gcggcgttta ccaccggcgc gaccggcctg  1200
ggcgtgagcg tgacccagta taccaaactg agcaaccagc tgattagcga tgtgcagatt  1260
```

-continued

```
ctgagcagca ccattcagga tctgcaggat caggtggata gcctggcgga agtggtgctg  1320
cagaaccgcc gcggcctgga tctgctgacc gcggaacagg gcggcatttg cctggcgctg  1380
caggaaaaat gctgctttta tgtgaacaaa agcggcattg tgcgcgataa aattaaaacc  1440
ctgcaggaag aactggaacg ccgccgcaaa gatctggcga gcaacccgct gtggaccggc  1500
ctgcagggcc tgctgccgta tctgctgccg tttctgggcc cgctgctgac cctgctgctg  1560
ctgctgacca ttggcccgtg cattttttaac cgcctgaccg cgtttattaa cgataaactg  1620
aacattattc atgcgatgta a                                         1641

SEQ ID NO: 28          moltype = DNA  length = 1536
FEATURE                Location/Qualifiers
misc_feature           1..1536
                       note = sequence encoding VSV-G protein
misc_feature           1..1536
                       note = sequence encoding VSV-G protein
source                 1..1536
                       mol_type = unassigned DNA
                       organism = Vesicular stomatitis virus
SEQUENCE: 28
atgaagtgcc ttttgtactt agcctttttta ttcattgggg tgaattgcaa gttcaccata  60
gtttttccac acaaccaaaa aggaaactgg aaaaatgttc cttctaatta ccattattgc  120
ccgtcaagct cagatttaaa ttggcataat gacttaatag gcacagcctt acaagtcaaa  180
atgcccaaga gtcacaaggc tattcaagca gacggttgga tgtgtcatgc ttccaaatgg  240
gtcactactt gtgatttccg ctggtatgga ccgaagtata taacacattc catccgatcc  300
ttcactccat ctgtagaaca atgcaaggaa agcattgaac aaacgaaaca aggaacttgg  360
ctgaatccag gcttccctcc tcaaagttgt ggatatgcaa ctgtgacgga tgccgaagca  420
gtgattgtcc aggtgactcc tcaccatgtg ctggttgatg aatacacagg agaatgggtt  480
gattcacagt tcatcaacgg aaaatgcagc aattacatat gccccactgt ccataactct  540
acaacctggc attctgacta taaggtcaaa gggctatgtg attctaacct catttccatg  600
gacatcacct tcttctcaga ggacggagag ctatcatccc tgggaaagga gggcacaggg  660
ttcagaagta actactttgc ttatgaaact ggaggcaagg cctgcaaaat gcaatactgc  720
aagcattggg gagtcagact cccatcaggt gtctggttcg agatggctga taaggatctc  780
tttgctgcag ccagattccc tgaatgccca gaagggtcaa gtatctctgc tccatctcag  840
acctcagtgg atgtaagtct aattcaggac gttgagagga tcttggatta ttccctctgc  900
caagaaacct ggagcaaaat cagagcgggt cttccaatct ctccagtgga tctcagctat  960
cttgctccta aaaacccagg aaccggtcct gctttcacca taatcaatgg taccctaaaa  1020
tactttgaga ccagatacat cagagtcgat attgctgctc caatcctctc aagaatggtc  1080
ggaatgatca gtggaactac cacagaaagg gaactgtggg atgactgggc accatatgaa  1140
gacgtggaaa ttggacccaa tggagttctg aggaccagtt caggatataa gtttccttta  1200
tacatgattg gacatggtat gttggactcc gatcttcatc ttagctcaaa ggctcaggtg  1260
ttcgaacatc ctcacattca agacgctgct tcgcaacttc ctgatgatga gagtttattt  1320
tttggtgata ctgggctatc caaaaatcca atcgagcttg tagaaggttg gttcagtagt  1380
tggaaaagct ctattgcctc tttttcttt atcatagggt taatcattgg actattcttg  1440
gttctccgag ttggtatcca tctttgcatt aaattaaagc acaccaagaa aagacagatt  1500
tatacagaca tagagatgaa ccgacttgga aagtaa                         1536

SEQ ID NO: 29          moltype = AA  length = 9
FEATURE                Location/Qualifiers
REGION                 1..9
                       note = Synthetic cleavage sequence
REGION                 1..9
                       note = cleavage sequence
source                 1..9
                       mol_type = protein
                       organism = synthetic construct
SEQUENCE: 29
SSLYPALTP                                                        9

SEQ ID NO: 30          moltype = DNA  length = 27
FEATURE                Location/Qualifiers
misc_feature           1..27
                       note = Synthetic sequence encoding the cleavage sequence of
                        SEQ ID NO. 29
misc_feature           1..27
                       note = sequence encoding the cleavage sequence of SEQ ID
                        NO. 29
source                 1..27
                       mol_type = other DNA
                       organism = synthetic construct
SEQUENCE: 30
agttccctgt atccagccct cacacct                                    27

SEQ ID NO: 31          moltype = AA  length = 1401
FEATURE                Location/Qualifiers
REGION                 1..1401
                       note = Cas9
REGION                 1..1401
                       note = Cas9
source                 1..1401
                       mol_type = protein
```

```
                        organism = Streptococcus sp.
SEQUENCE: 31
MAPKKKRKVG IHGVPAADKK YSIGLDIGTN SVGWAVITDE YKVPSKKFKV LGNTDRHSIK     60
KNLIGALLFD SGETAEATRL KRTARRRYTR RKNRICYLQE IFSNEMAKVD DSFFHRLEES    120
FLVEEDKKHE RHPIFGNIVD EVAYHEKYPT IYHLRKKLVD STDKADLRLI YLALAHMIKF    180
RGHFLIEGDL NPDNSDVDKL FIQLVQTYNQ LFEENPINAS GVDAKAILSA RLSKSRRLEN    240
LIAQLPGEKK NGLFGNLIAL SLGLTPNFKS NFDLAEDAKL QLSKDTYDDD LDNLLAQIGD    300
QYADLFLAAK NLSDAILLSD ILRVNTEITK APLSASMIKR YDEHHQDLTL LKALVRQQLP    360
EKYKEIFFDQ SKNGYAGYID GGASQEEFYK FIKPILEKMD GTEELLVKLN REDLLRKQRT    420
FDNGSIPHQI HLGELHAILR RQEDFYPFLK DNREKIEKIL TFRIPYYVGP LARGNSRFAW    480
MTRKSEETIT PWNFEEVVDK GASAQSFIER MTNFDKNLPN EKVLPKHSLL YEYFTVYNEL    540
TKVKYVTEGM RKPAFLSGEQ KKAIVDLLFK TNRKVTVKQL KEDYFKKIEC FDSVEISGVE    600
DRFNASLGTY HDLLKIIKDK DFLDNEENED ILEDIVLTLT LFEDREMIEE RLKTYAHLFD    660
DKVMKQLKRR RYTGWGRLSR KLINGIRDKQ SGKTILDFLK SDGFANRNFM QLIHDDSLTF    720
KEDIQKAQVS GQGDSLHEHI ANLAGSPAIK KGILQTVKVV DELVKVMGRH KPENIVIEMA    780
RENQTTQKGQ KNSRERMKRI EEGIKELGSQ ILKEHPVENT QLQNEKLYLY YLQNGRDMYV    840
DQELDINRLS DYDVDHIVPQ SFLKDDSIDN KVLTRSDKNR GKSDNVPSEE VVKKMKNYWR    900
QLLNAKLITQ RKFDNLTKAE RGGLSELDKA GFIKRQLVET RQITKHVAQI LDSRMNTKYD    960
ENDKLIREVK VITLKSKLVS DFRKDFQFYK VREINNYHHA HDAYLNAVVG TALIKKYPKL   1020
ESEFVYGDYK VYDVRKMIAK SEQEIGKATA KYFFYSNIMN FFKTEITLAN GEIRKRPLIE   1080
TNGETGEIVW DKGRDFATVR KVLSMPQVNI VKKTEVQTGG FSKESILPKR NSDKLIARKK   1140
DWDPKKYGGF DSPTVAYSVL VVAKVEKGKS KKLKSVKELL GITIMERSSF EKNPIDFLEA   1200
KGYKEVKKDL IIKLPKYSLF ELENGRKRML ASAGELQKGN ELALPSKYVN FLYLASHYEK   1260
LKGSPEDNEQ KQLFVEQHKH YLDEIIEQIS EFSKRVILAD ANLDKVLSAY NKHRDKPIRE   1320
QAENIIHLFT LTNLGAPAAF KYFDTTIDRK RYTSTKEVLD ATLIHQSITG LYETRIDLSQ   1380
LGGDKRPAAT KKAGQAKKKK A                                             1401

SEQ ID NO: 32           moltype = DNA   length = 4205
FEATURE                 Location/Qualifiers
misc_feature            1..4205
                        note = encoding Cas9
misc_feature            1..4205
                        note = encoding Cas9
source                  1..4205
                        mol_type = unassigned DNA
                        organism = Streptococcus sp.
SEQUENCE: 32
atggcccccaa agaagaagcg gaaggtcggt atccacggag tcccagcagc cgacaagaag     60
tacagcatcg gcctggacat cggcaccaac tctgtgggct gggccgtgat caccgacgag    120
tacaaggtgc ccagcaagaa attcaaggtg ctgggcaaca ccgaccgcca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac agcttcttcc acagactgga ggaagtgagc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggccacat gatcaagttc    540
cggggccact tcctgatcga gggcgacctg aaccccgaca cagcgacgt ggacaagctg    600
ttcatccagc tggtgcagac ctacaaccag ctgttcgagg aaaaccccat caacgccagc    660
ggcgtggacg ccaaggccat cctgtctgcc agactgagca gagcagacg gctgaaaat    720
ctgatcgccc agctgcccgg cgagaagaag aatggcctgt tcggcaacct gattgccctg    780
agcctgagca ccccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gcccccctga gcgcctctat gatcaagaga   1020
tacgacgagc accaccagga cctgaccctg ctgaaagctc tcgtgcggca gcagctgcct   1080
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcgcaa gcagcggacc   1260
ttcgacaacg gcagcatccc ccaccagatc cacctgggag agctgcacgc cattctgcgg   1320
cggcaggaag attttaccc attcctgaag gacaaccgga aaagatcga gaagatcctg   1380
accttccgca tccccatacta cgtgggccct ctggccaggg gaaacagcag attcgcctgg   1440
atgaccagaa agagcgagga aaccatcacc cctggaact cgaggaagt ggtggacaag   1500
ggcgcttccg cccagagctt catcgagcgg atgaccaact cgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga agtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac atttctggaa atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagagacca tccaaaagc tcaggtgtc ggcaggcaca atagcctgca gcgacacatt   2220
gccaatctgg ccggcagccc cgccattaag aagggcatct tgcagacagt gaaggtggtg   2280
gacgagctcg tgaaagtgat gggcggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaag aacaccccgt ggaaaacacc   2460
cagctgcaga acgagaagct gtacctgtac tacctgcaga atgggcggga tatgtacgtg   2520
```

-continued

```
gaccaggaac tggacatcaa ccggctgtcc gactacgatg tggaccatat cgtgcctcag  2580
agctttctga aggacgactc catcgacaac aaggtgctga ccagaagcga caagaaccgg  2640
ggcaagagcg acaacgtgcc ctccgaagag gtcgtgaaga agatgaagaa ctactggcgg  2700
cagctgctga acgccaagct gattacccag agaaagttcg acaatctgac caaggccgag  2760
agaggcggcc tgagcgaact ggataaggcc ggcttcatca agagacagct ggtggaaacc  2820
cggcagatca caaagcacgt ggcacagatc ctggactccc ggatgaacac taagtacgac  2880
gagaatgaca agctgatccg ggaagtgaaa gtgatcaccc tgaagtccaa gctggtgtcc  2940
gatttccgga aggatttcca gttttacaaa gtgcgcgaga tcaacaacta ccaccacgcc  3000
cacgacgcct acctgaacgc cgtcgtggga accgccctga tcaaaaagta ccctaagctg  3060
gaaagcgagt tcgtgtacgg cgactacaag gtgtacgacg tgcggaagat gatcgccaag  3120
agcgagcagg aaatcggcaa ggctaccgcc aagtacttct tctacagcaa catcatgaac  3180
tttttcaaga ccgagattac cctggccaac ggcgagatcc ggaagcggcc tctgatcgag  3240
acaaacggcg aaaccgggga gatcgtgtgg gataagggcc gggattttgc caccgtgcgg  3300
aaagtgctga gcatgcccca agtgaatatc gtgaaaaaga ccgaggtgca gacaggcggc  3360
ttcagcaaag agtctatcct gcccaagagg aacagcgata agctgatcgc cagaaagaag  3420
gactgggacc ctaagaagta cggcggcttc gacagcccca ccgtggccta ttctgtgctg  3480
gtggtggcca aagtggaaaa gggcaagtcc aagaaactga agagtgtgaa agagctgctg  3540
gggatcacca tcatggaaag aagcagcttc gagaagaatc ccatcgactt tctggaagcc  3600
aagggctaca aagaagtgaa aaaggacctg atcatcaagc tgcctaagta ctccctgttc  3660
gagctggaaa acggccggaa gagaatgctg gcctctgccg gcgaactgca gaagggaaac  3720
gaactggccc tgccctccaa atatgtgaac ttcctgtacc tggccagcca ctatgagaag  3780
ctgaagggct cccccgagga taatgagcag aaacagctgt ttgtggaaca gcacaagcac  3840
tacctggacg agatcatcga gcagatcagc gagttctcca agagagtgat cctggccgac  3900
gctaatctgg acaaagtgct gtccgcctac aacaagcacc gggataagcc catcagagag  3960
caggccgaga atatcatcca cctgtttacc ctgaccaatc tgggagcccc tgccgccttc  4020
aagtactttg acaccaccat cgaccggaag aggtacacca gcaccaaaga ggtgctggac  4080
gccaccctga tccaccagag catcaccggc ctgtacgaga cacggatcga cctgtctcag  4140
ctgggaggcg acaagcgtcc tgctgctact aagaaagctg gtcaagctaa gaaaaagaaa  4200
gctag                                                               4205

SEQ ID NO: 33           moltype = DNA  length = 12150
FEATURE                 Location/Qualifiers
misc_feature            1..12150
                        note = Synthetic HIV-1 encapsidation construct
misc_feature            1..12150
                        note = HIV-1 encapsidation construct
source                  1..12150
                        mol_type = other DNA
                        organism = synthetic construct
SEQUENCE: 33
ttgattattg actagttatt aatagtaatc aattacgggg tcattagttc atagcccata  60
tatggagttc cgcgttacat aacttacggt aaatggcccg cctggctgac cgcccaacga  120
cccccgccca ttgacgtcaa taatgacgta tgttcccata gtaacgccaa tagggacttt  180
ccattgacgt caatgggtgg agtatttacg gtaaactgcc cacttggcag tacatcaagt  240
gtatcatatg ccaagtacgc cccctattga cgtcaatgac ggtaaatggc ccgcctggca  300
ttatgcccag tacatgacct tatgggactt tcctacttgg cagtacatct acgtattagt  360
catcgctatt accatggtga tgcggttttg gcagtacatc aatgggcgtg gatagcggtt  420
tgactcacgg ggatttccaa gtctccaccc cattgacgtc aatgggagtt tgttttggca  480
ccaaaatcaa cgggactttc caaaatgtcg taacaactcc gccccattga cgcaaatggg  540
cggtaggcgt gtacggtggg aggtctatat aagcagagct cgtttagtga accgtcagat  600
cgcctggaga cgccatccac gctgttttga cctccataga agacaccggg accgatccag  660
cctccgcggc cgggaacggt gcattggaac gcggattccc cgtgccaaga gtgacgtaag  720
taccgcctat agagtctata ggcccacccc cttggcttct tatgcgacgg atcgatcccg  780
taataagctt cgaggtccgc ggccggccgc gttgacgcgc acggcaagag gcgaggggcg  840
gcgactggtg agagatgggt gcgagagcgt cagtattaag cgggggagaa ttagatcgat  900
gggaaaaaat tcggttaagg ccagggggaa agaaaaaata taaattaaaa catatagtat  960
gggcaagcag ggagctagaa cgattcgcag ttaatcctgg cctgttagaa acatcagaag  1020
gctgtagaca aatactggga cagctacaac catcccttca gacaggatca gaagaactta  1080
gatcattata taatacagta gcaaccctct attgtgtgca tcaaaggata gagataaaag  1140
acaccaagga agctttagac aagatagagg aagagcaaaa caaaagtaag aaaaaagcac  1200
agcaagcagc agctgacaca ggacacagca atcaggtcag ccaaaattac cctatagtgc  1260
agaacatcca ggggcaaatg gtacatcagg ccatatcacc tagaacttta aatgcatggg  1320
taaaagtagt agaagagaag gctttcagcc cagaagtgat acccatgttt tcagcattat  1380
cagaaggagc caccccacaa gatttaaaca ccatgctaaa cacagtgggg ggacatcaag  1440
cagccatgca aatgttaaaa gagaccatca atgaggaagc tgcagaatgg gatagagtgc  1500
atccagtgca tgcagggcct attgcaccag gccagatgag agaaccaagg ggaagtgaca  1560
tagcaggaac tactagtacc cttcaggaac aaataggatg gatgacacat aatccaccta  1620
tcccagtagg agaaatctat aaaagatgga taatcctggg attaaataaa atagtaagaa  1680
tgtatagccc taccagcatt ctggacataa gacaaggacc aaaggaaccc tttagagact  1740
atgtagaccg attctataaa actctaagag ccgagcaagc ttcacaagag gtaaaaaatt  1800
ggatgacaga aaccttgttg gtccaaaatg cgaacccaga ttgtaagact attttaaaag  1860
cattgggacc aggagcgaca ctagaagaaa tgatgacagc atgtcaggga gtggggggac  1920
ccggccataa agcaagagtt ttggctgaag caatgagcca agtaacaaat ccagctacca  1980
taatgataca gaaaggcaat tttaggaacc aaagaaagac tgttaagtgt ttcaattgtg  2040
gcaaagaagg gcacatagcc aaaaattgca gggcccctag gaaaaagggc tgttggaaat  2100
gtggaaagga aggacaccaa atgaaagatt gtactgagag acaggctaat tttttaggga  2160
agatctggcc ttcccacaag ggaaggccag ggaattttct tcagagcaga ccagagccaa  2220
cagccccacc agaagagagc ttcaggtttg gggaagagac aacaactccc tctcagaagc  2280
aggagccgat agacaaggaa ctgtatcctt tagcttccct cagatcactc tttggcagcg  2340
```

```
accccctcgtc acaataaaga taggggggca attaaaggaa gctctattag atacaggagc 2400
agatgataca gtattagaag aaatgaattt gccaggaaga tggaaaccaa aaatgatagg 2460
gggaattgga ggtttttatca aagtaagaca gtatgatcag atactcatag aaatctgcgg 2520
acataaagct ataggtacag tattagtagg acctacacct gtcaacataa ttggaagaaa 2580
tctgttgact cagattggct gcactttaaa ttttcccatt agtcctattg agactgtacc 2640
agtaaaatta aagccaggaa tggatggccc aaaagttaaa caatggccat tgacagaaga 2700
aaaaataaaa gcattagtag aaatttgtac agaaatggaa aaggaaggaa aaatttcaaa 2760
aattgggcct gaaaatccat acaatactcc agtatttgcc ataaagaaaa aagacagtac 2820
taaatggaga aaattagtag atttcagaga acttaataag agaactcaag atttctggga 2880
agttcaatta ggaataccac atcctgcagg gttaaaacag aaaaaatcag taacagtact 2940
ggatgtgggc gatgcatatt tttcagttcc cttagataaa gacttcagga agtatactgc 3000
atttaccata cctagtataa acaatgagac accagggatt agatatcagt acaatgtgct 3060
tccacaggga tggaaaggat caccagcaat attccagtgt agcatgacaa aaatcttaga 3120
gccttttaga aaacaaaatc cagacatagt tcatctatca tacatggatg atttgtatgt 3180
aggatctgac ttagaaatag ggcagcatag aacaaaaata gaggaactga gacaacatct 3240
gttgaggtgg ggatttacca caccagacaa aaaacatcag aaagaacctc cattcctttg 3300
gatgggttat gaactccatc ctgataaatg gacagtacag cctatagtgc tgccagaaaa 3360
ggacagctgg actgtcaatg acatacagaa attagtggga aaattgaatt gggcaagtca 3420
gatttatgca gggattaaag taaggcaatt atgtaaactt cttaggggaa ccaaagcact 3480
aacagaagta gtaccactaa cagaagaagc agagctagaa ctggcagaaa cagggagat 3540
tctaaaagaa ccgtacatg gagtgtatta tgacccatca aaagacttaa tagcagaaat 3600
acagaagcag gggcaaggcc aatggacata tcaaatttat caagagccat ttaaaaatct 3660
gaaaacagga aagtatgcaa gaatgaaggg tgcccacact aatgatgtga aacaattaac 3720
agaggcagta caaaaaatag ccacagaaag catagtaata tggggaaaga ctcctaaatt 3780
taaattaccc atacaaaagg aaacatggga agcatggtgg acagagtatt ggcaagccac 3840
ctggattcct gagtgggagt ttgtcaatac ccctccctta gtgaagttat gtaccagtt 3900
agagaaagaa cccataatag gagcagaaac tttctatgta gatggggcag ccaataggga 3960
aactaaatta ggaaaagcag gatatgtaac tgacagagga agacaaaaag ttgtccccct 4020
aacggacaca acaaatcaga agactgagtt acaagcaatt catctagctt tgcaggattc 4080
gggattagaa gtaaacatag tgacagactc acaatatgca ttgggaatca ttcaagcaca 4140
accagataaa agtgaatcag agttagtcag tcaaataata gagcagttaa taaaaaagga 4200
aaaagtctac ctggcatggg taccagcaca caaaggaatt ggaggaaatg aacaagtaga 4260
taaattggtc agtgctggaa tcaggaaagt actatttta gatggaatag ataaggccca 4320
agaagaacat gagaaatatc acagtaattg gagagcaagg gctagtgatt ttaacctacc 4380
acctgtagta gcaaaagaaa tagtagccag ctgtgataaa tgtcagctaa aaggggaagc 4440
catgcatgga caagtagact gtagcccagg aatatggcag ctagattgta cacatttaga 4500
aggaaaagtt atcttggtag cagttcatgt agccagtgga tatatagaag cagaagtaat 4560
tccagcagag acagggcaag aaacagcata cttcctctta aaattagcag gaagatggcc 4620
agtaaaaaca gtacatacag acaatggcag caatttcacc agtactacag ttaaggccgc 4680
ctgttggtgg gcggggatca agcaggaatt tggcattccc tacaatcccc aaagtcaagg 4740
agtaatagaa tctatgaata aagaattaaa gaaaattata ggacaggtaa gagatcaggc 4800
tgaacatctt aagacagcag tacaaatggc agtattcatc cacaatttta aaagaaaagg 4860
ggggattggg gggtacagtg caggggaaag aatagtagac ataatagcaa cagacataca 4920
aactaaagaa ttacaaaaac aaattacaaa aattcaaaat tttcgggttt attacaggga 4980
cagcagagat ccagtttgga aaggaccagc aaagctcctc tggaaaggtg aaggggcagt 5040
agtaatacaa gataatagtg acataaaagt agtgccaaga agaaaagcaa agatcatcag 5100
ggattatgga aaacagatgg caggtgatga ttgtgtggca agtagacagg atgaggatta 5160
acacatggaa ttctgcaaca actgctgttt atccatttca gaattgggtg tcgacatagc 5220
agaataggcg ttactcgaca gaggagagca agaaatggag ccagtagatc ctagactaga 5280
gccctggaag catccaggaa gtcagcctaa aactgcttgt accaattgct attgtaaaaa 5340
gtgttgcttt cattgccaag tttgtttcat gacaaaagcc ttaggcatct cctatggcag 5400
gaagaagcgg agacagcgac gaagagctca tcagaacagt cagactcatc aagcttctct 5460
atcaaagcag taagtagtac atgtaatgca acctataata gtagcaatag tagcattagt 5520
agtagcaata ataatagcaa tagttgtgtg gtccatagta atcatagaat ataggaaaat 5580
ggccgctgat cttcagacct ggaggaggag atatgaggga caattggaga agtgaattat 5640
ataaatataa agtagtaaaa attgaaccat taggagtagc ccccaccaag gcaaagagaa 5700
gagtggtgca gagagaaaaa agagcagtgg gaataggagc tttgttcctt gggttcttgg 5760
gagcagcagg aagcactatg ggcgcagcgt caatgacgct gacggtacag gccagacaat 5820
tattgtctgg tatagtgcag cagcagaaca atttgctgag ggctattgag gcgcaacagc 5880
atctgttgca actcacagtc tggggcatca agcagctcca ggcaagaatc ctggctgtgg 5940
aaagatacct aaaggatcaa cagctcctgg gatttgggg ttgctctgga aaactcattt 6000
gcaccactgc tgtgccttgg aatgctagtt ggagtaataa atctctggaa cagatttgga 6060
atcacacgac ctggatggag tgggacagag aaattaacaa ttacacaagc ttaatacact 6120
ccttaattga agaatcgcaa aaccagcaag aaagaatta ttggaattag 6180
ataaatgggc aagtttgtgg aattggttta acataacaaa ttggctgtgg tatataaat 6240
tattcataat gatagtagga ggcttggtag gtttaagaat agttttgct gtactttcta 6300
tagtgaatag agttaggcag ggatattcac cattatcgtt tcagacccac ctcccaaccc 6360
cgaggggacc cgacaggccc gaaggaatag aagaagaagg tggagagaga gacagagaca 6420
gatccattcg attagtgaac ggatccttgg cacttatctg ggacgatctg cggagcctgt 6480
gcctcttcag ctaccaccgc ttgagagact tactcttgat tgtaacgagg attgtggaac 6540
ttctgggacg caggggtgg gaagccctca atattggtg gaatctccta caatattgga 6600
gtcaggagct aaagaatagt gctgttagct tgctcaatgc cacagccata gcagtagctg 6660
aggggacaga tagggttata gaagtagtac aaggagcttg tagagctatt cgccacatac 6720
ctagaagaat aagacaggga ttttgctata agctgggggc ccggtg 6780
accttcagac cttggcactg gaggtggccc ggcagaagcg cggcatcgtg gatcagtgct 6840
gcaccagcat ctgctctctc taccaactgg agaactactg caactaggcc caccactacc 6900
ctgtccaccc ctctgcaatg aataaaacct ttgaaagagc actacaagtt gtgtgtacat 6960
gcgtgcatgt gcatatgtgg tgcggggga acatgagtgg ggctggctgg agtggcgatg 7020
ataagctgtc aaacatgaga attaattctt gaagacgaaa gggcctcgtg atacgcctat 7080
```

```
ttttataggt taatgtcatg ataataatgg tttcttagtc tagaattaat tccgtgtatt  7140
ctatagtgtc acctaaatcg tatgtgtatg atacataagg ttatgtatta attgtagccg  7200
cgttctaacg acaatatgta caagcctaat tgtgtagcat ctggcttact gaagcagacc  7260
ctatcatctc tctcgtaaac tgccgtcaga gtcggtttgg ttggacgaac cttctgagtt  7320
tctggtaacg ccgtcccgca cccggaaatg gtcagcgaac caatcagcag ggtcatcgct  7380
agccagatcc tctacgccgg acgcatcgtg gccggcatca ccggcgccac aggtgcggtt  7440
gctggcgcct atatcgccga catcaccgat ggggaagatc gggctcgcca cttcgggctc  7500
atgagcgctt gtttcggcgt gggtatggtg gcaggcccg tggccggggg actgttgggc  7560
gccatctcct tgcatgcacc attccttgcg gcggcggtgc tcaacggcct caacctacta  7620
ctgggctgct tcctaatgca ggagtcgcat aagggagagc gtcgaatggt gcactctcag  7680
tacaatctgc tctgatgccg catagttaag ccagccccga cacccgccaa cacccgctga  7740
cgcgccctga cgggcttgtc tgctcccggc atccgcttac agacaagctg tgaccgtctc  7800
cgggagctgc atgtgtcaga ggttttcacc gtcatcaccg aaacgcgcga gacgaaaggg  7860
cctcgtgata cgcctatttt tataggttaa tgtcatgata ataatggttt cttagacgtc  7920
aggtggcact tttcggggaa atgtgcgcgg aaccccctatt tgtttatttt tctaaataca  7980
ttcaaatatg tatccgctca tgagacaata accctgataa atgcttcaat aatattgaaa  8040
aaggaagagt atgagtattc aacatttccg tgtcgccctt attccctttt ttgcggcatt  8100
ttgccttcct gttttgtgctc acccagaaac gctggtgaaa gtaaaagatg ctgaagatca  8160
gttgggtgca cgagtgggtt acatcgaact ggatctcaac agcggtaaga tccttgagag  8220
ttttcgcccc gaagaacgtt ttccaatgat gagcactttt aaagttctgc tatgtggcgc  8280
ggtattatcc cgtattgacg ccgggcaaga gcaactcggt cgccgcatac actattctca  8340
gaatgacttg gttgagtact caccagtcac agaaaagcat cttacggatg gcatgacagt  8400
aagagaatta tgcagtgctg ccataaccat gagtgataac actgcggcca acttacttct  8460
gacaacgatc ggaggaccga aggagctaac cgctttttg cacaacatgg ggatcatgt  8520
aactcgcctt gatcgttggg aaccggagct gaatgaagcc ataccaaacg acgagcgtga  8580
caccacgatg cctgtagcaa tggcaacaac gttgcgcaaa ctattaactg gcgaactact  8640
tactctagct tcccggcaac aattaataga ctggatggag gcggataaag ttgcaggacc  8700
acttctgcgc tcggcccttc cggctggctg gtttattgct gataaatctg gagccggtga  8760
gcgtgggtct cgcggtatca ttgcagcact ggggccagat ggtaagccct cccgtatcgt  8820
agttatctac acgacgggga gtcaggcaac tatggatgaa cgaaatagac agatcgctga  8880
gataggtgcc tcactgatta gcattggta actgtcagac caagtttact catatatact  8940
ttagattgat ttaaaacttc atttttaatt taaaaggatc taggtgaaga tcctttttga  9000
taatctcatg accaaaatcc cttaacgtga gttttcgttc cactgagcgt cagacccgt  9060
agaaaagatc aaaggatctt cttttttctg cgcgtaatct gctgcttgca  9120
aacaaaaaaa ccaccgctac cagcggtggt ttgtttgccg gatcaagagc taccaactct  9180
ttttccgaag gtaactggct tcagcagagc gcagatacca aatactgttc ttctagtgta  9240
gccgtagtta ggccaccact tcaagaactc tgtagcaccg cctacatacc tcgctctgct  9300
aatcctgtta ccagtggctg ctgccagtgg cgataagtcg tgtcttaccg ggttggactc  9360
aagacgatag ttaccggata aggcgcagcg gtcgggctga acggggggt cgtgcacaca  9420
gcccagcttg gagcgaacga cctacaccga actgagatac ctacagcgtg agctatgaga  9480
aagcgccacg cttcccgaag ggagaaaggc ggacaggtat ccggtaagcg cagggtcgg  9540
aacaggagag cgcacgaggg agcttccagg gggaaacgcc tggtatcttt atagtcctgt  9600
cgggtttcgc caccctgac ttgagcgtcg attttgtga tgctcgtcag ggggcggag  9660
cctatggaaa aacgccagca acgcggcctt tttacggttc ctggcctttt gctggccttt  9720
tgctcacatg ttctttcctg cgttatcccc tgattctgtg ataaccgta ttaccgcctt  9780
tgagtgagct gataccgctc gccgcagccg aacgaccgag cgcagcgagt cagtgagcga  9840
ggaagcggaa gagcgcccaa tacgcaaacc gcctctcccc gcgcgttggc cgattcatta  9900
atgcagctgt ggaatgtgtg tcagttaggg tgtggaaagt ccccaggctc cccagcaggc  9960
agaagtatgc aaagcatgca tctcaattag tcagcaacca ggtgtggaaa gtccccaggc 10020
tccccagcag gcagaagtat gcaaagcatg catctcaatt agtcagcaac catagtcccg 10080
ccctaactc cgcccatccc gcccctaact ccgcccagtt ccgcccattc tccgccccat 10140
ggctgactaa ttttttttat ttatgcagag gccgaggccg cctcggcctc tgagctattc 10200
cagaagtagt gaggaggctt ttttggaggc ctaggctttt gcaaaaagct tggacacaag 10260
acaggcttgc gagatatgtt tgagaatacc actttatccc gcgtcaggga gaggcagtgc 10320
gtaaaaagac gcggactcat gtgaaatact ggttttttagt gcgccagatc tctataatct 10380
cgcgcaacct attttcccct cgaacacttt ttaagccgta gataaacagg ctggacact 10440
tcacatgagc gaaaaataca tcgtcacctg ggacatgttg cagatccatg cacgtaaact 10500
cgcaagccga ctgatgcctt ctgaacaatg gaaaggcatt attgccgtaa gccgtggcgg 10560
tctgtaccgg gtcgttact ggcgcggtga ctgggtattc gtcatgtcga taccgtttgt 10620
atttccagct acgatcacga caaccagcgc gagcttaaag tgctgaaacg cgcagaaggc 10680
gatgcgaag gcttcatcgt tattgatgac ctggtggata ccggtggtac tgcggttgcg 10740
attcgtgaaa tgtatccaaa agcgcacttt gtcaccatct tcgcaaaacc ggctggtcgt 10800
ccgctggttg atgactatgt tgttgatatc ccgcaagata cctggattga acagccgtgg 10860
gatatggcg tcgtattcgt cccgccaatc tccggtcgct aatcttttca acgcctggca 10920
ctgccgggcg ttgttctttt taacttcagg cgggttacaa tagtttccag taagtattct 10980
ggaggctgca tccatgacac aggcaaacct gagcgaaacc ctgttcaaac cccgctttaa 11040
acatcctgaa acctcgacgc tagtccgccg ctttaatcac ggcgcacaac cgcctgtgca 11100
gtcggccctt gatggtaaaa ccatccctca ctggtatcgc atgattaacc gtctgatgtg 11160
gatctggcgc ggcattgacc cacgcgaaat cctcgacgtc caggcacgta ttgtgatgag 11220
cgatgccgaa cgtaccgacg atgatttata cgatacggtg attggctacc gtggcggcaa 11280
ctggatttat gagtgggccc cggatctttg tgaaggaacc ttacttctgt ggtgtgacat 11340
aattggacaa actacctaca gagatttaaa gctctaaggt aaatataaaa tttttaaccc 11400
ggatctttgt gaaggaacct tacttctgtg gtgtgacata attggacaaa ctacctacag 11460
agatttaaag ctctaaggta aatataaaat ttttaagtgt ataatgtgtt aaactactga 11520
ttctaattgt ttgtgtattt tagattccaa cctatggaac tgatgaatgg gagcagtggt 11580
ggaatgcctt taatgaggaa aacctgtttt gctcagaaga atgccatct agtgatgatg 11640
aggctactgc tgactctcaa cattctactc tccaaaaaa gaagagaaag gtagaagacc 11700
ccaaggactt tccttcagaa ttgctaagtt ttttgagtca tgctgtgttt agtaatgaaa 11760
ctcttgcttg ctttgctatt tacaccacaa aggaaaaagc tgcactgcta tacaagaaaa 11820
```

```
ttatggaaaa atattctgta acctttataa gtaggcataa cagtatataat cataacatac    11880
tgttttttct tactccacac aggcatagag tgtctgctat taataactat gctcaaaaat    11940
tgtgtacctt tagctttta atttgtaaag gggttaataa ggaatatttg atgtatagtg    12000
ccttgactag agatcataat cagccatacc acatttgtag aggttttact tgctttaaaa    12060
aacctcccac acctcccct gaacctgaaa cataaaatga atgcaattgt tgttgttggg    12120
ctgcaggaat taattcgagc tcgcccgaca                                      12150
```

SEQ ID NO: 34          moltype = DNA   length = 10627
FEATURE                Location/Qualifiers
misc_feature           1..10627
                       note = Synthetic encoding HIV-1 GAG-CAS9 construct
misc_feature           1..10627
                       note = encoding HIV-1 GAG-CAS9 construct
source                 1..10627
                       mol_type = other DNA
                       organism = synthetic construct SEQUENCE: 34
```
gcggccgctc tagagagctt ggcccattgc atacgttgta tccatatcat aatatgtaca    60
tttatattgg ctcatgtcca acattaccgc catgttgaca ttgattattg actagttatt    120
aatagtaatc aattacgggg tcattagttc atagcccata tatggagttc cgcgttacat    180
aacttacggt aaatggcccg cctggctgac cgcccaacga ccccgccca ttgacgtcaa    240
taatgacgta tgttcccata gtaacgccaa tagggactt ccattgacgt caatgggtgg    300
agtatttacg gtaaactgcc cacttggcag tacatcaagt gtatcatatg ccaagtacgc    360
ccctattga cgtcaatgac ggtaaatggc ccgcctggca ttatgcccag tacatgacct    420
tatgggactt tcctacttgg cagtacatct acgtattagt catcgctatt accatggtga    480
tgcggttttg gcagtacatc aatgggcgtg gatagcggtt tgactcacgg ggatttccaa    540
gtctccaccc cattgacgtc aatgggagtt tgttttggca ccaaaatcaa cgggactttc    600
caaaatgtcg taacaactcc gccccattga cgcaaatggg cggtaggcgt gtacggtggg    660
aggtctatat aagcagagct cgtttagtga accgtcagat cgcctggaga cgccatccac    720
gctgttttga cctccataga agacaccggg accgatccga cctccggtcg accgatcctg    780
agaacttcag ggtgagtttg ggacccttgc attgttcttt ctttttcgct attgtaaaat    840
tcatgttata tggagggggc aaagttttca gggtgttgtt agaatgggaa gatgtccct    900
tgtatccaca tggacccctca tgataatttt tgtttctttca cttctactcc tgttgacaac    960
cattgctcc tcttatttc ttttcatttt cttgtaactt tttcgttaatn ctttagcttg    1020
catttgtaac gaatttttaa attcacttttt gtttattgttt cagattgtaa gtactttctc    1080
taatcacttt tttttcaagg caatcagggt atattatatt gtacttcagc acagttttag    1140
agaacaattg ttataattaa atgataaggt agaatatttc tgcatataaa ttctggctgg    1200
cgtggaaata ttcttattgg tagaaacaac tacatcctgg tcatcatcct gccttttctc    1260
ttatggttac aatgatatac actgtttgag atgaggataa aatactctga gtccaaaccg    1320
ggccctctg ctaaccatgt tcatgccttc tctttttttc ttacagctct ggcaacgtg    1380
ctggttattg tgctgtctca tcatttggc aaagaattcc tcgagatggg tgcgagagcg    1440
tcggtattaa gcggggagaa attagataaa tgggaaaaaa ttcggttaag gccagggggaa    1500
aagaaacaat ataaactaa acatatagta tgggcaagca gggagctaga acgattcgca    1560
gttaatcctg gccttttaga gacatcagaa ggctgtagac aaatactggg acagctacaa    1620
ccatccccttc agacaggatc agaagaactt agatcattat ataatacaat agcagtcctc    1680
tattgtgtgc atcaaaggat agatgtaaaa gacaccaagg aagccttaga taagatagag    1740
gaagagcaaa acaaaagtaa gaaaaaggca cagcaagca cagctgacac aggaaacaac    1800
agccaggtca gccaaaatta cccctatagt cagaacctcc aggggcaaat ggtacatcag    1860
gccatatcac ctagaacttt aaatgcatgg gtaaaagtag tagaagagaa ggcttttcagc    1920
ccagaagtaa tacccatgtt ttcagcatta tcagaaggag ccaccccaca agatttaaat    1980
accatgctaa acacagtggg gggacatcaa gcagccatgc aaatgttaaa agagaccatc    2040
aatgaggaag ctgcagaatg ggatagattg catccagtgc atgcagggcc tattgcacca    2100
ggccagatga gagaaccaag gggaagtgac atagcaggaa ctactagtac ccttcaggaa    2160
caaataggat ggatgacaca taatccacct atcccagtag gagaaatcta taaaagatgg    2220
ataatcctgg gattaaataa aatagtaaga atgtatagcc ctaccagcat tctggacata    2280
agacaaggac caaaggaacc ctttagagac tatgtagacc gattctataa aactctaaga    2340
gccgagcaag cttcacaaga ggtaaaaaat tggatgacag aaaccttgtt ggtccaaaat    2400
gcgaacccag attgtaagac tattttaaaa gcattgggac caggagcgac actagaagaa    2460
atgatgacag catgtcaggg agtgggggga cccggccata aggcaagagt tttggctgaa    2520
gcaatgagcc aagtaacaaa tccagctacc ataatgatac agaaaggcaa ttttaggaac    2580
caaagaaaga ctgttaagtg tttcaattgt ggcaaagaag gcacatagcc aaaaattgc    2640
agggccccta ggaaaaaggg ctgttggaaa tgtggaaagg aaggacacca aatgaaagat    2700
tgtactgaga gacaggctaa ttttttaggg aagatctggc cttcccacaa gggaaggcca    2760
gggaatttc ttcagagcag accagagcca acagccccca cagaagagct tccaggtttt    2820
ggggaagaga caacaactcc ctctcagaag caggagccga tagacaagga actgtatcct    2880
ttagcttccc tcagatcact ctttggcagc gaccctcgt cacaaccggg gaccacgacc    2940
ccaggcaaag caagagtttt ggctgaagca atgagcaccg tgattacaa agacgatgac    3000
gataagatgg cccaaagaa gaagcggaag gtcggtatcc acggagtccc agcagccgac    3060
aagaagtaca gcatcggcct ggacatcggc accaactctg tgggctggc cgtgatcacc    3120
gacgagtaca aggtgcccag caagaaattc aaggtgctgg gcaacaccga ccggcacagc    3180
atcaagaaga acctgatcgg agccctgctg ttcgacagcg gcgaaacagc cgaggccacc    3240
cggctgaaga gaaccgccag aagaagatac accagacgga agaaccggat ctgctatctg    3300
caagagatct tcagcaacga gatggccaag gtggacgaca gcttcttcca cagactggaa    3360
gagtccttcc tggtggaaga ggataagaag cacgagcggc accccatctt cggcaacatc    3420
gtggacgagg tggcctacca cgagaagtac cccaccatct accacctgag aaagaaactg    3480
gtggacagca ccgacaaggc cgacctgcgg ctgatctatc tggcccctgc ccacatgatc    3540
aagttccggg gccacttcct gatcgagggc gacctgaacc cggacaacag cgacgtggac    3600
aagctgttca tccagctggt gcagacctac aaccagctgt tcgaggaaaa ccccatcaac    3660
gccagcggcg tggacgccaa ggccatcctg tctgccgaca ctgagcaagag cagacggctg    3720
```

```
gaaaatctga tcgcccagct gcccggcgag aagaagaatg gcctgttcgg caacctgatt   3780
gccctgagcc tgggcctgac ccccaacttc aagagcaact tcgacctggc cgaggatgcc   3840
aaactgcagc tgagcaagga cacctacgac gacgacctgg acaacctgct ggcccagatc   3900
ggcgaccagt acgccgacct gtttctggcc gccaagaacc tgtccgacgc catcctgctg   3960
agcgacatcc tgagagtgaa caccgagatc accaaggccc ccctgagcgc ctctatgatc   4020
aagagatacg acgagcacca ccaggacctg accctgctga agctctcgt gcggcagcag   4080
ctgcctgaga agtacaaaga gattttcttc gaccagagca gaacggcta cgccggctac   4140
attgacggcg gagccagcca ggaagagttc tacaagttca tcaagcccat cctggaaaag   4200
atggacggca ccgaggaact gctcgtgaag ctgaacagag aggacctgct gcggaagcca   4260
cggaccttcg acaacggcag catccccac cagatccacc tgggagagct gcacgccatt   4320
ctgcggcggc aggaagattt tacccattc ctgaaggaca accggaaaa gatcgagaag   4380
atcctgacct tccgcatccc ctactacgtg gccctctgg ccaggggaaa cagcagattc   4440
gcctggatga ccagaaagag cgaggaaacc atcaccccct ggaacttcga ggaagtggtg   4500
gacaagggcg cttccgccca gagcttcatc gagcggatga ccaacttcga taagaacctg   4560
cccaacgaga aggtgctgcc caagcacagc ctgctgtacg agtacttcac cgtgtataac   4620
gagctgacca aagtgaaata cgtgaccgag ggaatgagaa agcccgcctt cctgagcggc   4680
gagcagaaaa aggccatcgt ggacctgctg ttcaagacca ccggaaagt gaccgtgaag   4740
cagctgaaag aggactactt caagaaaatc gagtgcttcg actccgtgga aatctccggc   4800
gtggaagatc ggttcaacgc ctccctgggc acataccacg atctgctgaa aattatcaag   4860
gacaaggact tcctggacaa tgaggaaaac gaggacattc tggaagatat cgtgctgacc   4920
ctgacactgt ttgaggacag agagatgatc gaggaacggc tgaaaccta tgcccacctg   4980
ttcgacgaca aagtgatgaa gcagctgaag cggcggagat acaccggctg gggcaggctg   5040
agccggaagc tgatcaacgg catccggac aagcagtccg gcaagacaat cctggatttc   5100
ctgaagtccg acggcttcgc caacagaaac ttcatgcagc tgatccacga cgacagcctg   5160
accttaaag aggacatcca gaaagcccag gtgtccggcc agggcgatag cctgcacgag   5220
cacattgcca atctggccgg cagccccgcc attaagaagg gcatcctgca gacagtgaag   5280
gtggtggacg agctcgtgaa agtgatgggc cggcacaagc ccgagaacat cgtgatcgaa   5340
atggccagag agaaccagac cacccagaag ggacagaaga cagccgcga gagaatgaag   5400
cggatcgaag agggcatcaa agagctgggc agccagatcc tgaagaaaca ccccgtggaa   5460
aacacccgac tgcagaacga gaagctgtac ctgtactacc tgcagaatgg gcgggatatg   5520
tacgtggacc aggaactgga catcaaccgg ctgtccgact acgatgtgga ccatatcgtg   5580
cctcagagct ttctgaagga cgactccatc gacaacaagg tgctgaccag aagcgacaag   5640
aaccggggca gagcgacaa cgtgcccct gaagaggtcg tgaagaagat gaagaactac   5700
tggcggcaac tgctgaacgc caagctgatt acccagaga agttcgacaa tctgaccaag   5760
gccgagagag gcggcctgag cgaactggat aaggccggct tcatcaagag acagctggtg   5820
gaaacccggc agatcacaaa gcacgtggca cagatcctgg actccggat gaacactaag   5880
tacgacgaga atgacaagct gatccgggaa gtgaaagtga tcaccctgaa gtccaagctg   5940
gtgtccgatt ccggaagga tttccagttt tacaaagtgc gcgagatcaa caactaccac   6000
cacgcccacg acgcctacct gaacgccgtc gtgggaaccg ccctgatcaa aaagtaccct   6060
aagctggaaa gcgagttcgt gtacggcgac tacaaggtgt acgacgtgcg gaagatgatc   6120
gccaagagcg agcaggaaat cggcaaggct accgccaagt acttcttcta cagcaacatc   6180
atgaactttt tcaagaccga gattaccctg gccaacggcg agatccggaa gcggcctctg   6240
atcgagacaa acggcgaaac cggggagatc gtgtgggata aggccggaa ttttgccctg   6300
gtgcggaaag tgctgagcat gccccaagtg aatatcgtga aaagaccga ggtgcagaca   6360
ggcggcttca gcaaagagtc tatcctgccc aagaggaaca gcgataagct gatcgccaga   6420
aagaaggact gggaccctaa gaagtacggc ggcttcgaca gccccaccgt ggcctattct   6480
gtgctggtgg tggccaaagt ggaaaagggc aagtccaaga aactgaagag tgtgaaagag   6540
ctgctgggga tcaccatcat ggaaagaagc agcttcgaga gaatccat cgactttctg   6600
gaagccaagg gctacaaaga agtgaaaaag gacctgatca tcaagctgcc taagtactcc   6660
ctgttcgagc tggaaaacgg ccggaagaga atgctggcct ctgccggcga actgcagaag   6720
ggaaacgaac tggcccctgcc ctccaaatat gtgaacttcc tgtacctgcc cagccactat   6780
gagaagctga agggctcccc cgaggataat gagcagaaac agctgtttgt ggaacagcac   6840
aagcactacc tggacgagat catcgagcag atcagcgagt ctccaagag agtgatcctg   6900
gccgacgcta tctggacaa agtgctgtcc gcctacaaca gcaccggga taagcccatc   6960
agagacaagg ccgagaatat catccacctg tttacctga ccaatctggg agccctgc   7020
gccttcaagt actttgacac caccatcgac cggaagaggt acaccagcac caaagaggtg   7080
ctggacgcca ccctgatcca ccagagcatc accggcctgt acgagacacg gatcgacctg   7140
tctcagctgg gaggcgacaa gcgtcctgct gctactaaga agctggtca agctaagaaa   7200
aagaaagcta gagcttgata tcctgcagac gcgtaggatc cgtcgaggaa ttcactcctc   7260
aggtgcaggc tgcctatcag aaggtggtgg ctggtgtggc caatgccctg gctcacaaat   7320
accactgaga tcttttttccc tctgccaaaa attatgggga catcatgaag ccccttgagc   7380
atctgacttc tggctaataa aggaaattta ttttcattgc aatagtgtgt tggaattttt   7440
tgtgtctctc actcggaagg acatatggga gggcaaatca tttaaaacat cagaatgagt   7500
atttggttta gagtttggca acatatgccc atatgctggc tgcatgaac aaagtttgga   7560
tataaagagg tcatcagtat atgaaacagc cccctgctgt ccattccta ttccatagaa   7620
aagccttgac ttgaggttag atttttttta tattttgttt tgtgttattt ttttctttaa   7680
catccctaaa atttttcctta catgttttac tagccagatt tttcctcctc tcctgactac   7740
tcccagtcat agctgtccct cttctcttat ggagatccct cgcctgatcg gccgcaattc   7800
gtaatcatgt catagctgtt tcctgtgtga aattgttatc cgctcacaat tccacacaac   7860
atacgagccg gaagcataaa gtgtaaagcc tggggtgcct aatgagtgag ctaactcaca   7920
ttaattgcgt tgcgctcact gcccgctttc cagtcgggaa acctgtcgtg ccagctgcat   7980
taatgaatcg gccaacgcgc ggggagaggc ggtttgcgta ttgggcgctc ttccgcttcc   8040
tcgctcactg actcgctgcg ctcggtcgtt cggctgcggc gagcggtatc agctcactca   8100
aaggcggtaa tacggttatc cacagaatca ggggataacg caggaaagaa catgtgagca   8160
aaaggccagc aaaaggccag gaaccgtaaa aaggccgcgt tgctggcgtt tttccatagg   8220
ctccgccccc ctgacgagca tcacaaaaat cgacgctcaa gtcagaggtg gcgaaacccg   8280
acaggactat aaagatacca ggcgtttccc cctggaagct ccctcgtgcg ctctcctgtt   8340
ccgaccctgc cgcttaccgg atacctgtcc gcctttctcc cttcgggaag cgtggcgctt   8400
tctcatagct cacgctgtag gtatctcagt tcggtgtagg tcgttcgctc caagctgggc   8460
```

-continued

```
tgtgtgcacg aacccccgt tcagcccgac cgctgcgcct tatccggtaa ctatcgtctt  8520
gagtccaacc cggtaagaca cgacttatcg ccactggcag cagccactgg taacaggatt  8580
agcagagcga ggtatgtagg cggtgctaca gagttcttga agtggtggcc taactacggc  8640
tacactagaa gaacagtatt tggtatctgc gctctgctga agccagttac cttcggaaaa  8700
agagttggta gctcttgatc cggcaaacaa accaccgctg gtagcggtgg ttttttgttt  8760
tgcaagcagc agattacgcg cagaaaaaaa ggatctcaag aagatccttt gatcttttct  8820
acggggtctg acgctcagtg gaacgaaaac tcacgttaag ggattttggt catgagatta  8880
tcaaaaagga tcttcaccta gatcctttta aattaaaaat gaagttttaa atcaatctaa  8940
agtatatatg agtaaacttg gtctgacagt taccaatgct taatcagtga ggcacctatc  9000
tcagcgatct gtctatttcg ttcatccata gttgcctgac tccccgtcgt gtagataact  9060
acgatacggg agggcttacc atctggcccc agtgctgcaa tgataccgcg agacccacgc  9120
tcaccggctc cagatttatc agcaataaac cagccagccg gaagggccga gcgcagaagt  9180
ggtcctgcaa ctttatccgc ctccatccag tctattaatt gttgccggga agctagagta  9240
agtagttcgc cagttaatag tttgcgcaac gttgttgcca ttgctacagg catcgtggtg  9300
tcacgctcgt cgtttggtat ggcttcattc agctccggtt cccaacgatc aaggcgagtt  9360
acatgatccc ccatgttgtg caaaaaagcg gttagctcc ttcggtcctc cgatcgttgt  9420
cagaagtaag ttggccgcag tgttatcact catggttatg gcagcactgc ataattctct  9480
tactgtcatg ccatccgtaa gatgcttttc tgtgactggt gagtactcaa ccaagtcatt  9540
ctgagaatag tgtatgcggc gaccgagttg ctcttgcccg gcgtcaatac gggataataac  9600
cgcgccacat agcagaactt taaaagtgct catcattgga aaacgttctt cggggcgaaa  9660
actctcaagg atcttaccgc tgttgagatc cagttcgatg taacccactc gtgcacccaa  9720
ctgatcttca gcatctttta cttttcaccag cgtttctgg tgagcaaaaa caggaaggca  9780
aaatgccgca aaaagggaa taagggcgac acgaaatgt tgaatactca tactcttcct  9840
ttttcaatat tattgaagca tttatcaggg ttattgtctc atgagcggat acatatttga  9900
atgtatttag aaaaataaac aaataggggt tccgcgcaca tttccccgaa aagtgccacc  9960
taaattgtaa gcgttaatat tttgttaaaa ttcgcgttaa attttgtta aatcagctca 10020
tttttttaacc aataggccga atcggcaaa atcccttata aatcaaaaga atagaccgag 10080
atagggttga gtgttgttcc agtttggaac aagagtccac tattaaagaa cgtggactcc 10140
aacgtcaaag ggcgaaaaac cgtctatcag ggcgatggcc cactacgtga accatcaccc 10200
taatcaagtt ttttgggtc gaggtgccgt aaagcactaa atcggaaccc taaagggagc 10260
ccccgattta gagcttgacg gggaaagccg gcgaacgtgg cgagaaagga gggaagaaa 10320
gcgaaaggag cgggcgctag ggcgctggca agtgtagcgg tcacgctgcg cgtaaccacc 10380
acacccgccg cgcttaatgc gccgctacag ggcgcgtccc attcgccatt caggctgcgc 10440
aactgttggg aagggcgatc ggtgcgggcc tcttcgctat tacgccagct ggcgaaaggg 10500
ggatgtgctg caaggcgatt aagttgggta acgccaggt ttcccagtc acgacgttgt 10560
aaaacgacgg ccagtgagcg cgcgtaatac gactcactat agggcgaatt ggagctccac 10620
cgcggtg                                                          10627

SEQ ID NO: 35           moltype = DNA  length = 20
FEATURE                 Location/Qualifiers
misc_feature            1..20
                        note = Synthetic GFP target sequence
misc_feature            1..20
                        note = GFP target sequence
source                  1..20
                        mol_type = other DNA
                        organism = synthetic construct
SEQUENCE: 35
cgaggagctg ttcaccgggg                                                20

SEQ ID NO: 36           moltype = DNA  length = 27
FEATURE                 Location/Qualifiers
misc_feature            1..27
                        note = Synthetic primer
source                  1..27
                        mol_type = other DNA
                        organism = synthetic construct
SEQUENCE: 36
attgcggaag ttcctcttct taccctg                                        27

SEQ ID NO: 37           moltype = DNA  length = 27
FEATURE                 Location/Qualifiers
misc_feature            1..27
                        note = Synthetic primer
source                  1..27
                        mol_type = other DNA
                        organism = synthetic construct
SEQUENCE: 37
ttcctgggaa gggtggatta tgacggg                                        27

SEQ ID NO: 38           moltype = DNA  length = 20
FEATURE                 Location/Qualifiers
misc_feature            1..20
                        note = Synthetic target sequence
source                  1..20
                        mol_type = other DNA
                        organism = synthetic construct
SEQUENCE: 38
cgaggagctg ttcaccgggg                                                20
```

```
SEQ ID NO: 39          moltype = DNA  length = 23
FEATURE                Location/Qualifiers
misc_feature           1..23
                       note = Synthetic primer
source                 1..23
                       mol_type = other DNA
                       organism = synthetic construct
SEQUENCE: 39
tctgagtggc aaaggaccttt agg                                              23

SEQ ID NO: 40          moltype = DNA  length = 26
FEATURE                Location/Qualifiers
misc_feature           1..26
                       note = Synthetic primer
source                 1..26
                       mol_type = other DNA
                       organism = synthetic construct
SEQUENCE: 40
gaagtcgtgc tgcttcatgt ggtcgg                                            26
```

METHODS AND PRODUCTS FOR GENETIC ENGINEERING

CROSS REFERENCE TO RELATED APPLICATIONS

This application is a continuation of Non-Provisional application Ser. No. 18/130,375, filed Apr. 3, 2023, which is a continuation of Non-Provisional Ser. No. 17/174,405, filed Feb. 12, 2021, now issued as U.S. Pat. No. 11,649,264, which is a continuation of Non-Provisional application Ser. No. 15/769,534, filed Apr. 19, 2018, now issued as U.S. Pat. No. 10,968,253, which is a National Stage application under 35 U.S.C. § 371 of International Application No. PCT/EP2016/075289, filed on Oct. 20, 2016, which claims priority to European Provisional Application No. 15306678, filed Oct. 20, 2015, the contents of which are incorporated herein by reference in their entirety.

REFERENCE TO AN ELECTRONIC SEQUENCE LISTING

The contents of the electronic sequence listing (186152001303SEQLIST.xml; Size: 107,664 bytes; and Date of Creation: Nov. 22, 2023) is herein incorporated by reference in its entirety.

FIELD OF THE INVENTION

The present invention relates to the field of gene targeting by methods using viral-derived vector systems related to Clustered Regularly Interspaced Short Palindromic Repeats (CRISPR) and components thereof.

BACKGROUND OF THE INVENTION

Genome editing using targetable nucleases is an emerging technology for the precise genome modification of organisms ranging from bacteria to plants and animals, including humans. Its attraction is that it can be used for almost all organisms in which targeted genome modification has not been possible with other kinds of methods.

Improving protocols for expressing exogenous proteins within human cells is of major interest for research and medical purposes. In spite of the constant evolution of transfection methods and performances of viral vectors, the efficiency of these approaches can vary dramatically, especially in primary cells that are highly sensitive to modifications of their environment and may be altered in response to transfection agents/vectors. Moreover, delivering genetic information through the transfer of a coding integrative/non-integrative DNA may be responsible for adverse effects like the induction of unwanted stress signals or the unexpected insertion of an exogenous gene within the cellular genome, which is a serious issue for therapeutic applications, particularly in stem cells.

Recent approaches to targeted genome modification—zinc-finger nucleases (ZFNs) and transcription-activator like effector nucleases (TALENs)—have enabled researchers to generate permanent mutations by introducing double-stranded breaks to activate repair pathways. The capacity of designed nucleases, like ZFN and TALENs, to generate DNA double-stranded breaks at desired positions in the genome has created optimism for therapeutic translation of locus-directed genome engineering. However, these approaches are costly and time-consuming to engineer, limiting their widespread use, particularly for large scale, high-throughput studies.

More recently, a new tool based on a totally distinct and specific system, namely bacterial CRISPR-associated protein-9 nuclease (Cas9) from *Streptococcus pyogenes* has generated considerable interest.

To achieve site-specific DNA recognition and cleavage, Cas9 must be complexed with both a crRNA and a separate trans-activating crRNA (tracrRNA or trRNA), that is partially complementary to the crRNA (11). The tracrRNA is required for crRNA maturation from a primary transcript encoding multiple pre-crRNAs.

During the cleavage of target DNA, the HNH and RuvC-like nuclease domains cut both DNA strands, generating double-stranded breaks (DSBs) at sites defined by a 20-nucleotide guide sequence within an associated crRNA transcript that base pairs with the target DNA sequence. The HNH domain cleaves the target DNA strand that is complementary to the guide RNA, while the RuvC domain cleaves the non-complementary strand. The double-stranded endonuclease activity of Cas9 also requires that a short conserved sequence, (2-5 nts) known as protospacer-associated motif (PAM), follows immediately 3'- of the crRNA complementary sequence.

The simplicity of the type II CRISPR nuclease, with only three required components (Cas9 along with the crRNA and trRNA) made this system amenable to adaptation for genome editing. This potential was realized in 2012 by the Doudna and Charpentier laboratories (Jinek et al., 2012, Science, Vol. 337: 816-821). Based on the type II CRISPR system described previously, a simplified two-component system was developed by combining trRNA and crRNA into a single synthetic single guide RNA (sgRNA). The sgRNA-programmed Cas9 was shown to be as effective as Cas9 programmed with separate trRNA and crRNA in guiding targeted gene alterations.

Mainly, three different variants of the Cas9 nuclease have been adopted in genome-editing protocols. The first is wild-type Cas9, which can site-specifically cleave double-stranded DNA, resulting in the activation of the double-strand break (DSB) repair machinery. DSBs can be repaired by the cellular Non-Homologous End Joining (NHEJ) pathway (Overballe-Petersen et al., 2013, Proc Natl Acad Sci USA, Vol. 110: 19860-19865), resulting in insertions and/or deletions (indels) which disrupt the targeted locus. Alternatively, if a donor template with homology to the targeted locus is supplied, the DSB may be repaired by the homology-directed repair (HDR) pathway allowing for precise replacement mutations to be made (Overballe-Petersen et al., 2013, Proc Natl Acad Sci USA, Vol. 110: 19860-19865; Gong et al., 2005, Nat. Struct Mol Biol, Vol. 12: 304-312).

Cong and colleagues (Cong et al., 2013, Science, Vol. 339: 819-823) took the Cas9 system a step further towards increased precision by developing a mutant form, known as Cas9D10A, with only nickase activity. This means that Cas9D10A cleaves only one DNA strand, and does not activate NHEJ. Instead, when provided with a homologous repair template, DNA repairs are conducted via the high-fidelity HDR pathway only, resulting in reduced indel mutations (Cong et al., 2013, Science, Vol. 339: 819-823; Jinek et al., 2012, Science, Vol. 337: 816-821; Qi et al., 2013 Cell, Vol. 152: 1173-1183). Cas9D10A is even more appealing in terms of target specificity when loci are targeted by paired Cas9 complexes designed to generate adjacent DNA nicks (Ran et al., 2013, Cell, Vol. 154: 1380-1389).

The third variant is a nuclease-deficient Cas9 (Qi et al., 2013 Cell, Vol. 152: 1173-1183). Mutations H840A in the HNH domain and D10A in the RuvC domain inactivate cleavage activity, but do not prevent DNA binding. Therefore, this variant can be used to target in a sequence-specific manner any region of the genome without cleavage. Instead, by fusing with various effector domains, dCas9 can be used either as a gene silencing or activation tools. Furthermore, it can be used as a visualization tool by coupling the guide RNA or the Cas9 protein to a fluorophore or a fluorescent protein.

Following its initial demonstration in 2012 (9), the CRISPR/Cas9 system has been widely adopted by the scientific community. It has already been successfully used to target important genes in many cell lines and organisms, including human (Mali et al., 2013, Science, Vol. 339: 823-826), bacteria (Fabre et al., 2014, PLoS Negl. Trop. Dis., Vol. 8:e2671), zebrafish (Hwang et al., 2013, PLoS One, Vol. 8:e68708), *C. elegans* (Hai et al., 2014 Cell Res. doi: 10.1038/cr.2014.11), bacteria (Fabre et al., 2014, PLoS Negl. Trop. Dis., Vol. 8:e2671), plants (Mali et al., 2013, Science, Vol. 339: 823-826), *Xenopus tropicalis* (Guo et al., 2014, Development, Vol. 141: 707-714), yeast (DiCarlo et al., 2013, Nucleic Acids Res., Vol. 41: 4336-4343), *Drosophila* (Gratz et al., 2014 Genetics, doi: 10.1534/genetics.113.160713), monkeys (Niu et al., 2014, Cell, Vol. 156: 836-843), rabbits (Yang et al., 2014, J. Mol. Cell Biol., Vol. 6: 97-99), pigs (Hai et al., 2014, Cell Res. doi: 10.1038/cr.2014.11), rats (Ma et al., 2014, Cell Res., Vol. 24: 122-125) and mice (Mashiko et al., 2014, Dev. Growth Differ. Vol. 56: 122-129). Several groups have now taken advantage of this method to introduce single point mutations (deletions or insertions) in a particular target gene, via a single gRNA. Using a pair of gRNA-directed Cas9 nucleases instead, it is also possible to induce large deletions or genomic rearrangements, such as inversions or translocations. A recent exciting development is the use of the dCas9 version of the CRISPR/Cas9 system to target protein domains for transcriptional regulation, epigenetic modification, and microscopic visualization of specific genome loci.

The CRISPR/Cas9 system requires only the redesign of the crRNA to change target specificity. This contrasts with other genome editing tools, including zinc finger and TALENs, where redesign of the protein-DNA interface is required. Furthermore, CRISPR/Cas9 enables rapid genome-wide interrogation of gene function by generating large gRNA libraries for genomic screening.

Thus, the CRISPR/Cas9 technology can be easily adapted to any gene of interest and may offer unchallenged possibilities to alter genes (knock-out, knock-in, introduction of precise mutations). Its spread in the scientific community is amazingly rapid and has triggered a recent burst of scientific communications using it.

CRISPR's delivery is commonly performed by DNA transfection or through the use of viral vectors encoding Cas9, both methods being convenient but limited to certain cell types as well as being rather intrusive. Furthermore, maintenance of Cas9 expression for a long period is possibly toxic and at best not necessary, since Cas9-mediated cleavage occurs rapidly (Jinek et al., 2013, eLife, Vol. 2, e00471) and could even be toxic on long term. Other approaches have succeeded in exploiting recombinant Cas9 and synthetic RNAs to transfer the RNPc by Proteo transfection or by physical microinjection but these CRISPRs systems remain limited to target fragile primary cells.

There is a need in the art for improved tools and methods for gene editing by using CRISPR/Cas technology.

SUMMARY OF THE INVENTION

The present invention relates to products and methods for generating alterations in genomic nucleic acids; which alterations encompass mutations by introduction of nucleic acid insertion and nucleic acid deletion, which include knock-in and knock-out genomic alterations.

More precisely, this invention relates to products aimed at generating nucleic acid alteration events caused by CRISPR-Cas complexes, and especially caused by CRISPR-Cas9 complexes, as well as to methods using the same.

This invention relates to a virus-derived particle comprising one or more Cas protein(s), and especially Cas9 protein.

In some embodiments, the said virus-derived particle further comprises, or is further complexed with, one or more CRISPR-Cas system guide RNA(s).

In some embodiments, the said virus-derived particle further comprises, or is further complexed with a targeting nucleic acid.

In some embodiments, the said virus-derived particle is a retrovirus-derived particle, e.g. a lentivirus-derived vector particle.

This invention further pertains to a composition for altering a target nucleic acid in a eukaryotic cell, which composition comprises a virus-derived particle comprising one or more Cas protein(s), and especially Cas9 protein.

In some embodiments, the said composition further comprises, or alternatively is further complexed with, one or more CRISPR-Cas system guide RNA(s).

In some embodiments, the said composition further comprises a targeting nucleic acid.

This invention also concerns a kit comprising the required substances for preparing a virus-derived particle or a composition as defined above.

It also relates to genetically modified cells producing virus-derived particles as defined herein, especially cells which are under the form of stable cell lines.

This invention further relates to a fusion protein comprising (i) a viral protein that self assembles for generating a virus-derived particle, the said viral protein being fused to (ii) a Cas protein. In some embodiments, the said fusion protein comprises a cleavable site located between the said viral protein and the said Cas protein, and especially a cleavable site located between a Gag protein and a Cas9 protein.

It also pertains to nucleic acids and vector encoding the said fusion protein.

BRIEF DESCRIPTION OF THE DRAWINGS

FIG. 1A-FIG. 1B: Molecular Basis of Cas9-VLP assembly and transfer of CRISPRs-components into recipient cells.

FIG. 1A: Schematic representation of Cas9-VLPs assembly from HEK293T cells. 6 Steps are depicted:

(1) GAG-CAS9, GAG ProPol and a viral envelope protein are transfected in HEK293T cells in association with a construct encoding a guide RNA. GAG and the viral envelope tend to localize at the membrane where the assembly of a virus-derived particle (which may be also termed "Virus-Like Particle" or "VLP" herein) takes place (2). As concentration of GAG increases, mechanical forces induce the formation of a particle (3) that will bud from the producer cell after having incorporated all the actors of the CRISPR machinery (4). These particles can be concentrated and are stable at 4° C. more than 15 days. Due to the maturation process, the viral protease may have released most Cas9 proteins from the GAG platform within the particle (5). Exposed to target cells, VLPs will be able to bind and fuse the with cell membrane through an envelope/receptor interaction that thus depends on the envelope used to pseudotype particles and the considered target cell. After fusion with the cellular membrane, VLPs transfer their cargo within recipient cells which may include Cas9/gRNAs ribonucleocomplexes, free gRNAs or Cas9 possibly associated with non-protease GAG (not yet clarified). Fully active CRISPRs RNPc are nevertheless delivered into the nucleus of recipient cells (possibly due to a re-association of Cas9 and free gRNAs within the target cell) and mediate the cleavage of genomic-DNA in the very position specified by the gRNA (6).

Figure 1B:
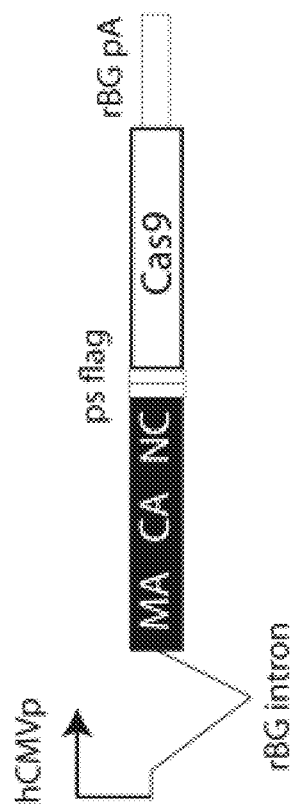

FIG. 1B: Molecular Design of the GAG-Cas9 coding construct. hCMVp (human cytomegalovirus early promoter) drives the expression of a mRNA incorporating an intron (rBG) and a poly adenylation (rBGpA) signal both deriving from the rabbit beta globin gene sequence. The construct consists of the fusion of the MLV-GAG polyprotein with the codon-optimized Cas9 sequence from *Streptococcus pyogenes*. Both moieties are separated by a MLV protease cleavage site (ps) and a flag-tag sequence fused to the Cas9 sequence.

Figure 2A:
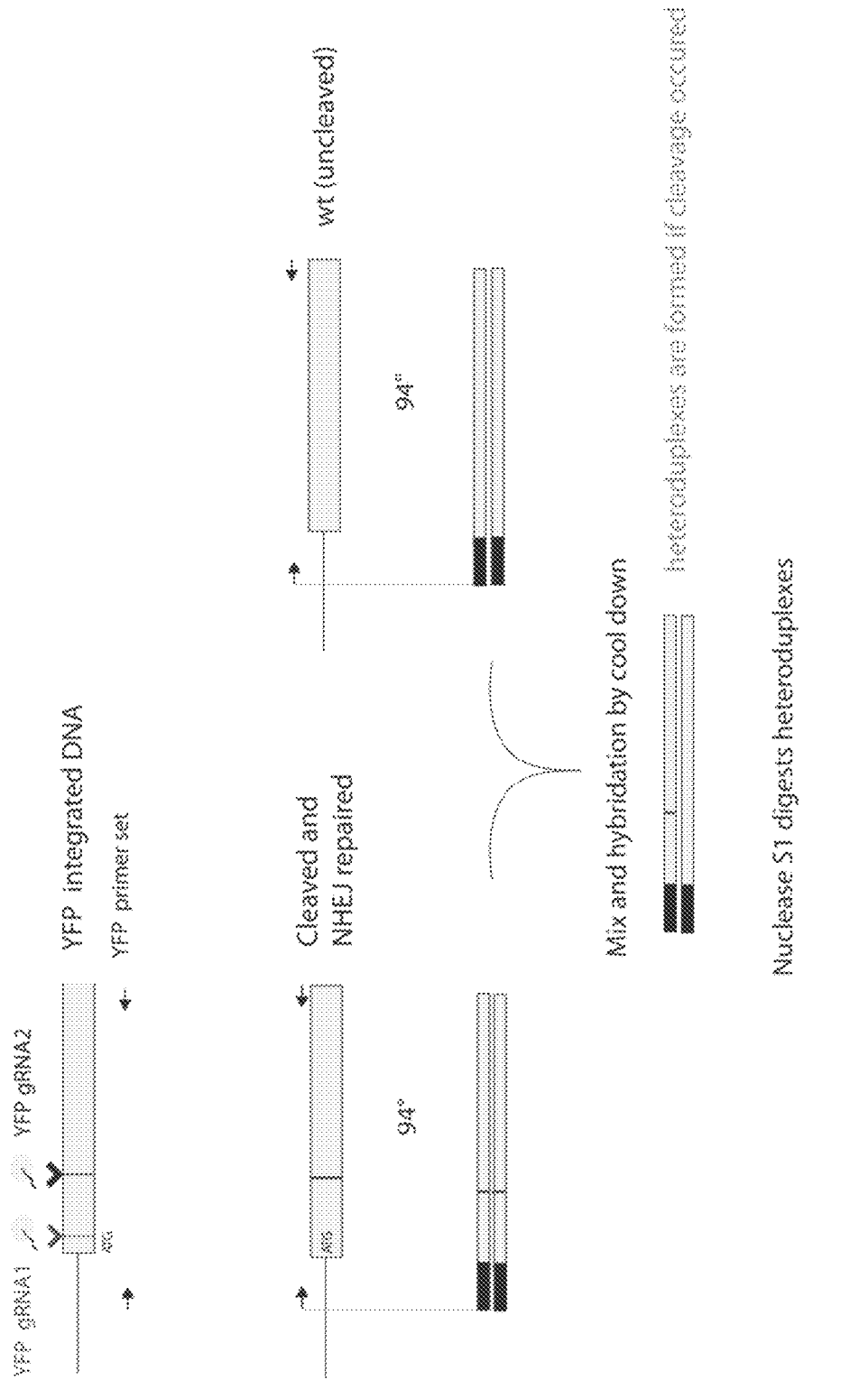
Figure 2B:
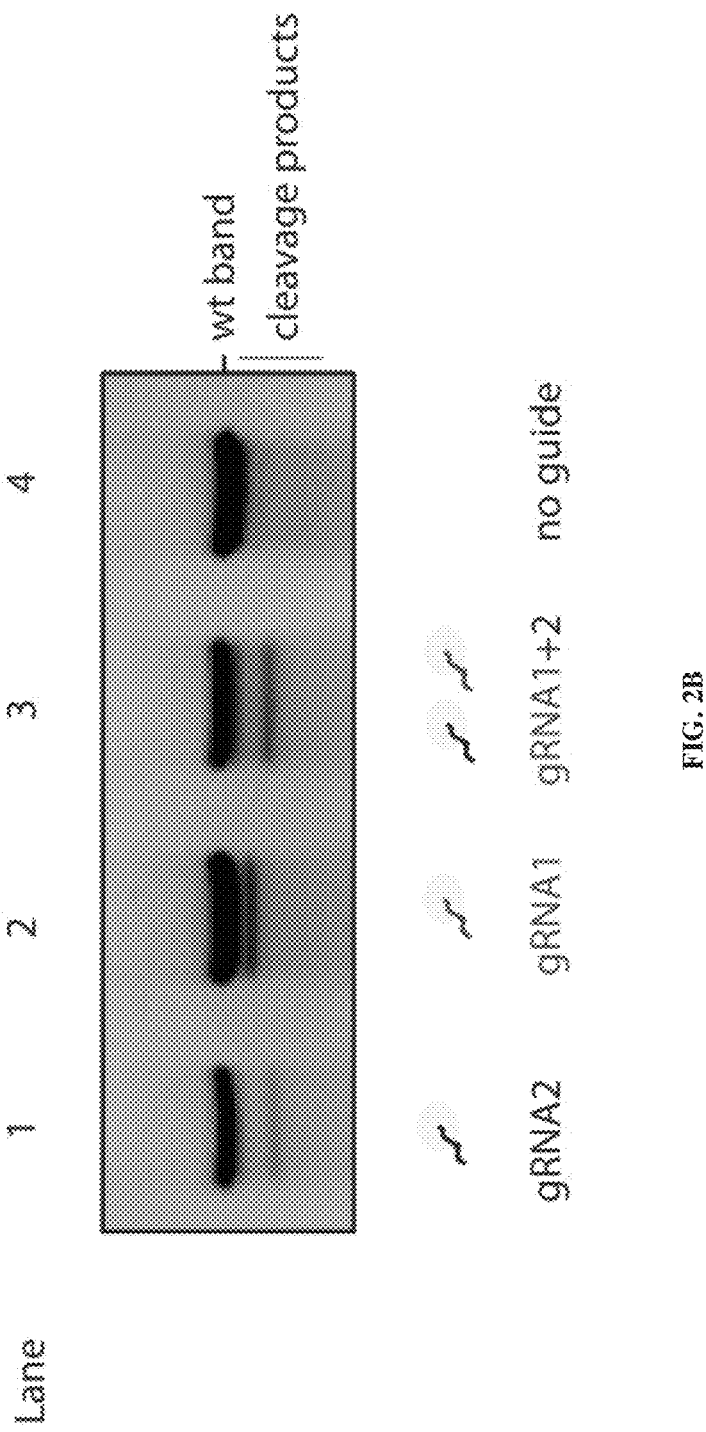

FIG. 2A-FIG. 2B: Molecular validation of genetic cleavage by YFP-CRISPRs-VLPs

FIG. 2A: Localization of gRNAs recognition sites on the YFP gene, primers used and principle of the surveyor assay. L929 murine cells were lentitransduced with a YFP coding vector at low Multiplicity Of Infection (MOI). After 72h, cells were next treated with VLPs loaded with gRNAs targeting the YFP gene at two different positions as indicated. To ascertain the cleavage of YFP, cells treated by Cas9-VLPs were lysed and genomic DNAs were extracted and analyzed by the SI nuclease-based surveyor assay. The test detects heteroduplexes that are formed if two closely related ssDNA molecules hybridizes: S1 nuclease digestion is thus a proof that DNA was cleaved by Cas9.

FIG. 2B: Surveyor assay on L929 cells treated by VLPs loaded with gRNAs2, 1, or a combination of both of them. Formation of heteroduplexes is detected for each rRNAs condition, revealing truncated versions of YFP whose size depends on the position of the gRNA on the YFP sequence.

Figure 3A:
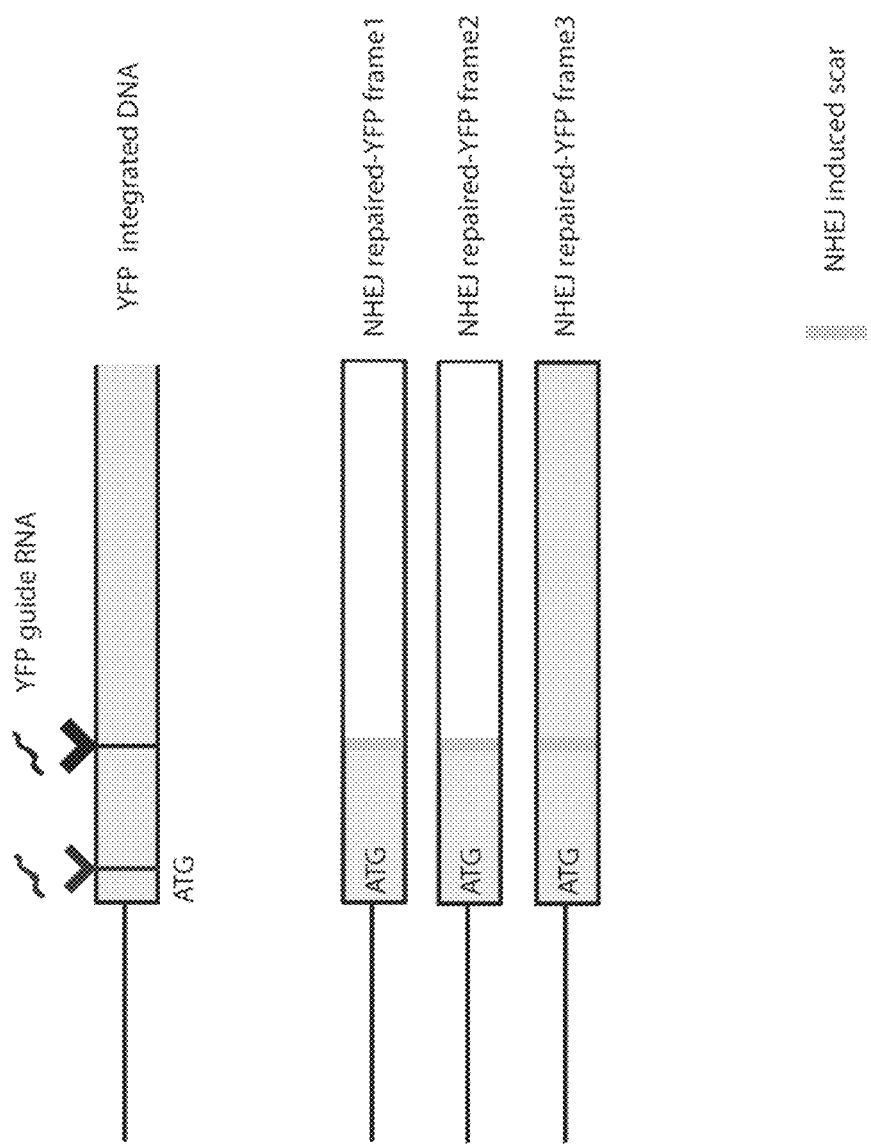
Figure 3B:
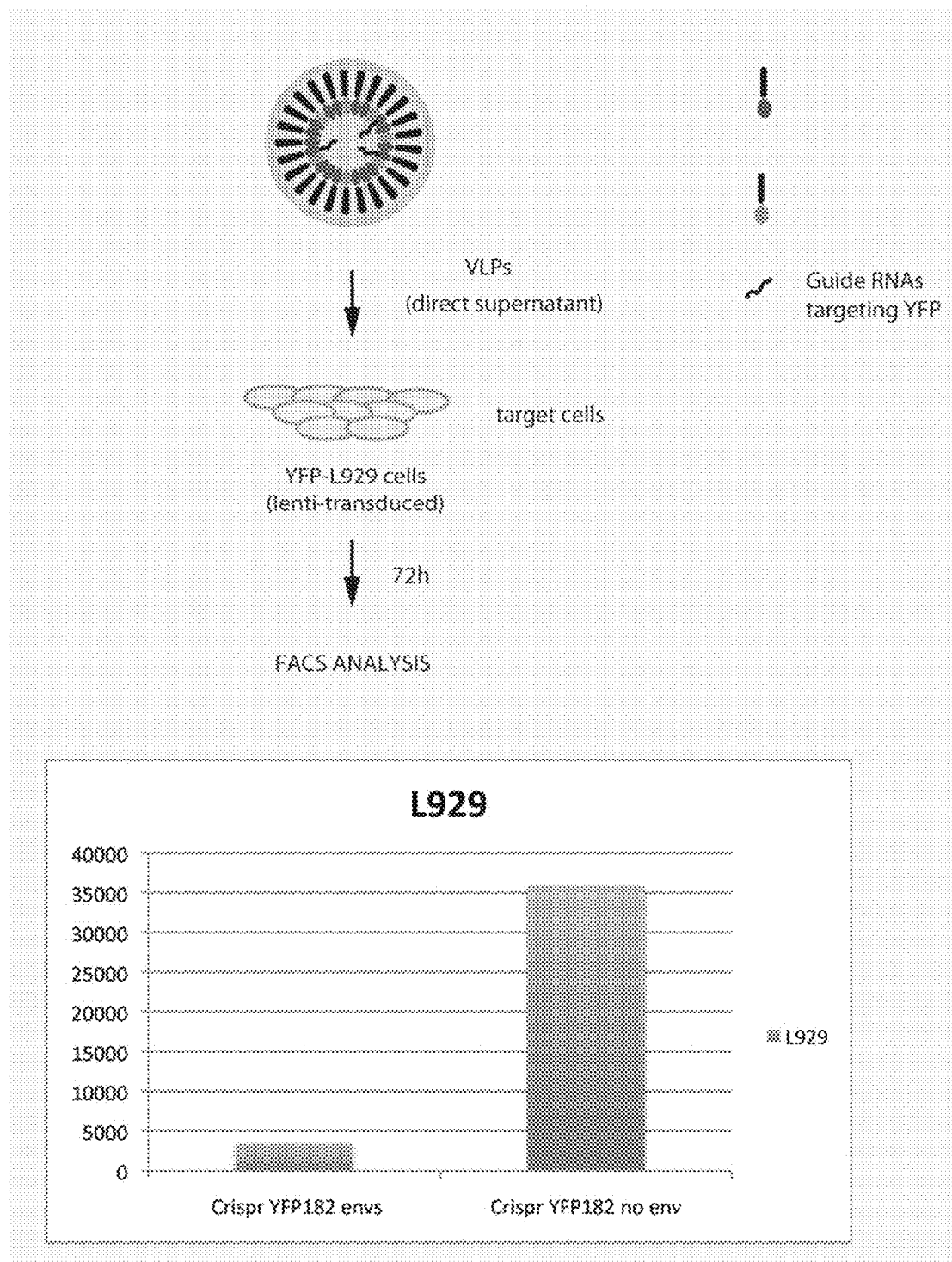

FIG. 3A-FIG. 3B: CRISPR-mediated disruption of YFP in L929 murine cells by Cas9-VLPs.

FIG. 3A: A guide RNA was raised to target YFP downstream the initiation codon ATG. After cleavage cells could repair this gap by NHEJ, a mechanism that could create small deletions and indels, a scar that could alter the YFP frame in some cells. 3 different versions of repaired YFP could thus be generated by the natural reparation machinery, only one of them restauring an in-frame YFP and a maintenance of the YFP phenotype. Accordingly, cleavage should induce a detectable but incomplete decrease of YFP in target cells.

FIG. 3B: VLPs loaded with Cas9 and a guide RNAs targeting YFP were produced and directly introduced into the medium of YFP-L929 cells, a murine fibroblastic cell line # where YFP was stably integrated into the genome by lentivector transduction. Envelope-less VLPs were also produced and used as a negative control. 72h after treatment cells were analyzed by flow cytometry (FACS) and global Mean Fluorescence Intensity (MFI) was monitored revealing the strong effect of YFP-breaking Cas9-VLPs on YFP L929 target cells. A 7-fold decrease of MFI was measured for cells treated by enveloped VLPs as compared with non treated YFP-cells or treated by env less VLPs*. We show here that Cas9-VLPs loaded with a specific guide RNA can be used without further concentration/purification process as CRISPR delivery agents.

FIG. 4A-FIG. 4D: Deletion of the Myd88 locus using conventional Cas9 delivery methods vs Cas9 VLPs FIG. 4A: Schematic representation of the Myd88 genomic DNA and localization of the different tools used for the Myd88 cleaving assay. Two different CRISPRs sequences were designed against the human Myd88 gene as represented in purple and green. Grey boxes correspond to the regions where the two PCR primers hybridize. They have been optimized for the amplification of gMyd88 which generate an amplicon size of 420 nts. Should the CRISPRs system be active in target cells, a deletion of 160 nts occurs in some cells and can be repaired by NHEJ which gives rises to a 260 nts—in size truncated version of the gene.

Figure 4A:
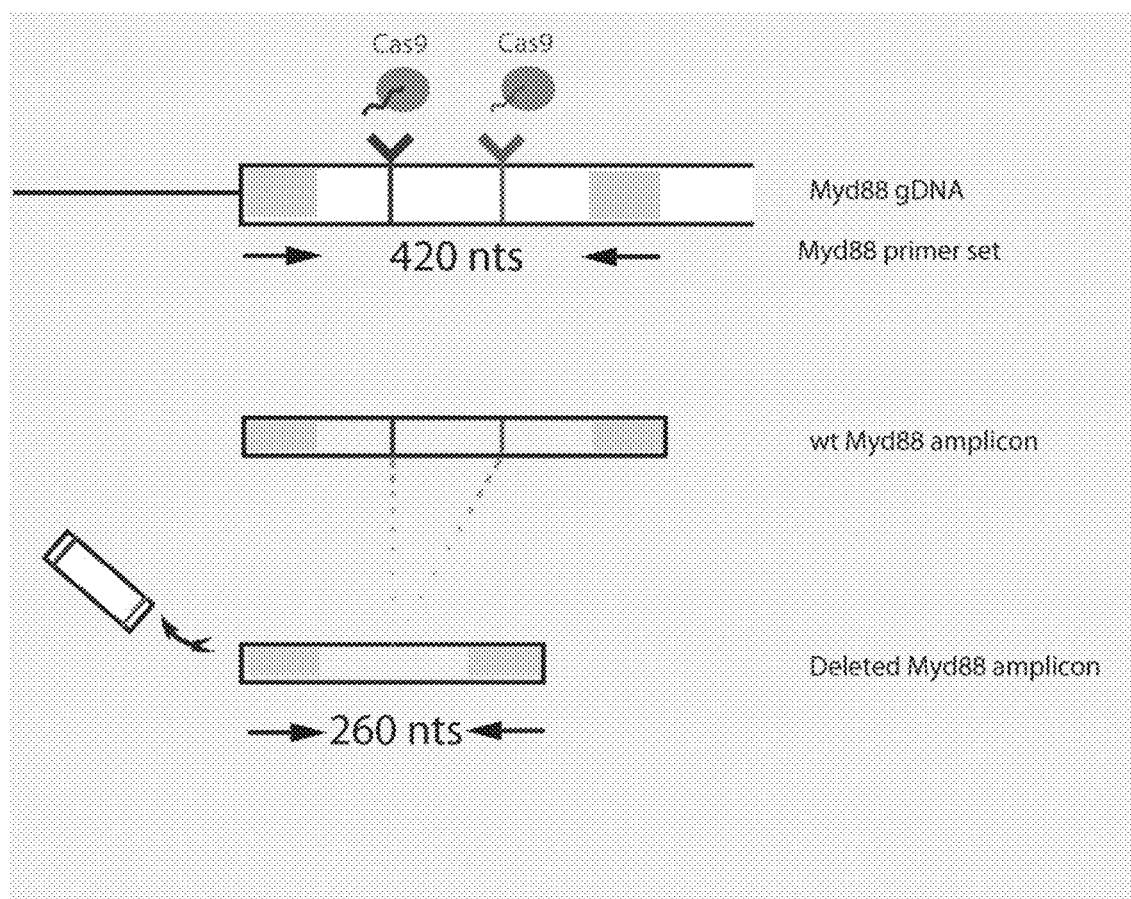
Figure 4B:
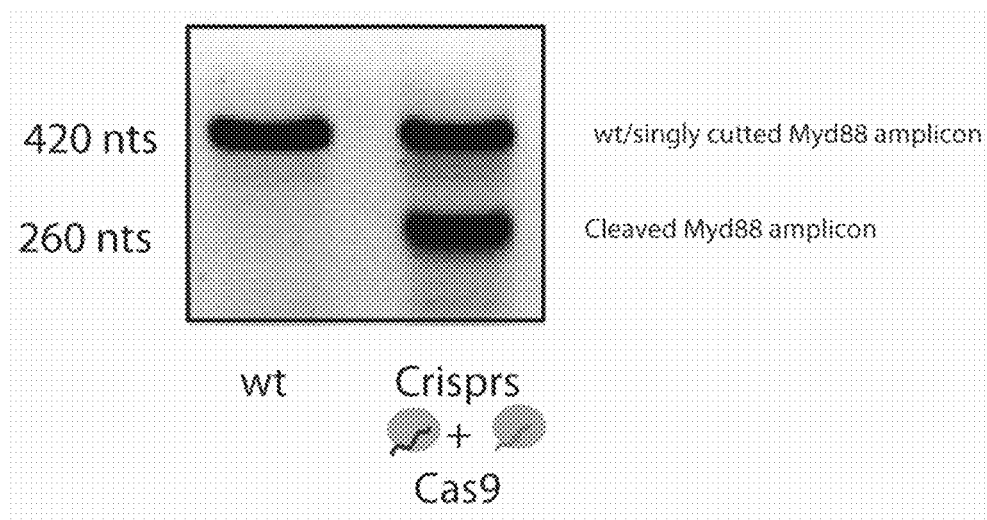

FIG. 4B: PCR-amplification of gMyd88 in wt-HEK or after transfection with both Myd88 CRISPRs and a Cas9 encoding plasmid. After extraction of genomic DNA, a PCR-assay was performed using the Myd88 primer set. In the population treated with CRISPRs components, two amplicons are generated corresponding to the uncleaved form of Myd88 (or a version which has been cleaved by a single CRISPR) and a double-cut version after cleavage of the gene at the two targeted positions. We can note that the Myd88 deletion does not affect all treated cells, indicating that the cleavage mediated by the transfected CRISPR components system is not complete.

Figure 4C:
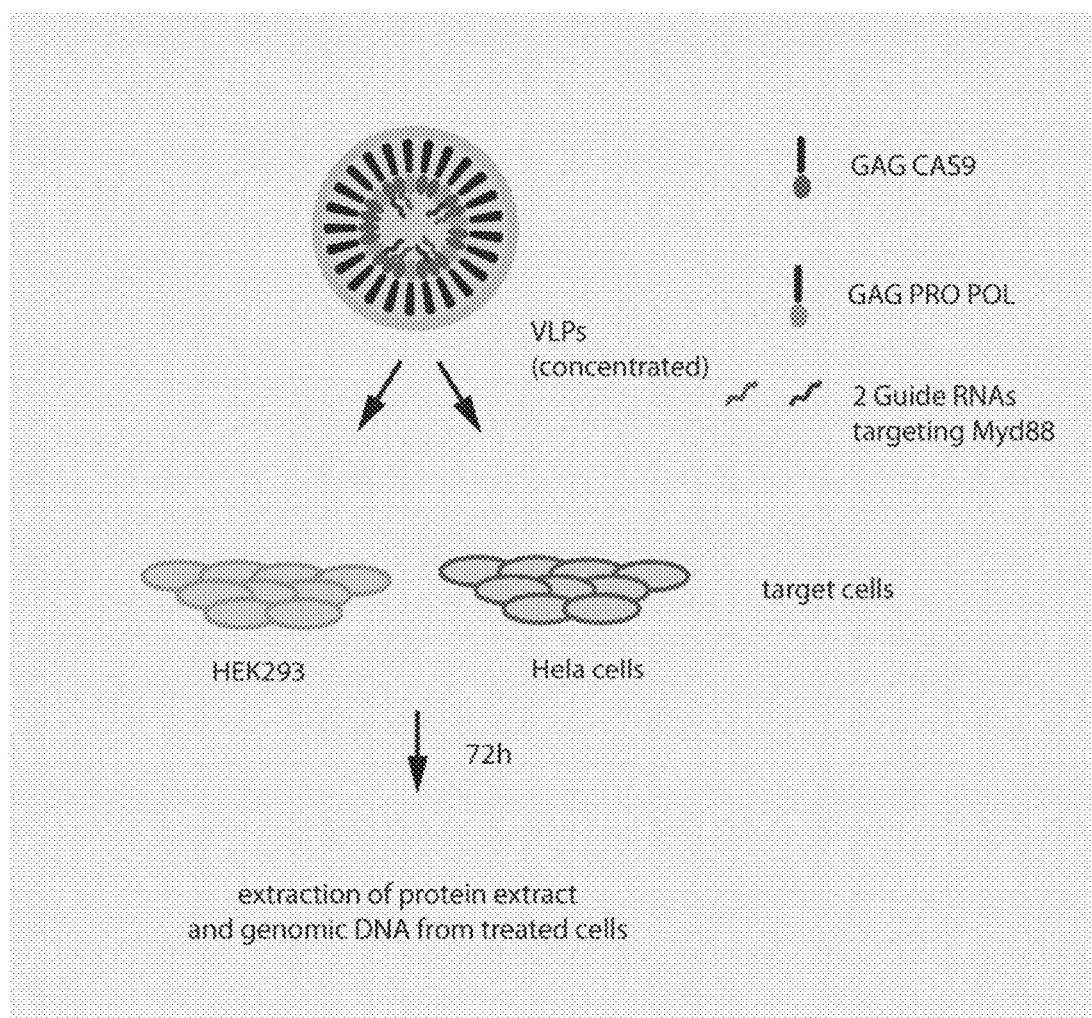

FIG. 4C: We also attempted to deliver both Myd88 guide RNAs by Cas9 loaded VLPs. For this VLPs were produced following the procedure described in FIG. 1 and different experimental procedures were explored, varying for the ratio of plasmid used and the nature of the envelope (R1-R4). After collecting and concentrating them, VLPs were introduced into the medium of HEK or Hela cells and efficiency of the Myd88 cleavage was next assessed by PCR.

Figure 4D:
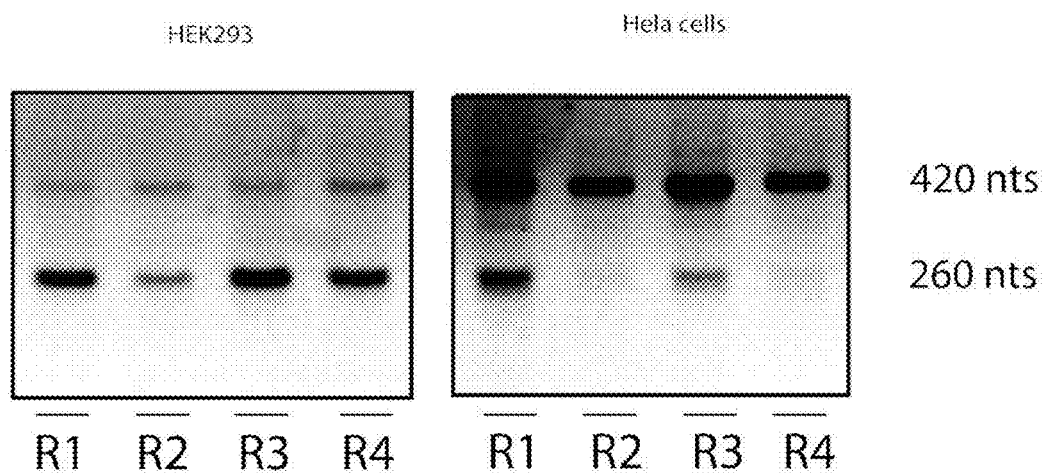

FIG. 4D: Myd88 amplification using the Myd88 primer set and the genomic DNA extracted from cells treated by VLPs. While all preparations were equally efficient in cleaving Myd88 in HEK cells (left panel), some differences can be appreciated in Hela cells, reflecting the importance of the envelope/ratio used. A particular protocol seems optimal (R1) for both cell types.

Figure 5:
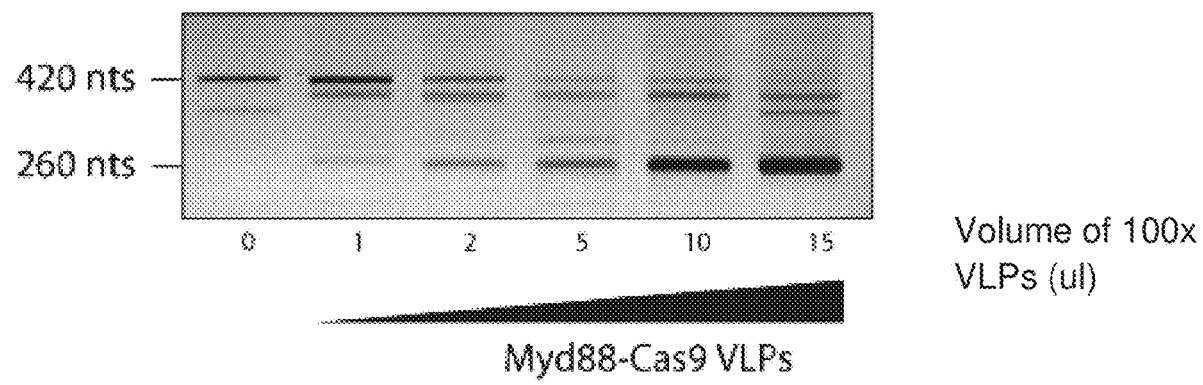

FIG. 5: Dose dependent cleavage of the Myd88 gene induced by Cas9-VLPs Cas9-VLPs loaded with two gRNAs targeting the Myd88 gene were produced, concentrated and stored 15 days at 4° C. Increasing amount of VLPs were next added to the medium of HEK293T target cells plated in a 12-w plate (150000 cells/w). 20h after VLP treatment, cells were lysed and genomic DNA was purified to analyze the genetic cleavage of the Myd88 locus. The signal revealing the deletion of Myd88 (260 nts) increases with the amount of VLPs introduced in the medium.

This shows that Cas9-VLPs are active in target cells less than 24h after their introduction. We also noted that the VLP preparation can be stable at least 15 days at 4° C.

Figure 6:
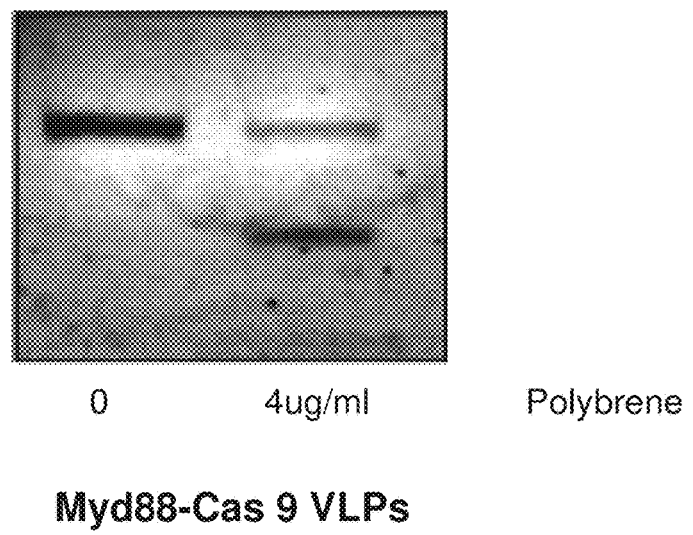

FIG. 6: Cleavage of the Myd88 gene in HEK targets by Cas9-VLPs is potentiated by polybrene.

Suboptimal doses of Cas9-VLPs loaded with two gRNAs targeting the Myd88 gene were introduced in the medium of 3×10e6 HEK target cells grown in complete medium supplemented or not with Hexadimethrine bromide (polybrene), a polycation favoring the contact of particles with target cells. 48h after VLP treatment, cells were lysed and genomic DNA was purified to analyze the genetic cleavage of the Myd88 locus. In this condition where under-saturating amounts of VLPs were used, the Myd-88 cleavage is undetectable in cells cultivated in a standard medium but is strongly potentiated by polybrene addition.

Figure 7A:
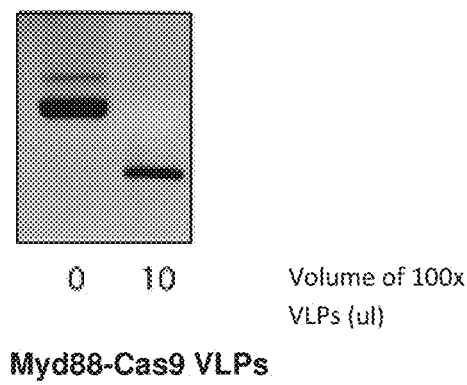
Figure 7B:
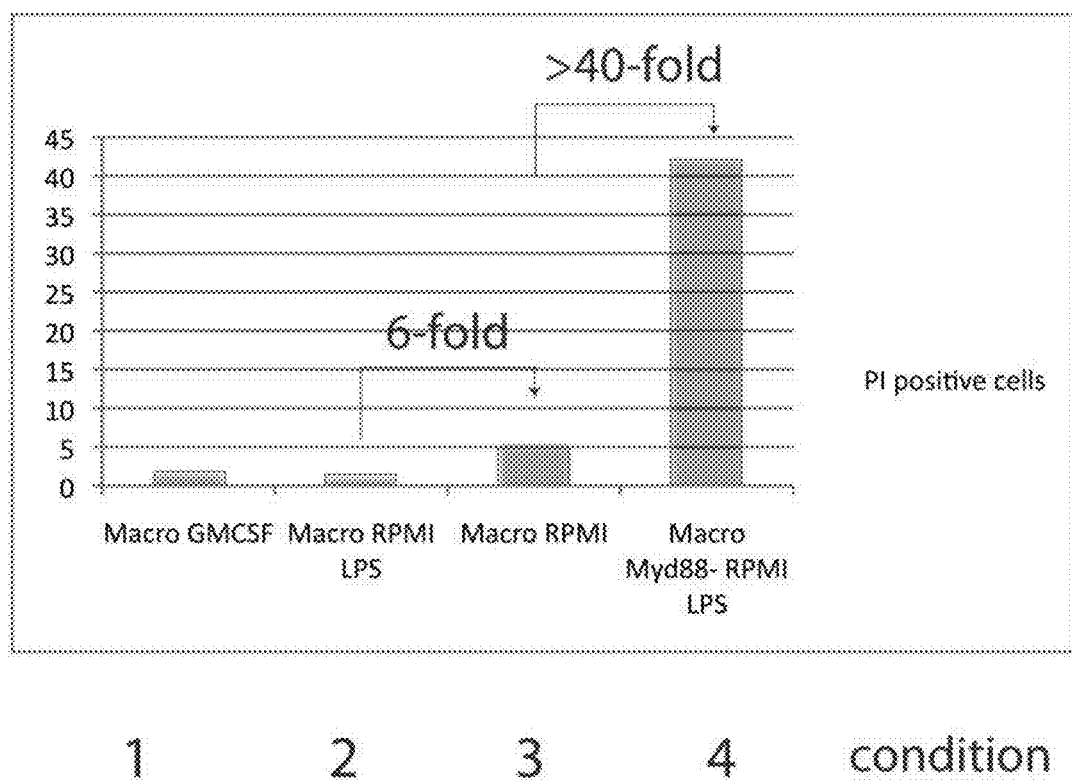

FIG. 7A-FIG. 7B: Cleavage of the Myd88 gene induced by Cas9-VLPs in human monocytes-derived macrophages Genotype FIG. 7A: Cas9-VLPs loaded with two gRNAs targeting the Myd88 gene were concentrated and introduced in the medium of human monocytes-derived macrophages after 6 days of differentiation with Granulocyte-Macrophage Colony Stimulating Factor (GMCSF) (100000 cells per well i a 48-w plate). 48h after treatment with VLPs, cells were lysed and genomic DNA was purified to analyze the genetic cleavage of the Myd88 locus. Under this condition, the Myd88 gene is cleaved with such high efficiency after treatment with VLPs that the wt sequence cannot even be detected by conventional PCR thus suggesting an almost complete cleavage mediated by Myd88-VLPs in primary non dividing cells.

Phenotype

FIG. 7B: According to Lombardo et al*, human macrophages massively die by apopotosis when cultivated without GMCSF, unless they are stimulated by a TLR-4 agonist like LPS. This resistance to apoptosis is LPS- and Myd88-dependent. To check wether VLPs treated cells lost their Myd88 function, we cultivated them without GMCSF (in RPMI medium) and stimulated them with LPS during 72h. Upon this treatment WT macrophages resisted to GMCSF deprivation (compare condition 2 to condition 3) while macrophages treated with Myd88-cleaving Cas9-VLPs died massively (condition 4). This strongly suggests that VLPs treatment inactivated the Myd88 at the functional level.

Figure 8:
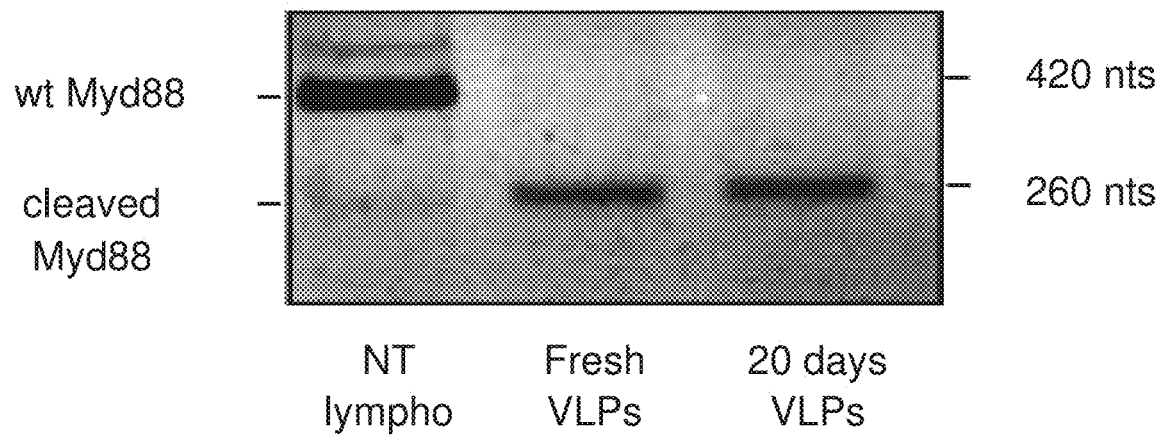

FIG. 8: Cleavage of the Myd88 gene induced by Cas9-VLPs in freshly-purified primary human lymphocytes.

Human purified lymphocytes (Ficoll/percoll) were plated at 40×10e6 cells/ml in 200 ul in a 48w plate. Cells were next treated with a fresh preparation of Cas9-VLPs targeting Myd88 and an older one kept 20 days at 4° C., in a transduction medium supplemented with polybrene (4 ug/ml). After 2h, 500 µl of fresh medium was added to the transduction medium and cells where maintained in culture for 40h before their lysis and genomic DNA extraction. Cleavage of Myd88 was next investigated by PCR revealing the wt or the cleaved form of Myd88. In both VLP conditions, the Myd88 gene was cleaved. 1 million of quiescent lymphocytes were genetically modified in less than 48h with a single treatment of VLPs without any apparent toxicity.

Figure 9:
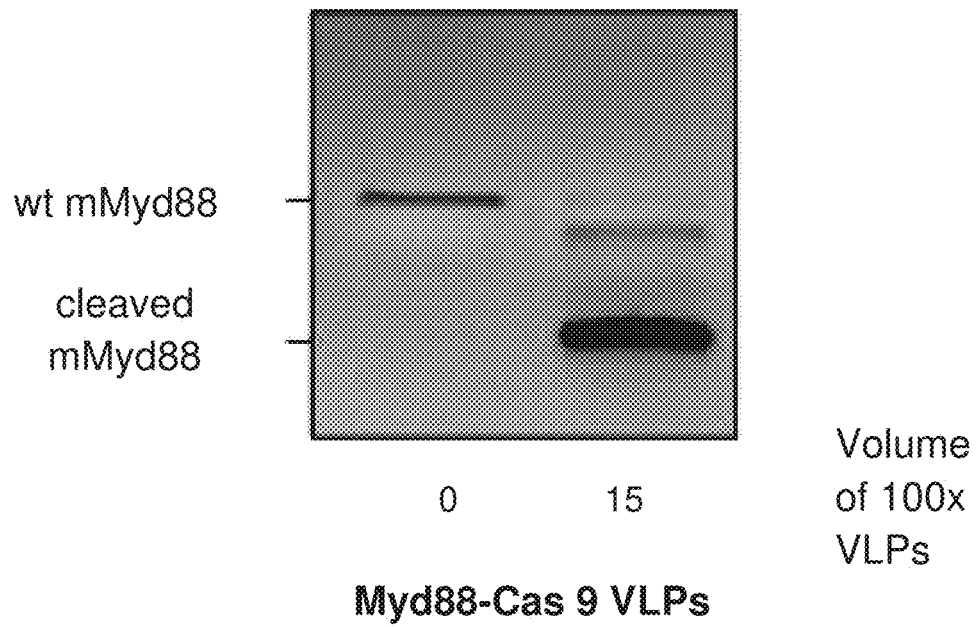

FIG. 9: Cleavage of the Myd88 gene induced by Cas9-VLPs in murine bone marrow-derived macrophages Macrophages were differentiated from bone marrow cells flushed-out from mouse femurs incubated during 8 days in MCSF containing medium. Cells were next treated with a fresh preparation of Cas9-VLPs targeting mMyd88 in a medium supplemented with polybrene (4 ug/ml). It is noteworthy that two new gRNAs were designed for this experiment that specifically targeted the murine gene.

Cells were cultivated 48h before lysis and genomic DNA extraction. Cleavage of Myd88 was next investigated by PCR revealing the wt or the cleaved form of the murine Myd88 gene based on the design of the hMyd88 assay. A very efficient cleavage was detected by PCR in VLP-treated cells while bands corresponding to the complete or partially cleaved mMyd88 (by only one gRNA) appear faint.

Figure 10A:
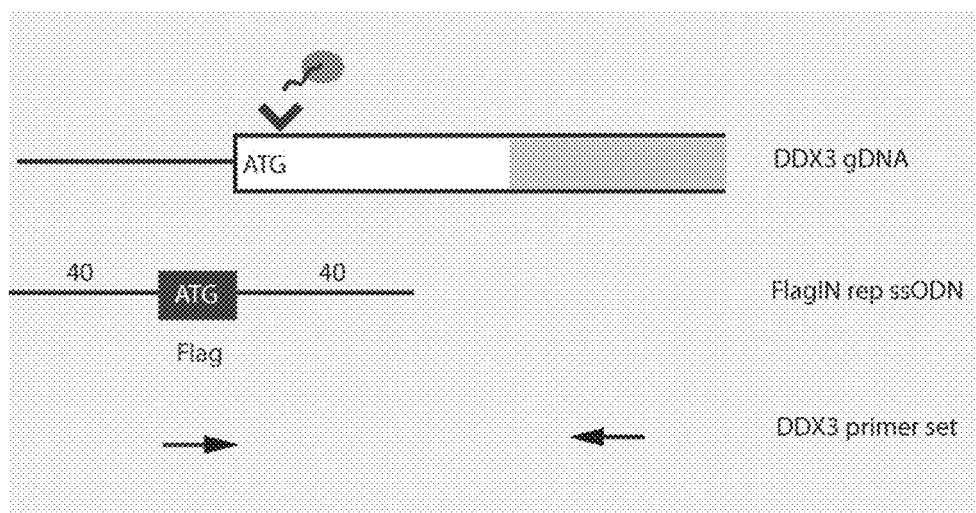
Figure 10B:
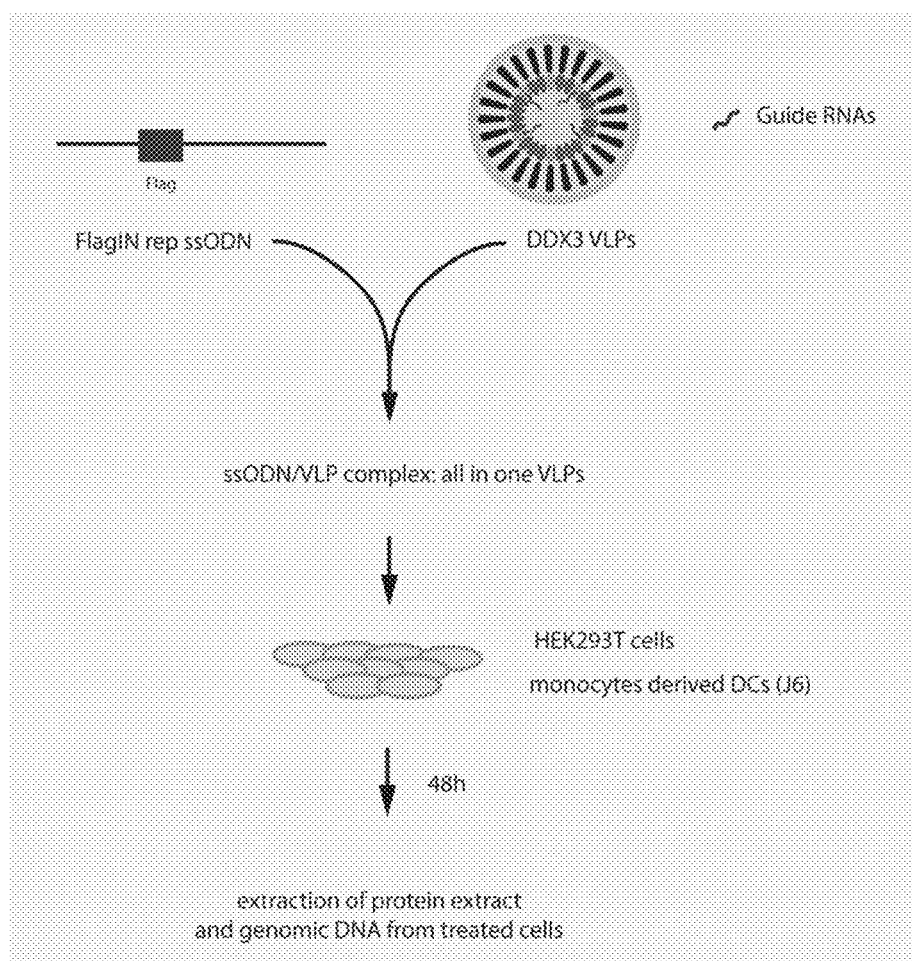
Figure 10C:
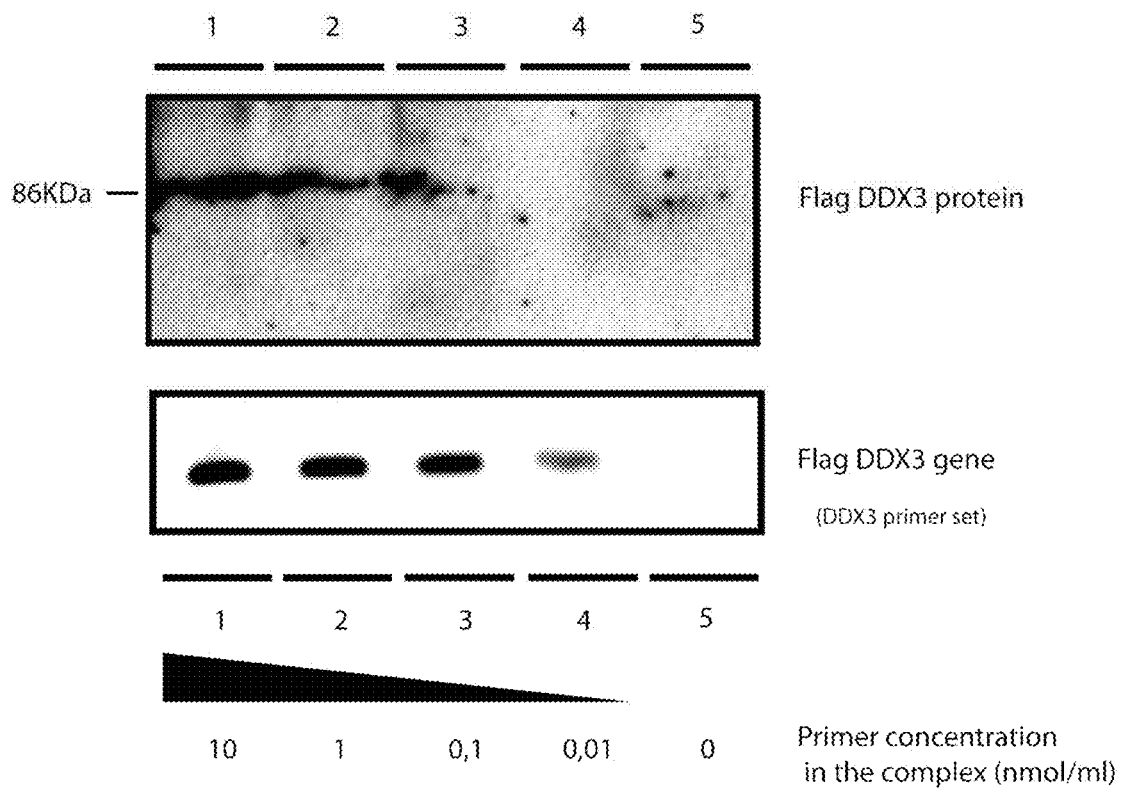
Figure 10D:
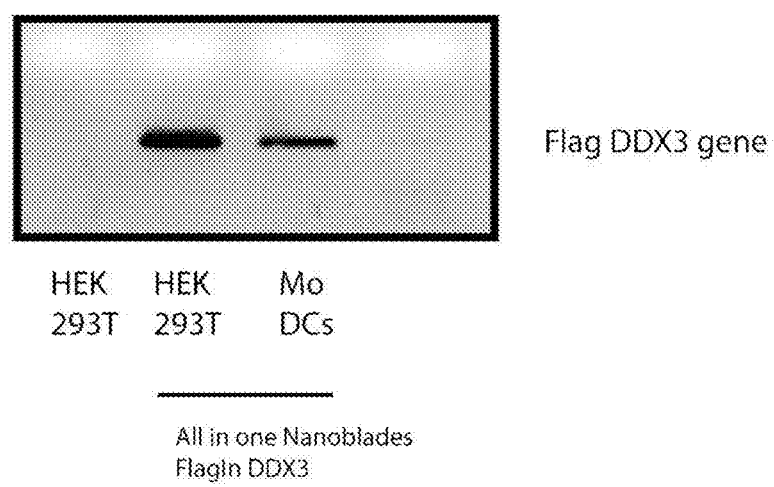

FIG. 10A-FIG. 10D: Targeted insertion of a flag-tag sequence in the endogenous DDX3 genomic locus mediated by 'all in one' Cas9-VLPs FIG. 10A: schematic representation of the human DDX3 genomic locus and the different tools used in the experiment. The purple arrow represents the locus cleaved by the DDX3 CRISPR and the grey region an intronic region of DDX3. The FLAG IN rep primer (ssODN) is represented as a single strand DNA exhibiting 40 nt homology-repair arms, flanking the Flag-tag sequence, that are homologous to the DDX3 locus. Primers used in the PCR assay are represented. FIG. 10B: Principle of the 'all in one' VLPs delivering the Cas9 protein, the gRNAs and the repair primer. VLPs targeting DDX3 were produced, centrifuged and stored at 4° C. VLPs were then combined with increasing doses of ssODNs and complexes added on HEK target cells cultivated in classic growing medium. Target cells were next lysed 72 h later for preparation of protein extracts and genomic DNA FIG. 10C: Western-Blot analysis of cells treated with 'all in one' DDX3 VLPs. A Western-blot signal revealed by the flag antibody and corresponding to the DDX3 expected molecular weight (86KDa) can be detected at the highest concentrations of ssODNs. This indicates that the Flag sequence was successfully inserted at the DDX3 locus of VLP-treated cells. This was further confirmed by PCR on the genomic DNA extracted from VLP-treated cells. Primers used (depicted in FIG. 10A) should amplify a DNA segment only if the Flag sequence is inserted in the DDX3 gene since the forward primer hybridizes to the Flag sequence and the reverse primer hybridizes to the intron of DDX3). As shown in lower panels, the genetic modification is obvious for higher concentration of primers and decreases with the dose but remains detectable—at the DNA level—for a concentration as low as 0.01 nmol/ml (lane 4). FIG. 10D: Introduction of the Flag sequence upstream the endogenous locus of DDX3 in human monocyte-derived dendritic cells (Mo-derived DCs). VLPs and ssODN (5 nmol/ul final) were complexed and the mix used to treat Mo-derived DCs in a transduction medium containing polybrene (4 ug/ml). Genomic DNA analysis indicates that the flag sequence was succesfully engrafted into the endogenous locus of DDX3 in human primary DCs by a single treatment of VLPs.

Figure 11:
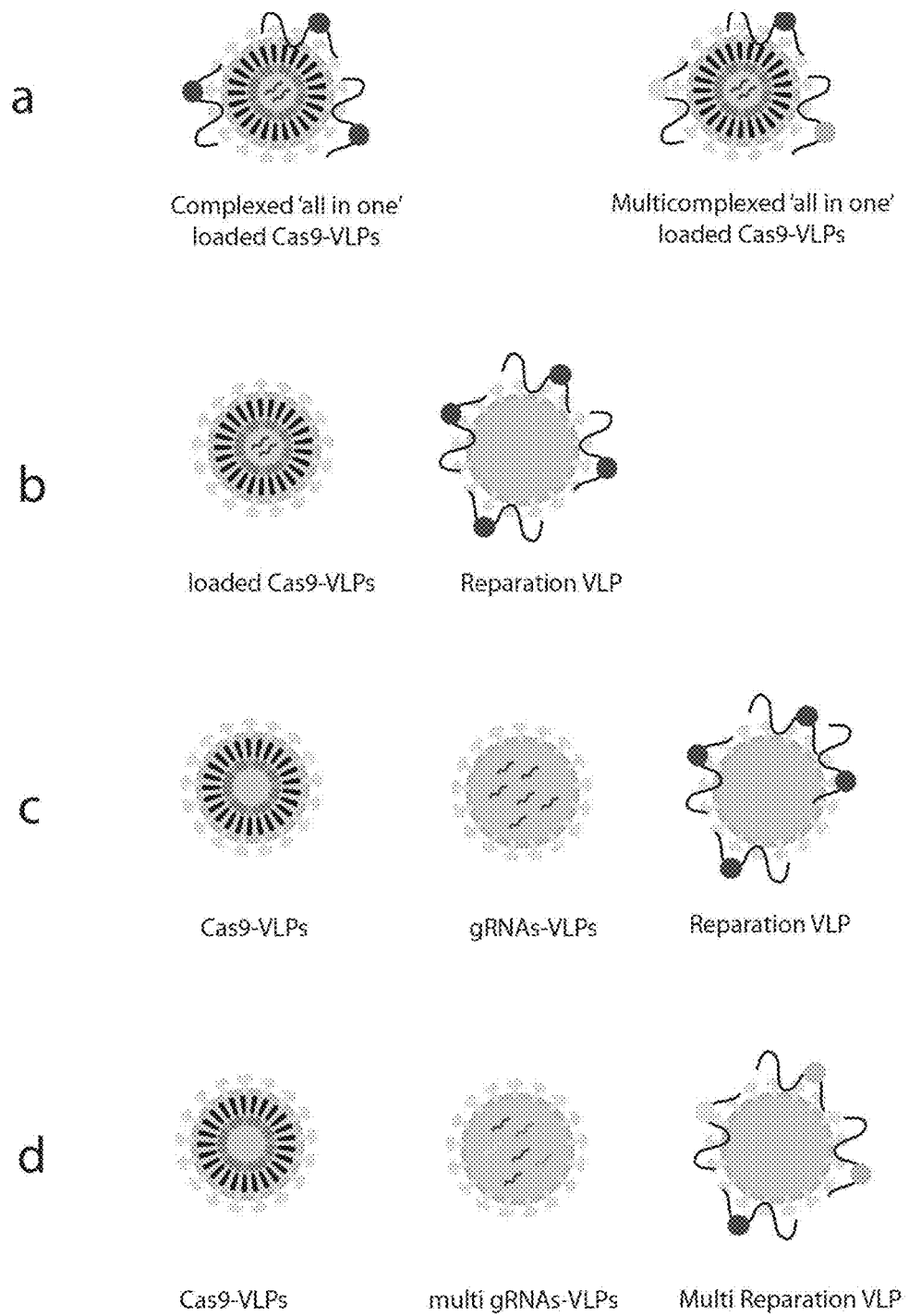

FIG. 11: Panel of possibilities using Nanoblades and their association with 'helper' VLPs We have shown that 'all in one' VLPs incorporating Cas9, gRNAs and possibly combined with a reparation ssDNA can be generated and deliver the complete package in recipient cells. This agent depicted in (a) is highly versatile in itself. Since VLPs can incorporate several gRNAs and may certainly be complexed after production with different reparation primers, many possibilities are offered to a scientist/company to create customized tools at low cost. As referenced in (Abe et al. J Virol 1998), VLPs of different nature may be complexed outside the cell after production and may complement each other, one helping the other to enter into the cell for example. Given this property of VLPs, we may imagine other ways to prepare an active agent to transfer the actors of the CRISPRs system by mixing particles, each of them being dedicated to a particular cargo. In (b) is proposed a system where could be mixed gRNA-Cas9-VLP and particles simply complexed by the reparation primer: the mixture of both types of particles would be in this case, the final active agent. To go further, gRNAs could also be packaged in a particular type of particle and combined after production with unloaded Cas9-VLPs to create a particle mixture able to deliver all the components. This system is depicted in (c). Considering the theoretical possibility to incorporate several gRNAs in VLPs, to choose different viral envelope to pseudotype each type of VLPs, and to associate them with different types of ssDNA, we may even imagine more complex agents, (d). While this segregation of CRISPRs components in different types of particles may certainly affect the global efficiency of the final agent, it may offer to a company producing nanoblades a vast panel of possibilities to improve the nanoblade service and render it costless. Should the (c) system be efficient enough, it only requires the preparation of a large well-titered batch of generic Cas9-VLPs to be associated with gRNAs particles customized specifically for each application. This system appears highly valuable from the industrial point of view, since a very precise molecular service is offered, which only necessitate the rapid costless preparation of the gRNAs-VLPs.

Figure 12A:
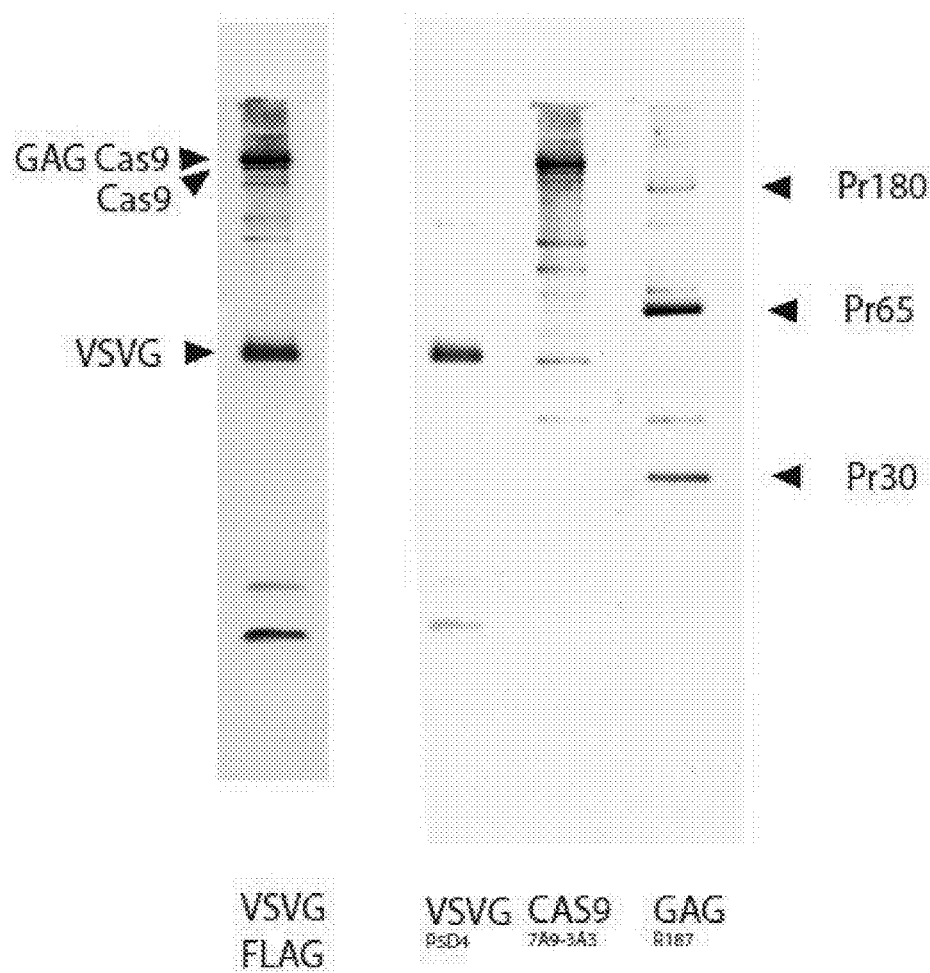
Figure 12B:
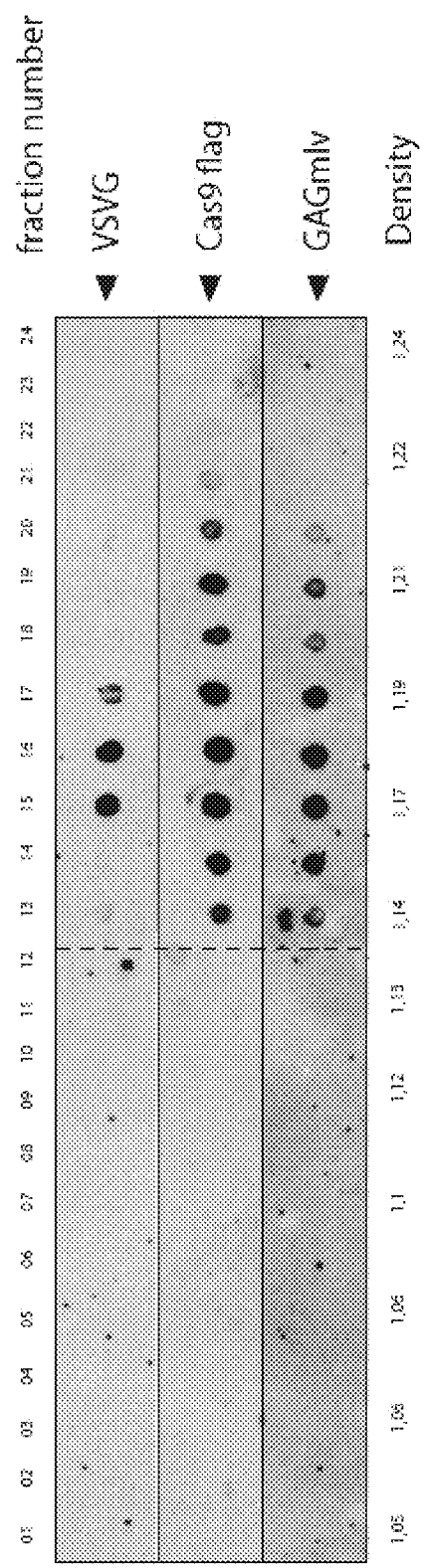

FIG. 12A-FIG. 12B: Western blot analysis and characterization of CAS9 Virus-derived particles separated on a discontinuous sucrose gradient.

FIG. 12A illustrates a Western blot gel electrophoresis. Lanes from left to right: (i) incubation with anti-Flag antibodies; (ii) incubation with anti-VSV-G antibodies; (iii) incubation with anti-CAS9 antibodies; (iv) incubation with anti-GAGmlv antibodies.

FIG. 12B illustrates a dot blots of fractions 1 to 24 collected after performing the separation of CAS9 virus-derived particles on a discontinuous sucrose gradient. Columns from left to right: fractions no 1 to no 24. Lanes from the upper part to the lower part of FIG. 12B: (i) incubation with anti-VSV-G antibodies; (ii) incubation with anti-CAS9 antibodies, (iii) incubation with anti-GAGmlv antibodies.

Figure 13:
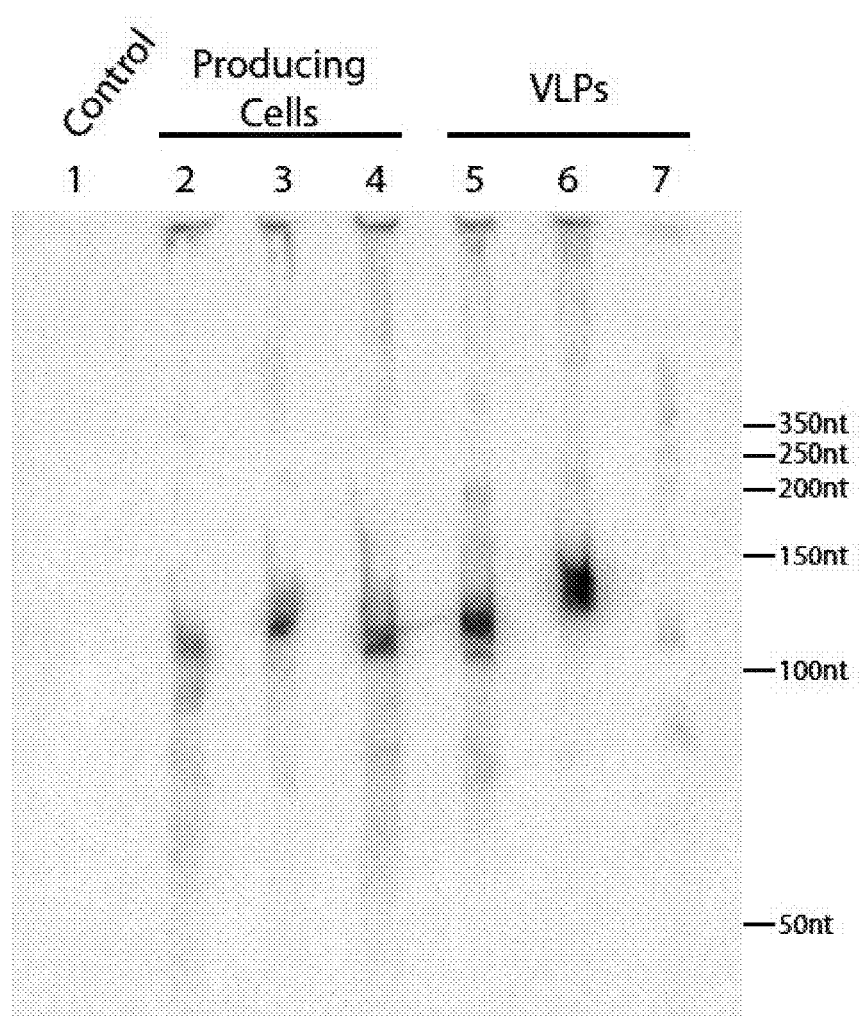

FIG. 13 Gag/Cas9 fusion actively loads guideRNAs within Virus-like particles (VLPs).

Northern blot directed against the conserved region of the guideRNA using total RNA extracted from producer cells (lanes 2 to 4) or the corresponding purified VLPs (lanes 5 to 7).

Figure 14A:
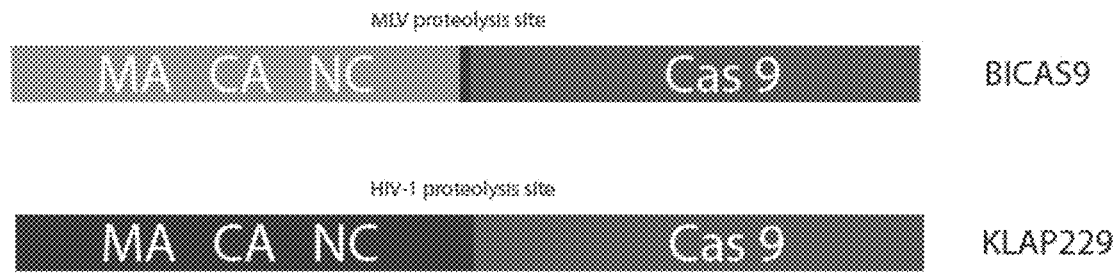
Figure 14B:
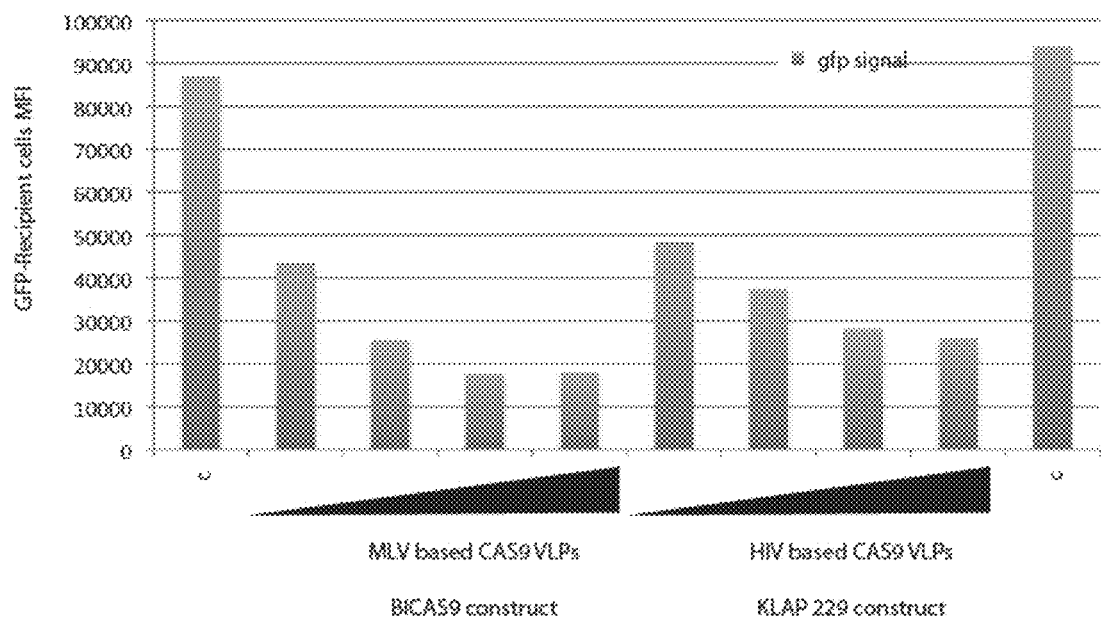
Figure 14C:
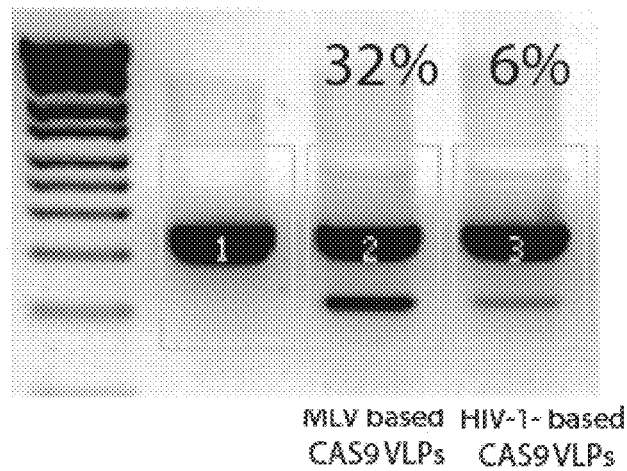

FIG. 14A-FIG. 14C FIG. 14A: Schematic representation of the coding cassettes designed for the production of MLV-based VLPs or HIV-1-based VLPs. Both cassettes were incorporated in an eucaryotic expression vector equipped with the early hCMV promoter, the rabbit-Bglobin intron and the rabbit pA signal. Both systems were optimized by exploration and test of diverse proteolytic sites separating the GAG cassette from the Cas9 gene. MLV based VLPs were produced as described elsewhere while HIV-1 based VLPs were produced similarly except that an HIV-1 helper construct encoding GAG POL Tat Rev proteins was transfected instead of the MLV GAG POL plasmid. Production of HIV-1 VLPs follows the same procedure as compared with MLV-based VLPs.

FIG. 14B: Concentrated VLPs engineered to incorporate a guide RNA targeting the GFP gene were used to transduce 30000 HEK293T cells expressing GFP. HIV-1 and MLV-based particles were produced with the same loaded gRNA (target sequence: CGAGGAGCTGTT-CACCGGGG—SEQ ID NO. 38). Recipient cells were plated the day before in a 96-w plate. Transduction medium was supplemented with polybrene (4 ug/ml). 72 hours after treatment with 3 increasing doses of each VLP-batch, fluorescence intensities were measured by a Fluorometer (Excitation 488, Emission 535). Fluorescence decrease was evident in VLPs-treated cells as compared with control non-treated cells (C), revealing the cleavage of the GFP gene within recipient cells. Results indicate that HIV-1 based VLPs are efficient in delivering the CRISPR/CAS9 system to a level slightly less efficient than MLV-based VLPs in these recipient cells (1.5-2 fold less efficient).

FIG. 14C: Cleavage of the WASP gene in primary human T cells stimulated with IL7. For this experiment, two guide RNAs targeting the human WASP gene were incorporated within HIV-1 or MLV-based VLPs before treatment of freshly purified T-cells stimulated with IL7. 500000 cells were plated in a 24w plate in 400 ul of RPMI medium supplemented with polybrene (4 ug/ml) and IL-7. Concentrated HIV-1 or MLV VLPs (10 ul of VLP dosed at 1 uM CAS9) were added in the culture medium. WASP deletion by CRISPR-CAS9 was next measured by PCR in recipient cells 24 hours after treatment. Primer used for amplification of genomic WASP gene were:

```
                                        (SEQ ID NO. 36)
    forward:    5'-ATTGCGGAAGTTCCTCTTCTTACCCTG (SEQ ID NO. 37)
    reverse:    5'-TTCCTGGGAAGGGTGGATTATGACGGG.
```

PCR conditions are: 95° C. 5 min followed by 25 cycles of (95° 30 sec-57° 30 sec-72° 30 sec) followed by 5 min at 72° C.

Amplicons were next loaded on a gel to reveal the state of WASP into VLP recipient T-cells: wt or cleaved. Gel analysis performed using the ImageJ software allowed a quantification of double-cutting efficiencies for MLV-based VLPs (32%) and HIV-1-based VLPs (6%).

Figure 15A:
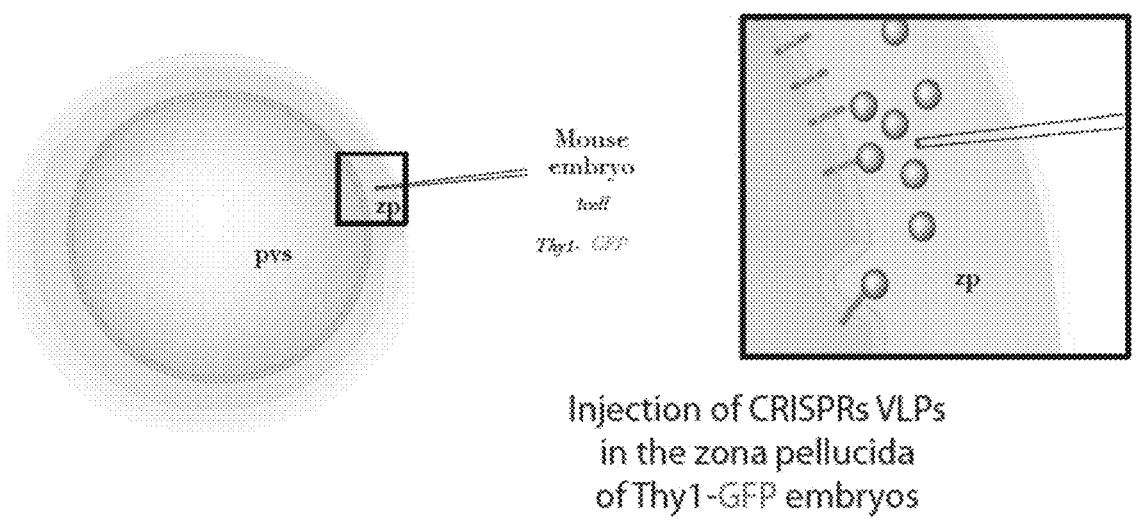
Figure 15D:
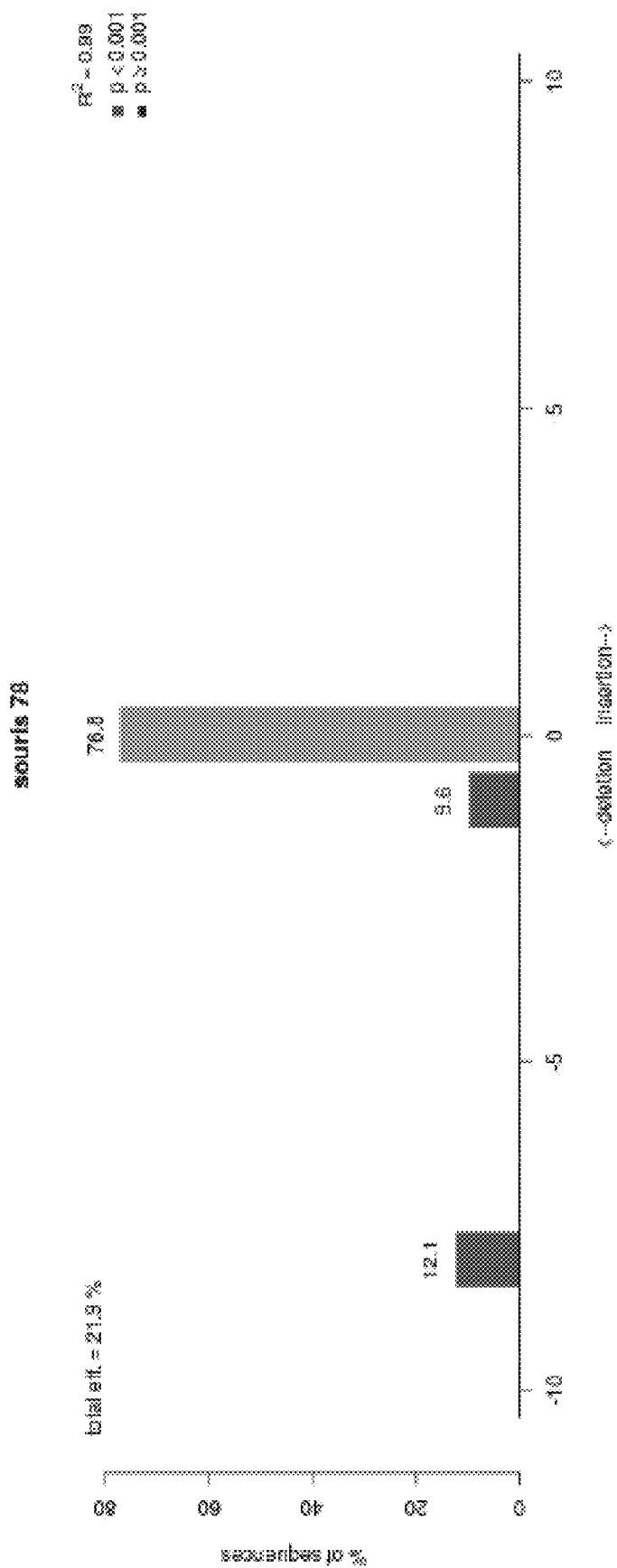
Figure 15E:
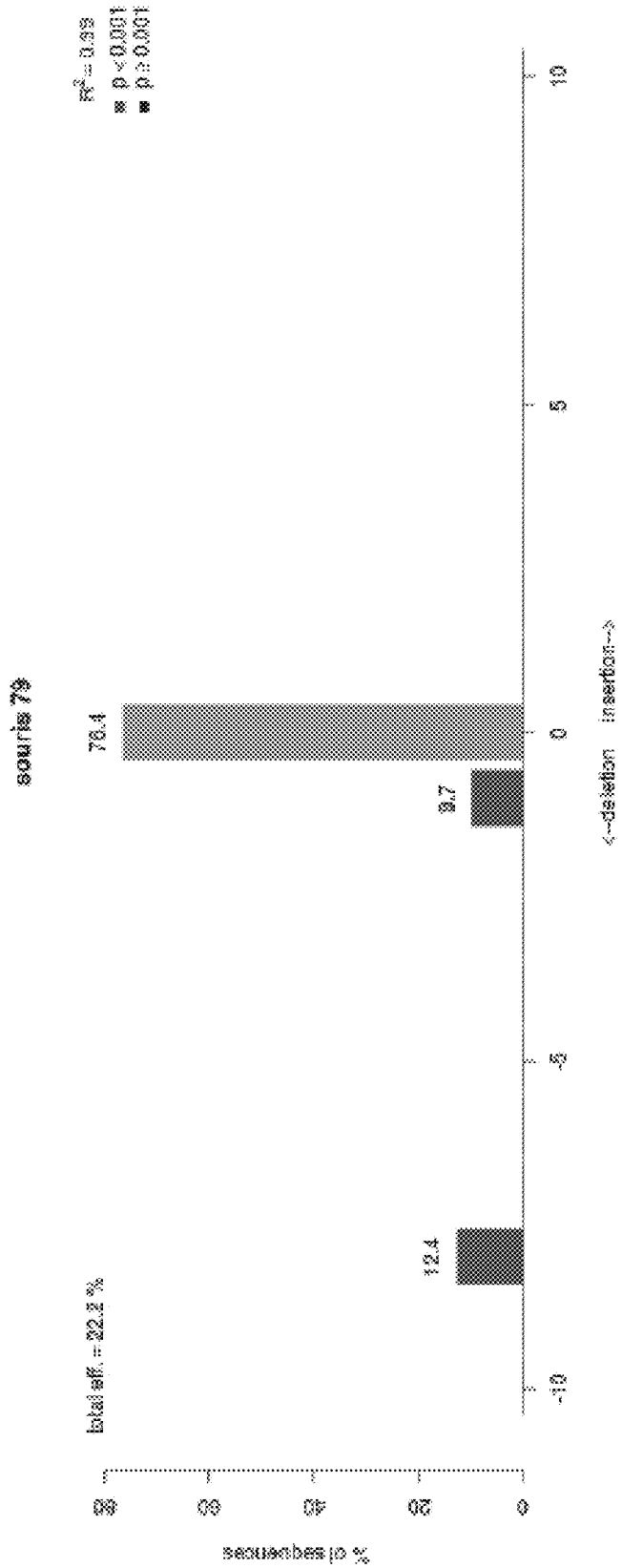
Figure 15F:
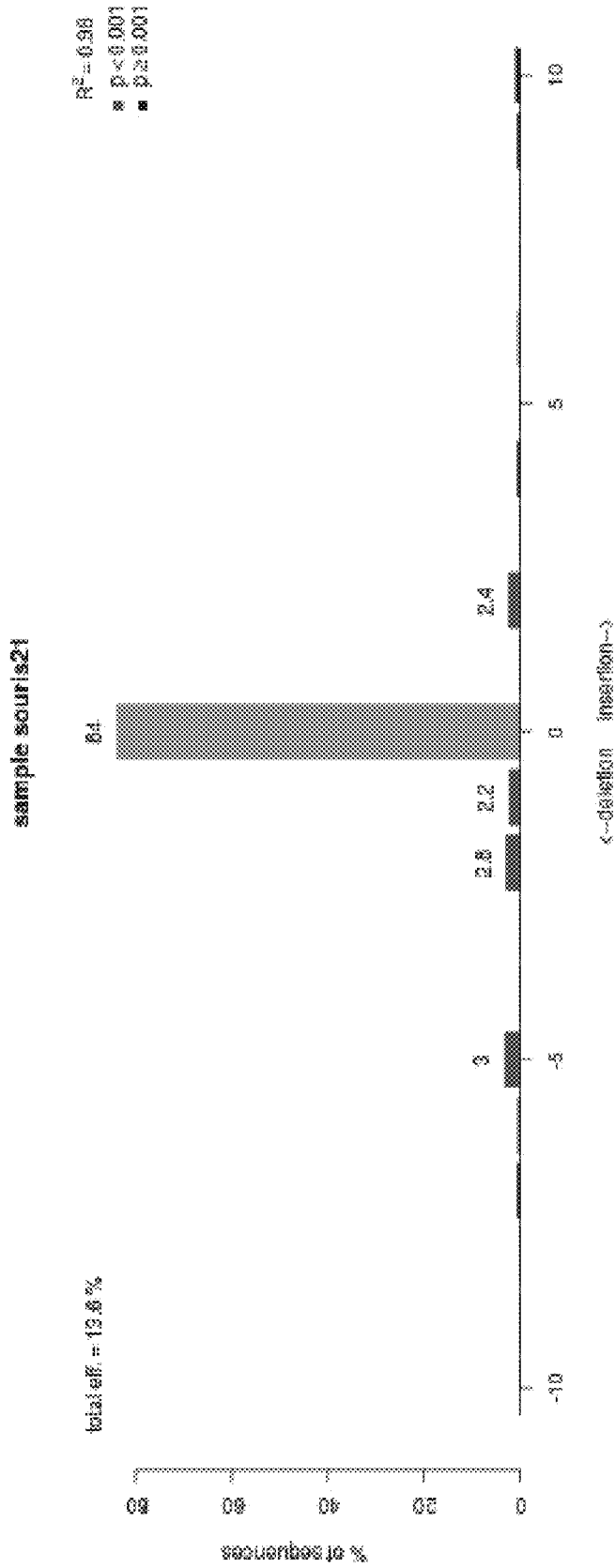
Figure 15G:
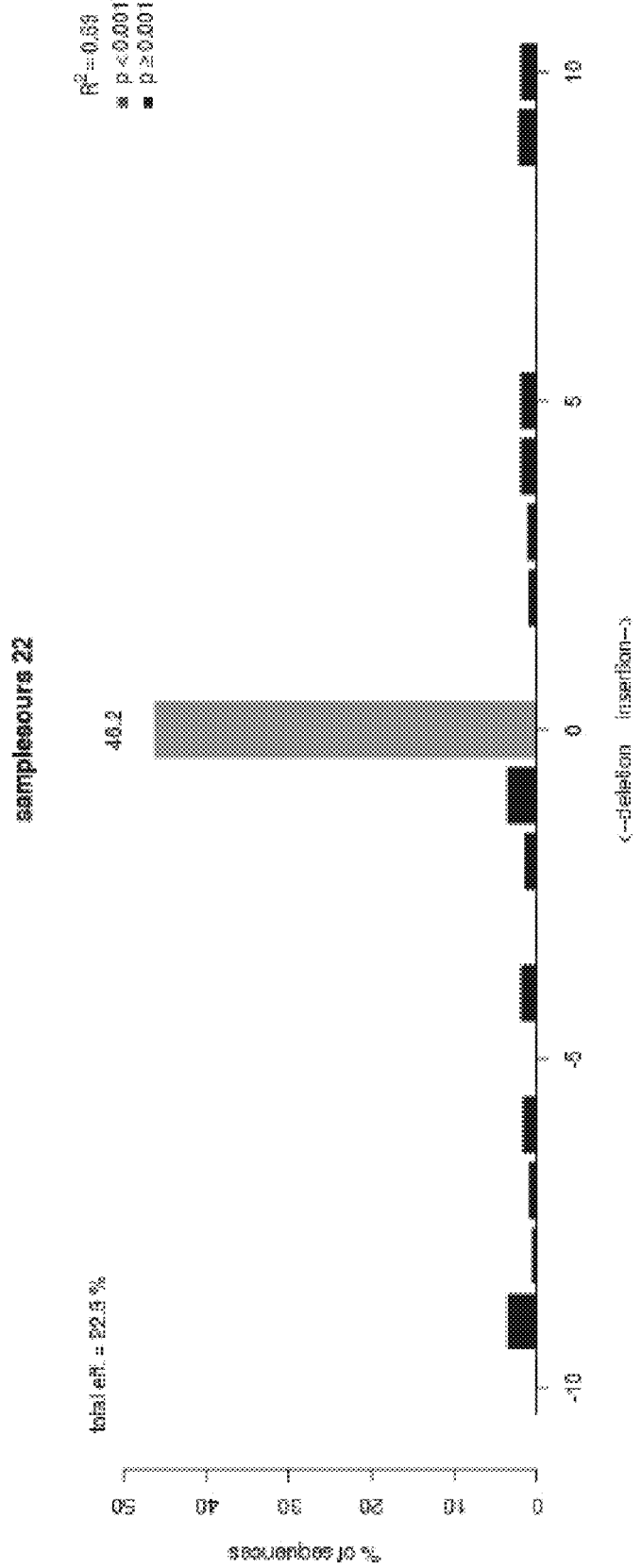

FIG. 15A-FIG. 15G: CRISPR delivery into Thy1-GFP mouse embryos by Cas9-containing virus-derived particles FIG. 15A illustrates the injection of CAS-containing virus-derived particles in the zona pellucida of Thy1-GFP mouse embryos.

FIG. 15B shows the results of cleaving the Thy1-GFP allele in the adult mice (F0) originating from the mouse embryos injected with CAS9-containing virus-derived particles FIG. 15C shows the alteration of the Thy1-GFP allele in the F1 mice originating from the F0 mice depicted in FIG. 15B.

FIG. 15D-FIG. 15G: Percent of GFP alteration in mice #78, #79, #21 and #22, respectively, as calculated from chromatograms wherein the results are compared with a non-treated Thy-GFP control mouse. In abscissa: percent of GFP alteration in F1 mice.

* % is never complete due to the fact that the chosen Thy1-GFP line carries several copies of GFP/allele (6 to 10). Results should be reproduced in a mouse line bearing one single constitutive GFP copy per allele, which is under preparation

DETAILED DESCRIPTION OF THE INVENTION

The present invention relates to the use of virus-derived particles to deliver CRISPR/Cas protein to target cells for generating targeted alteration(s) in the genome of an eukaryotic organism, preferably of a mammal, and especially of a human organism.

Surprisingly, the inventors have shown that the generation of a site-directed genome alteration, e.g. a site directed genome deletion or a site-directed genome insertion, may be successfully performed by delivering a Cas protein to the target cells through the use of viral vector particles wherein the said Cas protein has been packaged.

The present inventors have conceived a powerful method to transfer the CRISPRs active machinery within human and other mammalian cells, including primary cell types, by using versatile virus-derived particles (which are also termed "Virus Like Particles" or "VLPs" herein).

The inventors have shown that these VLPs ensure a transient and dose-dependent delivery of the CRISPR-RNPc (also termed "CRISPR-RiboNucleoProtein complex") into target cells and induce a robust and rapid cleavage of the desired targeted gene. As illustrated in the examples, when taking the Myd-88 gene as readout, the inventors have observed a complete cleavage of the latter gene in less than 6 hours in human cells, thus with a striking rapidity that may be attributed to the high efficiency of the virus-derived particles system described herein, which system comprises delivering directly a Cas protein, and most preferably a Cas9 protein, as well as CRISPR guide RNAs (also termed "gRNAs" herein) instead of performing a nucleic acid transfer of polynucleotides encoding Cas protein as it is the case for most already known CRISPRs delivery systems. As described in the examples herein, CRISPR guide RNAs are efficiently encapsulated in the CAS-containing VLPs. As it is also described in the examples, encapsulation of the CRISPR guide RNAs is highly subjected to the presence of the CAS protein in the VLPs.

The inventors have also shown that the CAS-containing VLPs may be prepared from a variety of virus-derived particles, and especially with virus-derived particles wherein the GAG protein contained therein may originate from a variety of viruses. Notably, it is described in the examples CAS-containing virus-derived particles comprising a MLV-derived GAG protein, as well as CAS-containing virus-derived particles comprising HIV1-derived GAG protein. It is shown herein that both kinds of CAS-containing virus-derived particles efficiently engineer a targeted gene, e.g., efficiently cleave a targeted gene.

Further, the inventors have shown that the GAG-containing virus-derived particles efficiently alter desired target sequences in vivo. Illustratively, it is shown in the examples that the GAG-containing virus-derived particles may be used to induce desired genomic alterations (e.g. induce a cleavage at a desired location in the genome) in living embryos. It is also shown herein that the genomic alterations performed in the living embryos are present in the resulting adult mammal and are then transferred to the subsequent generations.

The inventors findings are of a particular importance when considering that major gene expression processes (such as transcription and translation) are less active in some primary cells subsets that may be major targets for CRISPRs strategies and could therefore decrease the efficiency of conventional delivery methods like DNA transfection and conventional lentiviral vectors.

In this regard, the Cas9-virus-derived particles technology that has been conceived by the inventors appears as a tool of choice for genome editing, especially for genome editing in non-activated, non-dividing primary cells like lymphocytes, which poorly support transfection/transduction procedures, and display a low metabolism prior activation.

Further, according to the inventors results, the effect of the CRISPR RNPc is transient in the recipient target cell and is expected to exert its biological activity for at most a few hours after introduction of the RNPc through the contact of the virus-derived particles described herein with the target cells.

The transient delivery of CRIPSR components into target cells and the fact that this technology does not introduce plasmidic DNA in the target cells is expected to reduce the potential toxicity and also to reduce the risk of off-target cleavages.

Further, the fact that this technology does not introduce plasmidic DNA in the target cells allows avoiding the potential incorporation of exogenous-DNA in the target genome.

Illustratively, as it is shown in the examples, treatment of fragile human stem-CD34$^+$ cells or human lymphocytes with the virus-derived particles described herein has not induced detectable cell toxicity and has not led to cell-death, even after a massive input of the said virus-derived particles.

Notably, the present inventors have engineered a chimeric Cas9-protein upon fusion with the structural GAG protein of the murine leukemia virus to have the Cas9 protein packaged into MLV-derived VLPs or to HIV-1-derived VLPs.

This concept has thus been easily extended to other viral structural proteins like the GAG polyprotein from HIV-1 or the GAG polyprotein from Rous Sarcoma Virus (RSV) with success.

The virus-derived particles produced as described herein, are shown to efficiently transfer the CRISPR-RNPc into the desired target cells. Exploiting the technology of virus-derived particles described herein offers a large panel of viral envelopes that can be selected to pseudotype the said virus-derived particles, thus conferring particular properties to the preparation (tropism, complement resistance, robustness).

Insertion of the coding sequences of a Cas protein and one or more CRISPR gRNAs in expression cassettes, and especially the coding sequences of Cas9 and a specifically designed gRNA in expression cassettes, may also be performed in the backbone of recombinant viruses like Measles or certain Influenza strains, permissive to incorporation of foreign sequences. This allows an extensive diffusion of the active CRISPR RNPc in specific cells/tissues/organs permissive to the considered virus.

Beyond the exploitation of the Cas9 *Streptococcus pyogenes* endonuclease, the technology described herein is easily extended to Cas proteins from other organisms that can be alternatively fused with a structural viral protein. The growing cohort of Cas9-derivatives may also be delivered by the virus-derived particles described herein so as to achieve a large variety of genome alterations, such as cleaving only one DNA-strand, activating transcription and labelling precise genomic loci. The technology described herein also allows performing a Cas-based CRISPR strategy, especially a Cas9-based CRISPR strategy, for targeting intracellular mRNAs and induce their cleavage, as described by O'Connell et al. (2014, Nature, Vol. 516: 263-266), which is a technique involving small DNA sequences (PAMmers) provided in trans. The virus-derived particles technology described herein may be adapted to this RNA targeting approach by a simple combination of particles with ssDNA PAMmers on the model of the flagging-DDX3 strategy described in the examples (See also FIG. 10 herein).

The possibility to combine the virus-derived particles described herein, after their production, with ssDNA or even dsDNA offers vast possibilities in terms of industrial developments and rapid and costless customizations for various nucleic acid engineering purposes. Moreover, it is to note that viral-derived nanoparticles differing for their envelope or their proteic/nucleic cargo can trans-complement when combined as a mixture, as it was described in another technical context by Abe et al. (1998, J Virol, Vol. 72: 6356-6361).

A plurality of ways of combining the virus-derived particles of the invention and to transfer the CRISPRs effect into target cells are described elsewhere in the present specification. Some of these various embodiments are depicted in FIG. 11 herein. Preliminary data indicate that the virus-derived particles comprising a Cas protein, especially a Cas9 protein, may be combined with vesicles incorporating one or more CRISPR gRNA(s) when these virus-derived particles and vesicles are prepared and used as taught in another technical context by Mangeot et al. (2011, Mol Ther J Am Soc Gene Ther, Vol. 19: 1956-1666), and that the CRISPRs action is efficient in cells treated by the resulting mixture of the Cas-containing virus-derived particles and the gRNA(s)-containing vesicles. The opportunity to segregate the CRISPRs components in different types of particles may be of high interest from an industrial point of view and offers versatile technical solutions for generating the desired nucleic acid alteration(s).

The Cas-containing virus-derived particles described herein, especially the Cas9-containing virus-derived particles, may be easily produced in large amounts in the absence of gRNAs, to obtain VLP batches that are carefully dosed and quality-controlled. These Cas9-VLPs can later be combined in a custom-dependent manner with gRNA(s)-containing vesicles and/or targeting nucleic acid-containing vesicles, so as to complement the system by specific gRNAs or specific reparation template, or both.

As it is fully illustrated in the present specification, the Cas-containing virus-derived particles technology that is described herein offers new possibilities to the CRISPR community and notably upgrade the available toolbox to target challenging cell-types and explore innovative therapeutic CRISPR-based approaches for in ex vivo gene therapy.

Thus, the inventors have successfully packaged a Cas protein into virus-derived particles by conceiving packaging cells expressing a cleavable fusion protein between (i) a viral structural protein and (ii) the said Cas protein. Thus, the present invention relates to a virus-derived particle comprising one or more Cas protein(s).

As used herein, a virus-derived particle means a particle formed from the assembly of viral structural proteins which are associated so as to form the particle core that will be later enveloped with a membrane, (which virus-derived particle does not contain any nucleic acid encoding a nucleic acid or a protein of interest). Thus, in contrast to most of the virus-derived particles known in the art, which are designed for delivering expression nucleic acids in the transduced cells, a virus-derived particle as described herein is designed for delivering proteins, and optionally non-coding nucleic acids in the transduced cells, i.e. at least a Cas protein. As it is described in detail in the present specification, a virus-derived particle according to the invention may also contain one or more non-coding nucleic acids, which non-coding nucleic acids encompass CRISPR-Cas system guide RNA(s) and targeting nucleic acids. For the sake of clarity, it may arise that a virus-derived particle as described herein may contain traces of coding nucleic acids originating from the cells that are used for producing them, such as traces of mRNAs or plasmidic DNA originating from the said producing cells. The small amount of coding nucleic acids that may in some occasions be present within the virus-derived particles are generally passively encapsulated. However, it shall be clearly understood that the virus-derived particles described herein are not at all dedicated to transport any coding nucleic acid of interest but, as described in detail throughout the entire specification, these virus-derived particles are in contrast only dedicated to transport proteins, mainly one or more proteins having a Cas endonuclease activity, and in some embodiments also non-coding nucleic acids of interest, namely (i) one or more CRISPR-guide RNA(s) and/or one or more targeting nucleic acid(s).

As shown in the examples herein, the said cleavable fusion protein between (i) a viral structural protein and (ii) the said Cas protein is successfully incorporated in the virus-derived particles that are produced by the packaging cells and the resulting virus-derived particles successfully deliver the Cas protein to the target cells for altering the target cells genome through site-directed genomic DNA cleavage and, in some embodiments, also nucleic acid insertion by homologous recombination. As shown in the examples herein, the said fusion protein contributes to the formation of the virus-derived particles wherein it is associated with the viral structural proteins.

The inventors have notably shown that successful genomic alteration is obtained by using these virus-derived particles in combination with one or more CRIPSR-Cas system guide RNA(s), and in particular by using virus-derived particles further containing the said one or more CRIPSR-Cas system guide RNA(s) inside the said particles.

As shown in the examples, the virus-derived particles described herein have been successfully used for disrupting or deleting various genes, both in vitro and in vivo, so as to generate organisms wherein the said various genes have been knocked-out.

As it is also shown in the examples, the virus-derived particles described herein have been successfully used for the targeted insertion of nucleic acids of interest in the genome of target cells, so as to generate knock-in organisms.

As experimentally illustrated herein, the inventors have fused a Cas9 protein with the GAG protein of Murine Leukemia Virus and have used this construct to produce functional Cas9-loaded virus-derived particles delivering the Cas9 activity into recipient cells.

As further experimentally illustrated herein, the inventors have fused a Cas9 protein with the GAG protein of HIV-1 and have used this construct to produce functional Cas9-loaded virus-derived particles delivering the Cas9 activity into recipient cells.

Moreover it is shown in the examples herein that the guide RNAs can also be incorporated successfully in virus-derived particles, creating a fully active CRISPR-RNPc within viral like particles that can be transmitted into recipient cells. The experimental results of the inventors illustrate the high efficiency of these Cas-containing virus-derived particles. These virus-derived particles are fully able to deliver CRISPRs in different cells types, including primary cells, without apparent toxicity. Cleavage efficiency of the genomic target nucleic acid is remarkably close to 100% in human naive lymphocytes simply treated by the said virus-derived particles cleaving the human (hMyd88) gene.

The present invention relates to a virus-derived particle comprising one or more Cas protein(s). Various embodiments of the virus-derived particles described in the present specification are illustrated in FIG. 11.

Virus-Derived Particles

As used herein, a virus-derived particle consists of a virus-like particle formed by one or more virus-derived protein(s), which virus-derived particle is substantially devoid of any nucleic acid encoding a nucleic acid or a protein of interest, or alternatively is devoid of any nucleic acid encoding a nucleic acid or a protein of interest. Notably, a virus-derived particle according to the invention is substantially devoid of any nucleic acid encoding a viral nucleic acid or a viral protein of interest, or alternatively is devoid of any nucleic acid encoding a viral nucleic acid or a viral protein of interest. A virus-derived particle according to the invention is replication-incompetent.

Virus-Derived Particles

Any virus suitable for gene therapy may be used, including but not limited to adeno-associated virus ("AAV"); adenovirus; herpes virus; lentivirus and retrovirus. Adeno-associated virus ("AAV") may be selected in a group comprising AAV1, AAV6, AAV7, AAV8, AAV9 or rh10, which AAV are particularly suitable for use in human subjects.

The general methods that are known in the art for producing viral vector particles, which generally contain coding nucleic acids of interest, may also be used for producing the virus-derived particles according to the present invention, which do not contain coding nucleic acids of interest.

Conventional viral vector particles encompass retroviral, lentiviral, adenoviral and adeno-associated viral vector particles that are well known in the art. For a review of various viral vector particles that may be used, the one skilled in the art may notably refer to Kushnir et al. (2012, Vaccine, Vol. 31: 58-83), Zeltons (2013, Mol Biotechnol, Vol. 53: 92-107), Ludwig et al. (2007, Curr Opin Biotechnol, Vol. 18 (no 6): 537-55) and Naskalaska et al. (2015, Vol. 64 (no 1): 3-13). Further, references to various methods using virus-derived particles for delivering proteins to cells are found by the one skilled in the art in the article of Maetzig et al. (2012, Current Gene therapy, Vol. 12: 389-409) as well as the article of Kaczmarczyk et al. (2011, Proc Natl Acad Sci USA, Vol. 108 (no 41): 16998-17003).

Generally, a virus-derived particle that is used according to the invention, which virus-derived particle may also be termed "Virus-Like Particle" or "VLP", is formed by one or more virus-derived structural protein(s) and/or one more virus-derived envelope protein.

A virus-derived particle that is used according to the present invention is replication incompetent in a host cell wherein it has entered.

In preferred embodiments, a virus-derived particle is formed by one or more retrovirus-derived structural protein(s) and optionally one or more virus-derived envelope protein(s).

In preferred embodiments, the virus-derived structural protein is a retroviral gag protein or a peptide fragment thereof. As it is known in the art, Gag and Gag/pol precursors are expressed from full length genomic RNA as polyproteins, which require proteolytic cleavage, mediated by the retroviral protease (PR), to acquire a functional conformation. Further, Gag, which is structurally conserved among the retroviruses, is composed of at least three protein units: matrix protein (MA), capsid protein (CA) and nucleocapsid protein (NC), whereas Pol consists of the retroviral protease, (PR), the retrotranscriptase (RT) and the integrase (IN).

In some embodiments, a virus-derived particle comprises a retroviral Gag protein but does not comprise a Pol protein.

As it is known in the art, the host range of retroviral vector, including lentiviral vectors, may be expanded or altered by a process known as pseudotyping. Pseudotyped lentiviral vectors consist of viral vector particles bearing glycoproteins derived from other enveloped viruses. Such pseudotyped viral vector particles possess the tropism of the virus from which the glycoprotein is derived.

In some embodiments, a virus-derived particle is a pseudotyped virus-derived particle comprising one or more viral structural protein(s) or viral envelope protein(s) imparting a tropism to the said virus-derived particle for certain eukaryotic cells. A pseudotyped virus-derived particle as described herein may comprise, as the viral protein used for pseudotyping, a viral envelope protein selected in a group comprising VSV-G protein, Measles virus HA protein, Measles virus F protein, Influenza virus HA protein, Moloney virus MLV-A protein, Moloney virus MLV-E protein, Baboon Endogenous retrovirus (BAEV) envelope protein, Ebola virus glycoprotein and foamy virus envelope protein, or a combination of two or more of these viral envelope proteins.

A well-known illustration of pseudotyping viral vector particles consists of the pseudotyping of viral vector particles with the vesicular stomatitis virus glycoprotein (VSV-G). For the pseudotyping of viral vector particles, the one skilled in the art may notably refer to Yee et al. (1994, ProcNatl Acad Sci, USA, Vol. 91: 9564-9568) Cronin et al. (2005, Curr Gene Ther, Vol. 5 (no 4): 387-398).

For producing virus-derived particles, and more precisely VSV-G pseudotypes virus-derived particles, for delivering protein(s) of interest into target cells, the one skilled in the art may refer to Mangeot et al. (2011, Molecular Therapy, Vol. 19 (no 9): 1656-1666).

In some preferred embodiments, the VSV-G protein which is used for pseudotyping a virus-derived particle of the invention has the amino acid sequence of SEQ ID NO. 23, that may be encoded by a nucleic acid comprising the sequence of SEQ ID NO. 28.

In some preferred embodiments, the BAEV-G (BAEV) protein which is used for pseudotyping a virus-derived particle of the invention has the amino acid sequence of SEQ ID NO. 25, that may be encoded by a nucleic acid comprising the sequence of SEQ ID NO. 27.

Thus, in some embodiments, a virus-derived particle further comprises a viral envelope protein, wherein either (i) the said viral envelope protein originates from the same virus as the viral structural protein, e.g. originates from the same virus as the viral Gag protein, or (ii) the said viral envelope protein originates from a virus distinct from the virus from which originates the viral structural protein, e.g. originates from a virus distinct from the virus from which originates the viral Gag protein.

As it is readily understood by the one skilled in the art, a virus-derived particle that is used according to the invention may be selected in a group comprising Moloney murine leukemia virus-derived vector particles, Bovine immunodeficiency virus-derived particles, Simian immunodeficiency virus-derived vector particles, Feline immunodeficiency virus-derived vector particles, Human immunodeficiency virus-derived vector particles, Equine infection anemia virus-derived vector particles, Caprine arthritis encephalitis virus-derived vector particle, Baboon endogenous virus-derived vector particles, Rabies virus-derived vector particles, Influenza virus-derived vector particles, Norovirus-derived vector particles, Respiratory syncytial virus-derived vector particles, Hepatitis A virus-derived vector particles, Hepatitis B virus-derived vector particles, Hepatitis E virus-derived vector particles, Newcastle disease virus-derived vector particles, Norwalk virus-derived vector particles, Parvovirus-derived vector particles, Papillomavirus-derived vector particles, Yeast retrotransposon-derived vector particles, Measles virus-derived vector particles, and bacteriophage-derived vector particles.

In particular, a virus-derived particle that is used according to the invention is a retrovirus-derived particle. Such retrovirus may be selected among Moloney murine leukemia virus, Bovine immunodeficiency virus, Simian immunodeficiency virus, Feline immunodeficiency virus, Human immunodeficiency virus, Equine infection anemia virus, and Caprine arthritis encephalitis virus.

In another embodiment, a virus-derived particle that is used according to the invention is a lentivirus-derived particle. Lentiviruses belong to the retroviruses family, and have the unique ability of being able to infect non-dividing cells.

Such lentivirus may be selected among Bovine immunodeficiency virus, Simian immunodeficiency virus, Feline immunodeficiency virus, Human immunodeficiency virus, Equine infection anemia virus, and Caprine arthritis encephalitis virus.

For preparing Moloney murine leukemia virus-derived vector particles, the one skilled in the art may notably refer to the methods disclosed by Sharma et al. (1997, Proc Natl Acad Sci USA, Vol. 94: 10803+-10808), Guibingua et al. (2002, Molecular Therapy, Vol. 5 (no 5): 538-546). Moloney murine leukemia virus-derived (MLV-derived) vector particles may be selected in a group comprising MLV-A-derived vector particles and MLV-E-derived vector particles.

For preparing Bovine Immunodeficiency virus-derived vector particles, the one skilled in the art may notably refer to the methods disclosed by Rasmussen et al. (1990, Virology, Vol. 178 (no 2): 435-451)

For preparing Simian immunodeficiency virus-derived vector particles, including VSV-G pseudotyped SIV virus-derived particles, the one skilled in the art may notably refer to the methods disclosed by Mangeot et al. (2000, Journal of Virology, Vol. 71 (no 18): 8307-8315), Negre et al. (2000, Gene Therapy, Vol. 7: 1613-1623) Mangeot et al. (2004, Nucleic Acids Research, Vol. 32 (no 12), e102) For preparing Feline Immunodeficiency virus-derived vector particles, the one skilled in the art may notably refer to the methods disclosed by Saenz et al. (2012, Cold Spring Harb Protoc, (1): 71-76; 2012, Cold Spring Harb Protoc, (1): 124-125; 2012, Cold Spring Harb Protoc, (1): 118-123).

For preparing Human immunodeficiency virus-derived vector particles, the one skilled in the art may notably refer to the methods disclosed by Jalaguier et al. (2011, PlosOne, Vol. 6 (no 11), e28314), Cervera et al. (J Biotechnol, Vol. 166 (no 4): 152-165), Tang et al. (2012, Journal of Virology, Vol. 86 (no 14): 7662-7676) For preparing Equine infection anemia virus-derived vector particles, the one skilled in the art may notably refer to the methods disclosed by Olsen (1998, Gene Ther, Vol. 5 (no 11): 1481-1487).

For preparing Caprine arthritis encephalitis virus-derived vector particles, the one skilled in the art may notably refer to the methods disclosed by Mselli-Lakhal ety al. (2006, J Virol Methods, Vol. 136 (no 1-2): 177-184).

For preparing Baboon endogenous virus-derived vector particles, the one skilled in the art may notably refer to the methods disclosed by Girard-Gagnepain et al. (2014, Blood, Vol. 124 (no 8): 1221-1231) For preparing Rabies virus-derived vector particles, the one skilled in the art may notably refer to the methods disclosed by Kang et al. (2015, Viruses, Vol. 7: 1134-1152, doi:10.3390/v7031134), Fontana et al. (2014, Vaccine, Vol. 32 (no 24): 2799-27804) or to the PCT application published under no WO 2012/0618.

For preparing Influenza virus-derived vector particles, the one skilled in the art may notably refer to the methods disclosed by Quan et al. (2012, Virology, Vol. 430: 127-135) and to Latham et al. (2001, Journal of Virology, Vol. 75 (no 13),: 6154-6155).

For preparing Norovirus-derived vector particles, the one skilled in the art may notably refer to the methods disclosed by Tomé-Amat et al., (2014, Microbial Cell Factories, Vol. 13: 134-142).

For preparing Respiratory syncytial virus-derived vector particles, the one skilled in the art may notably refer to the methods disclosed by Walpita et al. (2015, PlosOne, DOI: 10.1371/journal.pone.0130755)

For preparing Hepatitis B virus-derived vector particles, the one skilled in the art may notably refer to the methods disclosed by Hong et al. (2013, Vol. 87 (no 12): 6615-6624).

For preparing Hepatitis E virus-derived vector particles, the one skilled in the art may notably refer to the methods disclosed by Li et al. (1997, Journal of Virology, Vol. 71 (no 10): 7207-7213).

For preparing Newcastle disease virus-derived vector particles, the one skilled in tha art may notably refer to the methods disclosed by Murawski et al. (2010, Journal of Virology, Vol. 84 (no 2): 1110-1123)

For preparing Norwalk virus-derived vector particles, the one skilled in the art may notably refer to the methods disclosed by Herbst-Kralovetz et al. (2010, Expert Rev Vaccines, Vol. 9 (no 3): 299-307).

For preparing Parvovirus-derived vector particles, the one skilled in the art may notably refer to the methods disclosed by Ogasawara et al. (2006, In Vivo, Vol. 20: 319-324)

For preparing Papillomavirus-derived vector particles, the one skilled in the art may notably refer to the methods disclosed by Wang et al. (2013, Expert Rev Vaccines, Vol. 12 (no 2): doi:10.1586/erv.12.151)

For preparing Yeast retrotransposon-derived vector particles, the one skilled in the art may refer to the methods disclosed by Peifang et al. (1994, Clin Exp Immunol, Vol. 97 (no 3): 361-366) or to the U.S. Pat. No. 6,060,064

For preparing Measles virus-derived vector particles, the one skilled in the art may notably refer to the methods disclosed by Brandler et al. (2008, Vol. 31 (no 2-3): 271-291).

For preparing bacteriophage-derived vector particles, and in particular Q-beta virus-like particles, the one skilled in the art may notably refer to the methods disclosed by Brown et al. (2009, Biochemistry, Vol. 48 (no 47): 11155-11157).

A virus-derived particle that is used herein comprises a Gag protein, and most preferably a Gag protein originating from a virus selected in a group comprising Rous Sarcoma Virus (RSV) Feline Immunodeficiency Virus (FIV), Simian Immunodeficiency Virus (SIV), Moloney Leukemia Virus (MLV) and Human Immunodeficiency Viruses (HIV-1 and HIV-2) especially Human Immunodeficiency Virus of type 1 (HIV-1).

In some embodiments, a virus-derived particle may also comprise one or more viral envelope protein(s). The presence of one or more viral envelope protein(s) may impart to the said virus-derived particle a more specific tropism for the cells which are targeted, as it is known in the art. The one or more viral envelope protein(s) may be selected in a group comprising envelope proteins from retroviruses, envelope proteins from non-retroviral viruses, and chimeras of these viral envelope proteins with other peptides or proteins. An example of a non-lentiviral envelope glycoprotein of interest is the lymphocytic choriomeningitis virus (LCMV) strain WE54 envelope glycoprotein. These envelope glycoproteins increase the range of cells that can be transduced with retroviral derived vectors.

In some preferred embodiments, the virus-derived particle comprises a Gag protein originating from a virus selected in a group comprising Rous Sarcoma Virus (RSV) and Moloney Leukemia Virus (MLV).

In some preferred embodiments, a virus-derived particle that is used herein, further comprises a pseudotyping viral envelope protein, and most preferably a VSV-G protein.

Cas Protein

A virus-derived particle comprises a Cas protein. The said Cas protein may be selected in a group comprising a type I Cas protein, a type II Cas protein and a type III Cas protein.

For using a type I, type II or type III Cas protein, the one skilled in the art may refer to Chylinski et al. (2014, Nucleic Acids Research, Vol. 42 (no 10): 6091-6105), Sinkunas et al. (2011, The EMBO Journal, Vol. 30 (no 7): 1335-1342), Aliyari et al. (2009, Immunological Reviews, Vol. 227 (no 1): 176-188), Cass et al. (Biosci Rep, doi:10.1042/BSR20150043), Makarova et al. (2011, Biology Direct, Vol. 6: 38), Gasiunas et al. (2012, Proc NatlAcad Sci USA, Vol. 109 (no 39): E2579-E2586), Heler et al. (2015, Nature, Vol. 519 (no 7542): 199-202), Esvelt et al. (2013, Nat Methods, Vol. 10 (no 11): doi:10.138/nmeth.2681) or Chylinski et al. (2013, Biology, Vol. 10 (no 5): 726-737).

In some embodiments, the Cas protein may consist of the Type II Cas protein named Cpf1 which is disclosed by Zeische et al. (2015, Cell, dx.doi.org/10.1016/j.cell.2015.09.038, in Press).

Preferably, a virus-derived protein comprises a type II Cas protein. A type II Cas protein is most preferably a Cas9 protein.

Most preferably, the Cas protein which is contained inside a virus-derived particle as described herein is a Cas9 protein, or an homolog or a derivative thereof. The Cas9 protein may be selected in a group comprising a Cas9 protein originating from *Streptococcus thermophilus* and a Cas9 protein originating from *Streptococcus pyogenes*, or an homolog thereof or a derivative thereof. Cas9 protein originating from *Streptococcus thermophilus* is described notably by Gasiunas et al. (2012, Proc NatlAcad Sci USA, Vol. 109 (no 39): E2579-E2586). Cas9 protein originating from *Streptococcus pyogenes* is described notably by Heler et al. (2015, Nature, Vol. 519 (no 7542): 199-202) and Sanjana et al. (2014, Nat Methods, Vol. 11 (no 18): 783-784).

A Cas9 protein that may be used according to the present invention encompasses proteins which are homologs, variants or derivatives of the naturally occurring Cas9 proteins, such as the Cas9 proteins described by Cong et al. (2013, Science, Vol. 339: 819-823).

A Cas9 protein as well as vectors encoding a Cas9 protein are commercially available from Sigma-Aldrich Company. Cas9 protein and variants thereof that may be used in virus-derived particles described herein are also described in the PCT applications published under no WO 2013/163628, WO 2014/093595, WO 2015/089247 and WO 2015/089486.

In some embodiments, Cas9 protein is produced so as to be incorporated in the virus-derived particles during their formation. Illustratively, Cas9 may be encoded by a nucleic acid sequence inserted in an expression vector contained in the virus-derived particles producing cells. In preferred embodiments, the Cas9-encoding nucleic acid is placed under the control of regulatory sequences allowing its overexpression in the producing cells. In some embodiments, the Cas9 protein consists of the protein of SEQ ID NO. 31, which is encoded by the nucleic acid sequence of SEQ ID NO. 32.

In some embodiments of a virus-derived particle described herein, the Cas protein is produced and integrated within the said virus-derived particle as a fusion protein between (i) a viral structural protein and (ii) the said Cas protein. In some of these embodiments, the Cas protein is produced and integrated within the said virus-derived particle as a GAG-Cas9 fusion protein. As it has been ascertained by the present inventors, such a fusion protein is successfully integrated within the resulting virus-derived particle and the Cas moiety is fully active, i.e. the Cas moiety possesses its endonuclease activity. According to those embodiments, the embedded Cas protein is released inside the target cells following the entering of the virus-derived particles.

In other embodiments, a Cas protein comprised in a virus-derived particle is initially produced as a cleavable fusion protein between (i) a viral structural protein and (ii) a Cas protein. An illustration of such a cleavable fusion protein is the cleavable GAG-Cas9 protein that is described in the examples herein. According to these other embodiments, the said cleavable fusion protein is integrated within the resulting virus-derived particle at the time of its production by the producing cells. Then, part or all of the said fusion proteins may be cleaved in the final virus-derived particles, leading to a population of virus-derived particles comprising (i) a part of the virus-derived particles wherein none the said cleavable fusion protein has been cleaved, (ii) a part of the virus-derived particles wherein at least a part of the said cleavable fusion proteins have been cleaved, leading the release of Cas protein moiety inside the virus-derived particles and (iii) a part of the virus-derived particles wherein all or almost all of the said cleavable fusion proteins have been cleaved, leading the release of all or almost all of the Cas protein moieties inside the virus-derived particles. In some preferred embodiments, a cleavable GAG-Cas9 protein is the GAG-Cas9 protein having the amino acid sequence of SEQ ID NO. 22, that may be encoded by a sequence of SEQ ID NO. 26. In other embodiments, it may be used a cleavable GAG-Cas9 protein encoded by the nucleic acid sequence of SEQ ID NO. 34 (that may be termed "KLAP229" herein).

Thus, in a virus-derived particle that may be used according to the invention, the Cas protein, typically the Cas9 protein, may be present either as (i) a non-cleavable fusion protein, typically a non-cleavable Gag-Cas9 fusion protein, as (ii) a cleavable fusion protein, typically a cleavable Gag-Cas9 fusion protein, as (iii) a Cas protein, typically a Cas9 protein, resulting from the proteolytic cleavage of the said fusion protein, or (iv) both the fusion protein and the Cas protein. It shall be understood that a virus-derived particle as used herein is produced in packaging cells that notably express a protein between (i) a viral structural protein and (ii) a Cas protein, typically a cleavable Gag-Cas9 fusion protein, which encompasses the cleavable fusion protein between (i) a viral structural protein and (ii) a Cas protein, typically the cleavable Gag-Cas9 fusion protein. The cleavable fusion protein is incorporated as such in the virus-derived particle and is then at least partly cleaved in the virus-derived particle so as to release the Cas protein, which is functional in the virus-derived particle as it is shown in the examples herein. However, because the Cas protein is initially incorporated in the virus-derived particles under the form of the said cleavable fusion protein, there are a number of intermediate states wherein the Cas protein is partly present under the form of the cleavable fusion protein and partly present as a free Cas protein resulting from the cleavage of the cleavable fusion protein.

In preferred embodiments, the fusion protein comprises a proteolysis cleavage site located between the viral structural protein moiety and the Cas protein moiety, typically between the Gag protein moiety and the Cas9 protein moiety. Proteolytic sites, which may also be termed protease sites, are well known form the one skilled in the art. A protease site that may be contained in the cleavable fusion protein may be a site that is cleavable by a protease selected in a group comprising trypsin (EC 3.4.21.4), chymotrypsin (EC 3.4.21.1), endoproteinase Glu C (EC 3.4.21.19), endoproteinase Lys-C (EC 3.4.21.50), pepsin (EC 3.4.23.1), elastase (EC 3.4.21.36) abd carboxypeptidase (EC 3.4.17.1).

In some embodiments, the protease cleavage site is selected in a group comprising the amino acid sequences SSLYPALTP (SEQ ID No 29), that may be encoded by a sequence comprising SEQ ID NO. 30.

Protease cleavable fusion protein between Gag and a protein of interest, as well as vectors for expressing such fusion proteins are notably described by Voelkel et al. (2010, Proc Natl Acad Sci USA, Vol. 107 (no 17): 7805-7810), to which the one skilled in the art may refer.

As described in the examples herein, some embodiments of a virus-derived particles are formed in packaging cells expressing a Gag-Pro-Pol viral protein. Without wishing to be bound by any particular theory, the inventors believe that in these embodiments, the Pro protein (i.e. the viral protease) is released in the virus-derived particles and cleaves the fusion protein, typically the Gag Cas fusion protein, especially the Gag-Cas9 fusion protein, so as to generate the free Cas protein, especially the free Cas9 protein. In some preferred embodiments, the Gag-Pro-Pol protein has the amino acid sequence of SEQ ID NO. 24.

However, as it is also illustrated in the examples herein, A functional Cas protein, typically a functional Cas9 protein, is released in the target cells in the embodiments wherein the virus-derived particles are devoid of any viral protease, e.g.; when the virus-derived particles are formed in packaging cells that express a viral structural protein (e.g. Gag) and optionally one or more viral envelope protein (e.g. VSV-G and/or BAEV-G).

Guide RNAs

For generating a site-directed alteration in a target nucleic acid, when using a virus-derived particle as described herein, one or more CRISPR-Cas guide RNAs are required.

The number of CRISPR-Cas guide RNAs, which may also be termed "guide RNAs" or "gRNAs", may vary depending of the kind of alteration(s) to the target nucleic acids which is(are) sought. A single guide RNA may be used in combination with a virus-derived particle for generating a single DNA cleavage event in the target nucleic acid. Two or more guide RNAs may be used in combination with a virus-derived particle for generating two or more cleavage events in the target nucleic acids, or alternatively to generate cleavage event(s) in a plurality of target nucleic acids.

Methods for designing guide RNAs that, when combined with a Cas protein, generate the cleavage of a target nucleic acid, are well known from the one skilled in the art. As it is well known in the art, a guide RNA is a polynucleotide having sufficient complementarity with a target nucleic acid to hybridize with the said target nucleic acid and direct sequence-specific binding of a CRISPR complex to the said target nucleic acid.

Various tools are readily available to the one skilled in the art for designing guide RNAs, which include the tool marketed under the name GenCRISPR™ gRNA constructs by the Company GenScript (United States). The GenCRISPR™ gRNA constructs collection comprise about six guide RNAs to specifically target each of about 20,000 genes in the human genome. Guide RNAs may also be designed according to the teachings of Ran et al. (2013, Cell, Vol. 154: 1380-1389), Mail et al. (2013, Science, Vol. 339: 823-826), Wang et al. (2013, Cell, Vol. 153: 910-918), Jao et al. (2013, Proc Natl Acad Sic USA, Vol. 110: 13904-13909), Cong et al. (2013, Science, Vol. 339: 819-823), Shalem et al. (2014, Science, Vol. 343: 84-87), Maeder et al. (2013, Nat Methods; Vol. 10: 977-979), Qi et al. (2013, Cell, Vol. 152: 1173-1183), Farboud et al. (2015, Genetics, doi 10.1534/genetics.115.175166) or Ma et al. (2013, BioMed research International, Vol. 2013, Article ID 270805, doi.org/10.1155/2013/270805).

In some embodiments, a virus-derived particle as described herein further comprises one or more CRISPR-Cas guide RNA(s). Each guide RNA hybridizes with a specific target sequence comprised in a target nucleic acid.

In some embodiments, a virus-derived particle as described herein comprises a single guide RNA. Such embodiments of a virus-derived particle allow generating a single cleavage at a desired location of the target nucleic acid.

In some other embodiments, a virus-derived particle as described herein comprises two distinct guide RNAs, each guide RNA hybridizing with a specific target sequence comprised in the same target nucleic acid, so as to generate two cleavage events at the sites recognized by the respective two distinct guide RNAs. Such embodiments allow introducing a deletion of the polynucleotide framed by the two cleavage sites within the target nucleic acid. When a template nucleic acid of interest is further added, such embodiments allow the insertion of a desired exogenous nucleic acid of interest in the nucleic acid target, between these two cleavage sites.

In some preferred embodiments, the one or more guide RNAs are comprised inside the virus-derived particle. Typically, the virus-derived particles are produced by packaging cells expressing (i) the required viral structural protein(s) (e.g. Gag), (ii) the one or more viral envelope protein(s) (e.g. VSV-G and/or BAEV-G), (iii) the Cas fusion protein (e.g. a Gag-Cas9 fusion protein) and (iv) the one or more CRISPR-Cas guide RNAs. According to these embodiments, the one or more guide RNAs are incorporated within the virus-derived particles while these are produced by the packaging cells. In these embodiments wherein the virus-derived particles comprise a Cas protein, especially a Cas9 protein, and one or more guide RNA(s), the said virus-derived particles comprise CRISPR-Cas ribonucleoprotein complexes which are complexes of the Cas protein with a guide RNA.

According to some of these embodiments, the said virus-derived particles comprise one or more kinds of complexes of a Cas protein and a guide RNA, wherein each CRISPR-Cas complex comprise a single Cas protein complexed with a single guide RNA. In some of these embodiments wherein a plurality of cleavages of a target nucleic acid is sought, the said virus-derived particles comprise the same number of kinds of CRISPR-Cas complexes, each kind of CRIPSR-Cas complex being specific for generating a DNA cleavage at a desired location of a target nucleic acid to which the corresponding guide RNA hybridize.

In further preferred embodiments, the one or more guide RNAs are initially produced by specific packaging cells expressing the said one or more guide RNAs and also expressing the viral protein(s) which are required for producing other viral particles or other viral vesicles (or other Virus-Like Particles or VLPs). Then, the guide RNA(s)-containing viral particles are brought into contact with a virus-derived particle comprising a Cas protein, so as to generate, by complementation, the final virus-derived particles comprising both a Cas protein and the one or more guide RNAs that were initially contained in the said other viral particles. for obtaining these virus-derived particles by complementation, the one skilled in the art may notably refer to Abe et al. (1998, Journal of Virology, Vol. 72 (no 8): 6356-6361). Illustratively, Gag-based Virus-derived particles comprising a Cas protein which are described herein may be brought into contact with VSV-G-based viral particles comprising one or more CRSIPS-Cas guide RNAs, so as to obtain final virus-derived particles comprising the said Cas protein and the said one or more CRISPR-Cas guide RNAs and wherein the said final virus-derived particles consist of VSV-G pseudotyped Gag-based VLPs.

In some other embodiments part of all of the said one or more guide RNAs are not comprised inside the virus-derived particles but are instead complexed with these virus-derived particles. According to these other embodiments, the guide RNAs which are complexed with the virus-derived particles also enter into the target cells with the virus-derived particles to which these guide RNAs are complexed.

Targeting Nucleic Acids

For the purpose of altering a target nucleic acid by using virus-derived particles as described herein, especially when an alteration of the target nucleic acid by homologous recombination is sought, it is further made use of a targeting nucleic acid in combination with these virus-derived particles.

Methods for targeting nucleic acids for the purpose of altering their sequence by homologous recombination are well known from the one skilled in the art. Typically, a homologous repair donor nucleic acid comprises (i) a first sequence that is homologous to a first locus of the targeted genomic sequence and (ii) a second sequence that is homologous to a second locus of the genomic sequence. Generally, for the purpose of altering a target nucleic acid by homologous recombination, the said first sequence (i) and the said second sequence (ii) are located at each side of the cleavage site created by the CRISPR-Cas/guide RNA(s) complex.

Methods for performing alterations in a target nucleic acid through homologous recombination by using a CRISPR-Cas system are well known in the art. The one skilled in the art may notably refer to Jinek et al. (2013, eLife, Vol. 2: e00471, doi: 10.754/eLife.00471) and Lin et al. (2014, eLife, Vol. 3: e04766, DOI:10.7554/eLife.04766).

Typically, an Homologous Recombination template nucleic acid, which may also be termed a template nucleic acid herein, comprises an exogenous sequence of variable length, flanked at its 5' and 3' ends, respectively, by sequences that hybridizes to the target nucleic acid. If the exogenous sequence that will be inserted in the genome is below 50 nt long, the flanking hybridizing sequences, also called homology recombination arms, should range from 20 to 50 nucleotides in length. If the exogenous sequence to insert is longer than 100 nt, the homology recombination arms should be considerably longer (around 800 bp).

The targeting nucleic acid, or template nucleic acid, may have any suitable length, such as about 10, 15, 20, 25, 50, 75, 100, 150, 200, 500, 1000 or more nucleotides in length. When optimally aligned, a targeting nucleic acid might overlap with one or more nucleotides of a target sequence, e.g. about or more than about 1, 5, 10, 15, 20 or more nucleotides.

Based on the general knowledge from the one skilled in the art, practically the sole requirement for designing a targeting nucleic acid for the purpose of homologous recombination is the prior knowledge of the nucleic sequence of the target nucleic acid.

In some embodiments, a targeting nucleic acid is comprised inside a virus-derived particle as described herein. According to these embodiments, the virus-derived particle comprising a Cas protein, one or more guide RNAs and one or more targeting nucleic acids are preferably produced by packaging cells that express the said Cas protein, the required viral proteins, the required guide RNAs and the requited targeting nucleic acid(s).

In some other embodiments, a targeting nucleic acid is not comprised inside the virus-derived particle but is complexed to the virus-derived particles.

Nucleic Acid Expression Vectors

As already stated elsewhere in the present specification, a virus-derived particle as described herein is produced in cells, also named packaging cells herein, which express the required proteins, i.e. at least a fusion viral structural protein/Cas protein and one or more viral proteins required for forming the viral particles, which may also be termed Virus-Like Particles or VLPs. In preferred embodiments, the packaging cells also express one or more CRISPR-Cas guide RNAs and, when necessary, also a targeting nucleic acid (also termed template nucleic acid).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in eukaryotic cells generally comprise promoters, enhancers, and termination and polyadenylation signals. In some embodiments, "expression vectors" are used in order to permit pseudotyping of the viral envelope proteins.

Generally, vectors for expressing the required proteins or nucleic acids are vector suitable for expressing nucleic sequences within the desired host cells that are used as packaging cells. Preferably, the packaging cells are mammalian cells. Notably, vectors for expressing the required proteins or nucleic acids comprise an open reading frame which is placed under the control of regulatory elements that are functional in the packaging cell wherein their expression is sought. Notably, these vectors comprise, for each protein or nucleic acid to be expressed, an open reading frame which is placed under the control of a suitable promoter sequence, as well as a polyadenylation sequence.

The packaging cell line provides the viral proteins required for particle assembly (Markowitz et al., 1988, J. Virol., Vol. 62:1120).

As it is well known in the art, a nucleic acid vector is introduced into the packaging cell by any of a variety of techniques (e.g., calcium phosphate co-precipitation, lipofection, electroporation). The viral proteins produced by the packaging cell mediate the insertion of the viral protein(s) and of the Cas protein into virus-derived particles, which are then released into the culture supernatant.

The nucleic acid vectors used may be derived from a retrovirus (e.g., a lentivirus). Retrovirus vectors suitable for producing the virus-derived particles described herein allow (1) transfection of the packaging vectors and envelope vectors into the host cell to form a packaging cell line that produces the virus-derived particles essentially free from packaging vector RNA, and (2) the packaging of the Cas protein and optionally also of the CRISPR guide RNA(s) and eventually of a targeting nucleic acid into the virus-derived particles.

Vectors and packaging cells for use according to the present invention are illustrated in the examples herein.

Illustratively, a vector for expressing the viral structural protein/Cas protein, e.g. a Gag-Cas9 protein, may be prepared by the one skilled in the art as taught by Voelkel et al. (2010, Proc Natl Acad Sci USA, Vol. 107: 7805-7810).

Illustratively, a vector for expressing the viral structural protein, e.g. a Gag protein or a Gag-Pro-Pol fusion protein, and optionally also a viral envelope protein, e.g. a VSV-G protein or a BAEV-G protein, may be prepared by the one skilled in the art according to the teachings of Negre et al. (2000, Gene Ther, Vol. 7: 1613-1623) and of Yee et al. (1994, Methods Cell Biol, Vol. 43 PtA: 99-112).

Illustratively, a vector for expressing a CRISPR guide RNA may be prepared as taught by Kieusseian et al. (2006, Blood, Vol. 107: 492-500).

Packaging Cells

The host cell is a cell into which a vector of interest may be introduced and wherein it may be replicated, and, in the case of an expression vector, in which one or more vector-based genes may be expressed.

Any suitable permissive or packaging cell known in the art may be employed in the production of the virus-derived particles described herein. Mammalian cells or insect cells are preferred. Examples of cells useful for the production of the virus-derived particles in the practice of the invention include, for example, human cell lines, such as VERO, WI38, MRC5, A549, HEK293, HEK293T, B-50 or any other HeLa cells, HepG2, Saos-2, HuH7, and HT1080 cell lines.

Illustrative cell lines for use as packaging cells are insect cell lines. Any insect cell which allows for replication of AAV and which can be maintained in culture can be used in accordance with the present invention. Examples include Spodoptera frugiperda, such as the Sf9 or Sf21 cell lines, Drosophila spp. cell lines, or mosquito cell lines, e.g., Aedes albopictus derived cell lines. A preferred insect cell line is the Spodoptera frugiperda Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, NJ (1995); O'Reilly et al., Baculovirus Expression Vectors: A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir. 219:37-44 (1996); Zhao et al., Vir. 272:382-93 (2000); and Samulski et al., U.S. Pat. No. 6,204,059.

The cells may be supplied with any one or more of the stated functions already incorporated, e.g., a cell line with one or more vector functions incorporated extra-chromosomally or integrated into the cell's chromosomal DNA, a cell line with one or more packaging functions incorporated extra-chromosomally or integrated into the cell's chromosomal DNA, or a cell line with helper functions incorporated extra-chromosomally or integrated into the cell's chromosomal DNA. A packaging cell line is a suitable host cell transfected by one or more nucleic acid vectors that, under achievable conditions, produces virus-derived particles comprising a Cas protein and, in some embodiments, also one or more CRIPSR guide RNA(s) and eventually also a targeting nucleic acid.

As used herein, the term "packaging cell lines" is typically used in reference to cell lines that express viral structural proteins (e.g., gag, pol and env), but do not contain a packaging signal. For example, a cell line has been genetically engineered to carry at one chromosomal site within its genome, a 5'-LTR-gag-pol-3'-LTR fragment that lacks a functional psi+ sequence (designated as A-psi), and a 5'-LTR-env-3'-LTR fragment that is also A-psi located at another chromosomal site.

A number of cell types can be used, which encompasses:
a) NIH-3T3 murine cells which are currently widely used as packaging cells producing recombinant retroviruses in clinical use (Takahara et al., Journal of Virology, (June 1992), 66 (6) 3725-32).
b) TK-cell lines have already been described, including NIH-3T3 TK cells (F. Wagner et al., EMBO Journal (1985), Vol. 4 (no 3): 663-666); these cells can be killed when they are cultivated in selective culture media such as HAT. If they are complemented for the kinase thymidine function, for example those from the HSV1-TK virus, they can grow in a selective medium; such lines thus offer the possibility of using the HSV1-TK gene as a selection gene. The gene coding for the thymidine kinase of HSV1 or one of its functional derivatives is also widely used as a transgene as a pro-drug transforming ganciclovir or acyclovir into a drug which is cytotoxic for the cell, and it can thus be applied to selective cell destruction, for example of cancerous cells (see, for example, International patent application WO 95/22617).

Illustratively, the packaging cells may be the well-known HEK293T cell line, as shown in the examples herein.

The present invention also relates to a cell line for producing a virus-derived particle as described herein, comprising:
one or more nucleic acids encoding the proteins required for forming the said virus-derived particle, and
a nucleic acid comprising an expression cassette encoding a viral structural protein-Cas fusion protein.

In some embodiments, a nucleic acid encoding a protein required for forming the said virus-derived particle encompasses a nucleic acid encoding a viral structural protein, such as a Gag protein.

In some embodiments, the said cell line also comprises a nucleic acid encoding a viral envelope protein, such as a viral envelope protein selected in a group comprising a VSV-G protein and a BAEV-G protein.

In some embodiments, the said cell line further comprises nucleic acid(s) encoding one or more CRISPR guide RNA(s).

In some embodiments, the said cell line further comprises nucleic acid(s) encoding one or more targeting nucleic acid(s).

Compositions and kits The present invention provides virus-derived particles compositions and kits suitable for use in therapy (in vivo or ex vivo) that are described herein.

In some embodiments, the said compositions comprise virus-derived particles comprising a Cas protein, especially a Cas9 protein, and is devoid of a guide RNA and of a targeting nucleic acid. In these embodiments, the gRNA(s) or the targeting nucleic acid are absent from the virus-derived particles, either as nucleic acids located inside the said virus-derived particles or as nucleic acids complexed with the said virus-derived particles.

The present invention relates to a composition for altering a target nucleic acid in a eukaryotic cell, which composition comprises at least one virus-derived particle as described in the present specification.

In some embodiments, the said composition further comprises one or more CRISPR-Cas system guide RNA(s).

In some of these embodiments, the said one or more CRISPR-Cas system guide RNA(s) is(are) comprised in virus-derived particles.

In some other embodiments, the said one or more CRISPR-Cas system guide RNA(s) is(are) complexed with the said virus-derived particles.

In some embodiments of the compositions, the said compositions comprise (i) Cas-containing virus-derived particles in combination with (ii) vesicles comprising gRNA(s) and/ or targeting nucleic acid(s). According to some of these embodiments, each gRNA present in the composition is comprised in a specific kind vesicles. According to some other of these embodiments, more than one gRNA, which includes all gRNA(s), are comprised in a specific kind of vesicles. In some of these embodiments, a targeting nucleic acid is comprised in a specific kind of vesicles. In some other of these embodiments, when more than one targeting nucleic acid is present in the composition, all the targeting nucleic acids are all comprised in a specific kind of vesicles. In still further embodiments, the whole gRNA(s) and targeting nucleic acid(s) present in the composition are all comprised in the same vesicles.

A "specific kind" of vesicle, as used herein is defined uniquely as regards its specific content in gRNA(s) and/or targeting nucleic acid(s), irrespective of the structural features of the vesicle itself.

Most preferably, the said vesicles are comprised of viral proteins. In some embodiments, the said vesicles have the same structural features of viral proteins as the virus-derived particles containing a Cas protein that are described in the present specification. In some other embodiments, the said vesicles are mainly or fully composed of viral envelope proteins, such as, for example, VSV-G or BAEV-G.

When present in a composition according to the invention, the Cas-containing virus-derived particles and the gRNA(s)- and/or targeting nucleic acid-containing vesicles trans-complement so as to efficiently generate the desired nucleic acid alteration(s) in the target cells. Such a trans-complementation in another technical context is taught by Mangeot et al. (2011, Ther J am Soc Gene Ther, Vol. 19: 1656-1666).

Compositions as described herein encompass pharmaceutical compositions that are used for the purpose of performing a method of gene therapy in mammals in need thereof, which includes non-human mammals and human individuals in need thereof.

Compositions of the invention may be formulated for delivery to animals for veterinary purposes (e.g., livestock such as cattle, pigs, etc), and other non-human mammalian subjects, as well as to human subjects. The virus-derived particles may be formulated with a physiologically acceptable carrier for use in gene transfer and gene therapy applications.

In some embodiments, the said composition further comprises one or more transduction helper compounds. The transduction helper compounds are preferably selected in a group comprising cationic polymers, as described notably by Zuris et al. (2015, Nat Biotechnol, Vol. 33 (no 1): 73-80).

The transduction helper compound may be selected in a group comprising polybrene (that may be also termed hexadimethrine bromide), protamine sulfate, 12-myristate 13-acetate (also termed phorbol myristate acetate or PMA, as described by Johnston et al., 2014, Gene Ther, Vol. 21(12): 1008-1020), vectofusin (as described by Fenard et al., 2013, Molecular Therapy Nucleic Acids, Vol. 2: e90), poloxamer P338 (as described by Anastasov et al., 2016, Lentiviral vectors and exosomes as gene and protein delivery tools, in Methods in Molecular Biology, Vol. 1448: 49-61), RetroNectin® Reagent (commercialized by Clontech Laboratories Inc.), Viral Plus® transduction enhancer (commercialized by Applied Biological Materials Inc.), TransPlus® Virus Transduction Enhancer (commercialized by Clinisciences), Lentiboost® (commercialized by Sirion Biotech), or ExpressMag® Transduction System (commercialized by Sigma-Aldrich). As shown in the examples herein, the said cationic transduction helper compound may consist of polybrene.

The virus-derived particles may be formulated in a conventional manner using one or more physiologically acceptable carriers or excipients. The virus-derived particles may be formulated for parenteral administration by injection, e.g., by bolus injection or continuous infusion. Formulations for injection may be presented in unit dosage form, e.g., in ampoules or in multi-dose containers, with an added preservative. The virus-derived particles compositions may take such forms as suspensions, solutions or emulsions in oily or aqueous vehicles, and may contain formulation agents such as suspending, stabilizing and/or dispersing agents. Liquid preparations of the virus-derived particles compositions may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts. Alternatively, the compositions may be in powder form for constitution with a suitable vehicle, e.g., sterile pyrogen-free water, before use.

The virus-derived particles compositions of the invention may be administered to a subject at therapeutically effective doses to generate the desired genome alteration in a target nucleic acid contained in a target cell, in a target tissue or organ or in a target organism, particularly a target mammal, which encompasses a target non-human mammal and a human individual. A therapeutically effective dose refers to an amount of the pharmaceutical composition sufficient to result in amelioration of symptoms caused by the occurrence of the desired genome alteration event in the target nucleic acid.

In an embodiment, an amount of virus-derived particles composition of the invention is administered at a dose unit that is in the range of about 0.1-5 micrograms (g)/kilogram (kg). To this end, a virus-derived particles composition of the invention may be formulated in doses in the range of about 7 mg to about 350 mg to treat to treat an average subject of 70 kg in body weight. The amount of virus-derived particles composition of the invention that may be administered may be selected in a group comprising 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg or 5.0 mg/kg. The dose of virus-derived particles in a unit dosage of the composition may be selected in a group comprising 7 mg, 8 mg, 9 mg, 10 mg, 20 mg, 25 mg, 30 mg, 35 mg, 40 mg, 45 mg, 50 mg, 55 mg, 60 mg, 65 mg, 70 mg, 75 mg, 80 mg, 85 mg 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg, especially for treating an average subject of 70 kg in body weight. These doses can be given once or repeatedly, such as daily, every other day, weekly, biweekly, or monthly. In some embodiments, a virus-derived particles composition may be administered to a subject in one dose, or in two doses, or in three doses, or in four doses, or in five doses, or in six doses or more. The interval between dosages may be determined based the practitioner's determination that there is a need thereof.

The virus-derived particles compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

A virus-derived particles composition may be in liquid or solid (e.g. lyophilized) form.

Kits

The present invention further relates to kits for preparing the virus-derived particles described in the present specification.

This invention concerns a kit for preparing virus-derived particles for altering a target nucleic acid in a eukaryotic cell comprising:
- a nucleic acid comprising an expression cassette encoding a GAG-Cas fusion protein, and
- a nucleic acid comprising one or more expression cassette(s) encoding virus-like assembly protein(s), In some embodiments, the said kit further comprises a nucleic acid comprising an expression cassette encoding a pseudotyping viral envelope protein.

In some embodiments of the said kit, the virus-derived assembly protein is a virus-derived Gag protein.

In some embodiments, the said Gag protein is encoded by an expression cassette selected in a group comprising an expression cassette encoding a GAG-PRO-POL polyprotein and an expression cassette encoding a GAG protein.

In some embodiments, the said kit further comprises one or more nucleic acid(s) encoding a CRISPR-Cas system guide RNA In certain embodiments of the said kit, the said nucleic acids are localized in an eukaryotic cell as a result of its transfection into the said eukaryotic cell. In some of these embodiments, the said nucleic acids are under the form of nucleic acid vectors in the said eukaryotic cells, which cells may also be termed packaging cells herein. In some other of these embodiments, part or all of these nucleic acids are integrated in the genome of these eukaryotic cells, which cells may also be termed packaging cells herein.

Thus, in some embodiments of a kit according to the invention, the said eukaryotic cell consists of a packaging cell line.

The kits of the present invention may optionally comprise different containers (e.g., vial, ampoule, test tube, flask or bottle) for each individual composition or element comprised therein. The kit may contain additional reagents, such as buffers, diluents and the like, for formulation the individual components. Each component will generally be suitable as aliquoted in its respective container or provided in a concentrated form.

Instructions for using the kit according to the methods described herein may be included. The instructional material may comprise a publication, a recording, a diagram, or any other medium of expression which can be used to communicate the usefulness of the method of the invention in the kit for assessment of oocyte quality. A package insert may comprise text housed in any physical medium, e.g., paper, cardboard, film, or may be housed in an electronic medium such as a diskette, chip, memory stick or other electronic storage form. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

Methods for Altering a Target Nucleic Acid

The virus-derived particles as well as the compositions comprising them may be used for gene therapy.

A further aspect of the invention is a method of treating subjects with the virus-derived particles according to the invention or with compositions comprising them.

Administration of the virus-derived particles to a human subject or an animal in need thereof can be by any means known in the art for administering virus vectors.

Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

This invention also relates to a method for altering a target nucleic acid comprising at least a target sequence in an eukaryotic cell, comprising the steps of:
a) bringing into contact the said eukaryotic cell with virus-derived particles as described herein, or with a composition as described in the present specification, and
b) collecting the said eukaryotic cell having an altered target nucleic acid.

In some embodiments, the virus-derived particles, or compositions comprising them, are administered directly to the subject, in vivo. In some other embodiments, subject's cells are provided, and then the said cells are transduced in vitro with the virus-derived particles, or with a composition comprising them. In a further method step, the transduced subject's cells are administered back to the body of the subject.

In some embodiments, said method is performed in vitro or ex vivo.

The present invention also relates to a composition as described in the present specification, for its use for preventing or treating any disease or disorder that is amenable to gene therapy.

The present invention provides for methods for preventing or treating any disease or disorder that is amenable to gene therapy. In one embodiment, "treatment" or "treating" refers to an amelioration of a disease or disorder, or at least one discernible symptom thereof. In another embodiment, "treatment" or "treating" refers to an amelioration of at least one measurable physical parameter associated with a disease or disorder, not necessarily discernible by the subject. In yet another embodiment, "treatment" or "treating" refers to inhibiting the progression of a disease or disorder, either physically, e.g., stabilization of a discernible symptom, physiologically, e.g., stabilization of a physical parameter, or both. Other conditions, including cancer, immune disorders, and veterinary conditions, may also be treated.

Types of diseases and disorders that can be treated by methods of the present invention include, but are not limited to, age-related macular degeneration; diabetic retinopathy; infectious diseases e.g., HIV pandemic flu, category 1 and 2 agents of biowarfare, or any new emerging viral infection;

autoimmune diseases; cancer; multiple myeloma; diabetes; systemic lupus erythematosus (SLE); hepatitis C; multiple sclerosis; Alzheimer's disease; parkinson's disease; amyotrophic lateral sclerosis (ALS), huntington's disease; epilepsy; chronic obstructive pulmonary disease (COPD); joint inflammation, arthritis; myocardial infarction (MI); congestive heart failure (CHF); hemophilia A; or hemophilia B.

Infectious diseases that can be treated or prevented by the methods of the present invention are caused by infectious agents including, but not limited to, viruses, bacteria, fungi, protozoa, helminths, and parasites. The invention is not limited to treating or preventing infectious diseases caused by intracellular pathogens. Many medically relevant microorganisms have been described extensively in the literature, e.g., see C. G. A Thomas, Medical Microbiology, Bailliere Tindall, Great Britain 1983, the entire contents of which are hereby incorporated herein by reference.

Types of cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

The present invention is further illustrated, without being in any way limited to, the examples below.

EXAMPLES

A. Materials and Methods
A.1. Constructs

The GAG-Cas9 coding plasmid was designed as described in (Voelkel et al., 2010). The codon-optimized sequence of flag-Cas9 from *Streptococcus pyogenes* was PCR-amplified using the lentiCRISPR plasmid (Addgene plasmid 4953) as a template. This last construct was a gift from F. Zhang laboratory (Shalem et al., 2014, Science, Vol. 343: 84-87). Flag-Cas9 was next inserted downstream the Murine Leukemia Virus GAG sequence (MA-CA-NC). Frames were harmonized to generate a polyprotein. Both moieties were separated by a MLV-protease cleavage site that releases flag-Cas9 from GAG during the viral maturation process. This chimeric protein was expressed under control of the hCMV promoter and is equipped with an intron and a poly A signal both derived from the rabbit beta-Globin mRNA. The expression plasmid encoding the GagProPol polyprotein of MLV (Négre et al., 2000, Gene Ther, Vol. 7: 1613-1623) and the VSVG coding plasmid (Yee et al., 1994, Methods Cell Biol, Vol. 43 PtA: 99-112) were described elsewhere. The gRNA coding plasmids termed as «CRIZI» derives from a previously described lentiviral construct (Kieusseian et al., 2006, Blood, Vol. 107: 492-500) in which was inserted the U6 cassette from the lentiCRISPR plasmid. Cloning of CRISPR gRNA sequences in CRIZI was performed between BsmBI sites upstream the U6 promoter following the procedure described by the authors. Sequences of gRNAs used in this study were designed using the Crispseek software (potential off-targets>3 mismatches) (Zhu et al., 2014, PloS One, Vol. 9: e108424). Primer sequences are given for each gRNA:

| YFP | |
|---|---|
| YFPgRNA1f | caccgCGAGGAGCTGTTCACCGGGG (SEQ ID NO. 1) |
| YFPgRNA1r | aaaCCCCGGTGAACAGCTCCTCGc (SEQ ID NO. 2) |
| YFPgRNA2f | caccgTCACCATACCGGTAGCCAGC (SEQ ID NO. 3) |
| YFPgRNA2r | aaacGCTGGCTaccggtATGGTGAc (SEQ ID NO. 4) |

| Myd88 | |
|---|---|
| hMyd88gRNA1f | caccgGAGACCTCAAGGGTAGAGGT (SEQ ID NO. 5) |
| hMyd88gRNA1r | aaacACCTCTACCCTTGAGGTCTCc (SEQ ID NO. 6) |
| hMyd88gRNA2f | caccgGCAGCCATGGCGGGCGGTCC (SEQ ID NO. 7) |
| hMyd88gRNA2r | aaacGGACCGCCCGCCATGGCTGCc (SEQ ID NO. 8) |
| mMyd88gRNA1f | caccggagcgtactggacggcaccg (SEQ ID NO. 9) |
| mMyd88gRNA1r | aaacggtgccgtccagtacgctcc (SEQ ID NO. 10) |
| mMyd88gRNA2f | caccggcccatctcctccgccagca (SEQ ID NO. 11) |
| mMyd88gRNA2r | aaactgctggcggaggagatgggcc (SEQ ID NO. 12) |

| DDX3 | |
|---|---|
| DDX3gRNA1f | CACCGAGGGATGAGTCATGTGGCAG (SEQ ID NO. 13) |
| DDX3gRNA1r | AAACCTGCCACATGACTCATCCCTC (SEQ ID NO 14) |

A.2. Production of VLPs

Cas9-VLP referred as a preparation of VLPs incorporating one of several gRNAs targeting a specific gene. Preparation of VLPs requires a cotransfection of several plasmids. VLPs were produced upon transfection of Lenti-X™ 293T (Clontech) using JetPei (Polyplus) following the manufacturer instructions. The JetPrime transfection agent (Polyplus) or the Calcium phosphate method (CalPhos mammalian kit, Clontech) may be used as well.

Classical ratio of the plasmids mixed in the JetPei transfection recipe are: GAG-Cas9 (20%), GagProPol (20%), VSV-G or other envelope (20%) and gRNAs encoding constructs (40%).

For Cas9Myd88VLPs, two different gRNA were introduced in the recipe to achieve copackaging of both RNA-species in the nascent VLPs. HEK293T cells plated at 3×10e6 cells/10 cm-plate 24h prior transfection were transfected with a mix containing:

R1: 4 ug of GAG-Cas9, 4 ug of GagProPol, 2 ug of VSVG, 2 ug of BaEV envelope (Girard-Gagnepain et al., 2014), 2 ug of Myd88-gRNA1 coding plasmid, 2 ug of Myd88-gRNA2 coding plasmid.

R2: 6 ug of GAG-Cas9, 6 ug of GagProPol, 4 ug of VSVG, 4 ug of Myd88-gRNA1 coding plasmid, 4 ug of Myd88-gRNA2 coding plasmid.

R3: 4 ug of GAG-Cas9, 8 ug of GagProPol, 2 ug of VSVG, 2 ug of BaEV envelope, 2 ug of Myd88-gRNA1 coding plasmid, 2 ug of Myd88-gRNA2 coding plasmid.

R4: 4-6 ug of GAG-Cas9, 2 ug of VSVG, 2 ug of BaEV envelope, 5 ug of Myd88-gRNA1 coding plasmid, 5 ug of Myd88-gRNA2 coding plasmid.

40 hours after transfection, VLP-containing supernatants were collected and clarified by a short centrifugation (2000 g, 3 min). Clarified Cas9-YFPVLPs were used directly to transduce L929 cells. Cas9-h-h/mMyd88VLPs and Cas9-DDX3VLPs were pelleted by ultracentrifugation 1h at 35000 rpm in a SW41-rotor and re-suspended in ice-cold PBS by overnight gentle agitation. 10 ml of supernatant were concentrated to produce 100 ul of concentrated VLPs in ice-cold PBS (concentration fold: 100x). Concentrated VLPs batches were stored at −80° C. and were shown to be stable at least 2 weeks at 4° C. after thawing. Filtration of VLP-containing supernatant can be performed with a 0.45 um-in-size pore filter before centrifugation/transduction.

A.3. ProteoTransduction Procedure Using Cas9-VLPs

3×10e5 L929-YFP cells were transduced with Cas9-YFPVLPs by addition of 400 ul of clarified VLP-containing supernatant in 400 ul of medium in a 6 well plate. After two hours, medium was supplemented with 2 ml of DMEM 10% FCS.

Transduction of primary cells was classically performed in 48-well plates upon addition of 5-20 ul of 100×VLPs in 300 ul of medium. After two hours, this transduction medium was supplemented by 0.5 ml of fresh culture medium. Polybrene addition was shown to potentialize proteotransduction when used at a final concentration of 4 ug/ml in the transduction medium.

A.4. PCR-Based Genotyping Assays

Genomic-DNA extraction of cells treated by VLPs was achieved using the Nucleospin Tissue Kit (Machery Nagel) according to the manufacturer instructions. DNA preparations were performed 24-48h after VLP-treatment but additional experiments indicate that cleavage was complete in HEK293T recipient cells as soon as 6h after exposure with VLPs.

PCR amplifications of Myd88 were performed in 50 ul using the GOTAQ polymerase (Promega). 100 ng of cellular genomic DNA was used as a template for a PCR reaction as follow: 94° C. 5 min, 3 cycles (94° C. 30 sec, 68° C. 30 sec), 3 cycles (94° C. 30 sec, 64° C. 30 sec, 72° C., 30 sec), 27 cycles (94° C. 30 sec, 57° C. 30 sec, 72° C. 30 sec), 72° C. 5 min, 12° C. PCR amplicons were analysed in Ethidium Bromide stained 2.5% agarose gels.

A.5. Primers Used for Genotyping Analysis (5'-NNN-3'):

| A.5. Primers used for genotyping analysis (5'-NNN-3'): | |
|---|---|
| YFP (surveyor assay) | |
| YFPf | tcTAATACGACTCACTATAGGGAGAGGTCTATATAAGCAGAGCTCGTTTAG (SEQ ID NO. 15) |
| YFPr | GGCCATGATATAGACGTTGTGGCTG (SEQ ID NO. 16) |

-continued

| A.5. Primers used for genotyping analysis (5'-NNN-3'): | |
|---|---|
| Myd88 | |
| hMyd88f2 | TTACGCCCCCCACATCACCCGCC (SEQ ID NO. 17) |
| hMyd88r1 | GTCTCCAGTTGCCGGATCTCCAAG (SEQ ID NO. 18) |
| mMyd88f2 | ggaaactccacaggcgagcgtac (SEQ ID NO. 19) |
| mMyd88r2 | ggcagtcctcctcgatgcgcgacttc (SEQ ID NO. 20) |

A.6. Combination of Cas9-DDX3VLPs with ssDNA 15 ul of concentrated Cas9-DDX3VLPs were mixed in 10 ul of PBS containing 8 ug/ml of polybrene. This mixture was next supplemented with 5 ul of each dilutions of the Flag-DDX3 primer, best results being obtained with the higher concentration (5 ul of primer at 100 pmol/ul). This 'all in one' complex was incubated 15 min at 4° C. and the 30 ul were added in the medium (400 ul+polybrene 4 ug/ml) of HEK293T cultivated in a 12-well-plate (200000 cells plated the day before). After two hours, the transduction medium was supplemented with 1 ml of DMEM 10% FCS. 40 hours after VLP-treatment, cells were splitted for amplification and analysis of the genetic insertion of the flag sequence upstream the DDX3 gene and WB analysis were performed 72 hours latter.

A.7. Sequence of the Flag-DDX3 Primer (HPLC-Purified):

(SEQ ID NO. 21)
5'-ACTCGCTTAGCAGCGGAAGACTCCGAGTTCTCGGTACTCTTCAGGGA

TGGACTACAAGGACGACGATGACAAGAGTCATGTGGCAGTGGAAAATGCG

CTCGGGCTGGACCAGCAGGTGA-3'

Example 1: Cleavage of the YFP gene by Cas9-YFPVLPs

Molecular engineering of viral structures allows the generation of viruses/VLPs that can incorporate a protein of interest. Amongst numerous examples can be cited the design of an HIV-1 clone incorporating a fluorescent gene allowing an easy monitoring of infection (Dale et al., 2011, Methods San Diego Calif, Vol. 53: 20-26), VLPs harboring viral epitopes useful for vaccination purposes in animal (Garrone et al., 2011, Sci Transl Med, Vol. 3: 94ra71), or VLPs used to deliver their proteic functionnal cargo in recipient cells (Voelkel et al., 2010, Proc Natl Acad Sci USA, Vol. 107: 7805-7810), (Mangeot et al., 2011, Mol Ther J Am Soc Gene Ther, Vol. 19: 1656-1666). To achieve the production of efficient Cas9-VLPs, Cas9 was fused to the structural GAG protein of murine Leukemia Virus (MLV) as previously described (Voelkel et al., 2010, Supra). Basically, expression of this chimeric protein with a viral protease (Pro) and an envelope in HEK293T cells is expected to produce VLPs incorporating a Cas9 moiety in their viral core, Cas9 being cleaved from the GAG platform by the viral protease.

Considering the affinity of Cas9 for gRNAs, we further assumed that expression of gRNAs in VLP-producing cells could be sufficient to allow their incorporation within particles which then would be able to vehicle all the components of the CRISPR machinery. To check these hypothesis, we designed gRNAs expressing plasmids to target the YFP gene and attempted to incorporate the gRNAs into Cas9-VLPs produced from HEK293T cells. A schema recapitulating this approach and the constructs used is depicted in FIG. 1. VLP-containing supernatants were next introduced in the medium of murine L929 cells expressing a stable version of YFP and cleavage of the fluorescent gene was next investigated by a surveyor assay. Results shown in FIG. 2 indicates that Cas9-VLPs delivered the CRISPR machinery and allowed the cleavage of the YFP gene at the expected position defined by the incorporated gRNA. This disruption of the gene was associated with a dramatic and irreversible loss of fluorescence in the treated population resulting from the expected rupture of the YFP-reading frame (FIG. 3). These observations validated the use of Cas9-VLPs as a potent delivery agent of the CRISPR components.

Example 2: Disruption of the Mvd88 Gene in HEK293T and Hela Recipient Cells

We further explored the capacity of VLPs to incorporate several gRNAs in order to mediate the deletion of the hMyd88 gene. Myd88 is a crucial adapter protein transmitting the signal of most TLRs to activate the transcription of nuclear factors and is notably implicated in the survival of macrophages in certain conditions (Lombardo et al., 2007, J Immunol Baltim Md 1950, Vol. 178: 3731-3739). Two gRNAs were designed to mediate two distinct cleavages in the human Myd88 gene resulting in a deletion of the endogenous gene (FIGS. 4A-B). Cas9-Myd88VLPs were produced upon transfection of different combinations of plasmids (described in Material and method). Released particles were next concentrated and used to alter the Myd88 gene in different recipient cells including Hela and HEK293T. Results shown FIGS. 4C and 4D indicate that all Cas9-VLPs types loaded with Myd88 gRNAs were efficient in deleting the expected portion of the Myd88 gene in HEK293T cells. However, Hela cells seemed more reluctant and were poorly modified by particular VLP species. Notably, we noted that VLPs devoid of protease (R4) were inefficient in Hela cells while remaining fully active in HEK293T target cells. These data suggest that the VLP recipe should be optimized for each targeted cell type. Additional experiments show that the effect of Cas9-Myd88VLPs was dose dependent (FIG. 5) and is potentiated by polybrene addition (FIG. 6).

Example 3: VLP-Mediated Disruption of the Mvd88 Gene in Primary Cells of Human and Murine Origin A more challenging issue is to deliver CRISPRs components into primary cells which are hardly permissive to conventional methods of transfection and may be difficult to transduce by viral vectors. Efficacy of Cas9-Myd88VLPs was thus monitored in different cell types freshly isolated from living organisms including human macrophages derived from human monocytes. Genotype analyses of treated cells reveals an obvious and very efficient cleavage of the Myd88 gene by a single administration of Cas9-Myd88VLPs in cultured macrophages (FIG. 7A). Beyond the genotype PCR-based assay which ascertains the cleavage of the gene, Myd88 disruption was responsible for a strong phenotype as revealed in FIG. 7B, confirming the inactivation of the Myd88 function. The amazing efficiency of VLPs to deliver CRISPRs in primary cells was further verified in human non activated-lymphocytes typically reluctant to most existing gene-modification techniques (FIG. 8). To generalize our observations, we designed another couple of gRNAs targeting the murine Myd88 gene and prepared a VLP batch dedicated to murine cells. This new VLP batch was used to deliver the CRISPRs RNPc in macrophages of murine origin with a high efficacy as indicated in FIG. 9. Altogether these results validate Cas9-VLPs as efficient agents to introduce the functional CRISPRs machinery in primary cells.

Example 4: Cas9-VLP can Mediate the Transfer of a Reparation Template: Generation of 'all in One' VLPs Complexes Previous works related the ability of MLV-derived VLPs and other VSV-G-induced particles to mediate the delivery of plasmids into human cells and to serve as viral-derived transfection agent. (Okimoto et al., 2001, Mol Ther J Am Soc Gene Ther, Vol. 4: 232-238). Since particles can be combined with dsDNA molecules, we reasoned that MLV-derived Cas9-VLPs could support a combination with ssDNA and mediate their delivery into cells. We took advantage of this knowledge and tried to combine Cas9-VLPs with a reparation primer composed of ssDNA. By this approach we propose to use VLPs to cleave an endogenous gene and to have it repaired in the cell by a homologous recombination-like mechanism (HR) using the provided reparation template. This was investigated using the DDX3 human gene as a model and a reparation primer designed to insert the FLAG sequence upstream of the ATG codon of the endogenous DDX3 gene. FIG. 10 depicts the principle of this 'All in one' VLP strategy that we have directly investigated both in transformed cells and primary cells. Cas9-DDX3VLPs combined with the Flag reparation primer successfully cleaved the DDX3 gene (not shown) and allowed the genetic targeted insertion of the flag sequence at the correct predicted site in the 5'-sequence of DDX3. This was checked by a PCR-based genotyping assay and the detection of the flagged DDX3 protein by Western Blot (FIG. 10C). This result was also verified at the genetic level in primary human dendritic cells exposed to a single treatment of Cas9-DDX3VLPs.

Example 5: Characterization of CAS9 Virus-Derived Particles

CAS9 VLPS were produced as disclosed in the Materials and Methods section and concentrated by a first Ultracentrifugation on a 20% sucrose cushion. Resulting pellet was next resuspended in PBS and recentrifuged on two sucrose cushions: a 50% sucrose cushion at the bottom of the tube and a 20%-sucrose cushion separating the 50% cushion from the sample. After 2h of centrifugation the interface separating the 50% and the 20% was harvested and recentrifuged to obtain highly pure CAS9-VLPs resuspended in PBS. 10 ug of VLPs were lysed in Laemlli buffer and heat at 95° C. during 5 min before western blot analysis.

Western blot analysis is represented in FIG. 12A (10 ug per lane). Antibodies used were directed againt GAGmlv (ABCAM R187), against VSVG (ABCAM P5D4), against CAS9 (7A9-3A3 clone Cell SIgnaling), against the Flag sequence engrafted on Cas9 (Sigma). Different forms of mlv GAG are revealed, corresponding to the cleaved products processed by the viral Protease. VSVG is clearly detected in the particle preparation at its expected size. CAS9 antibody reveals a higher product above 200KDa which corresponds to the GAG-CAS9 fusion (225 KDA expected), a protein that is also detected by the Flag antibody (left panel). Both CAS9 and FLAG antibodies reveals smaller CAS9 products (ranging from 160 to 200 KDa) that might corresponds to the free CAS9 protein or cleaved CAS9 products, released from GAG after protease processing.

As it is illustrated in FIG. 12B, 30 ug of total highly pure VLPs were loaded on a discontinuous sucrose gradient (10%-60% sucrose in PBS) in a total volume of 12 ml. After 16h of centrifugation (25000 rpm SW41), 500 ul fractions were collected from the top of the tube and named 1-24. 2 ul of each fraction were next spotted onto a nitrocellulose membrane immediately blocked by milk addition (TBST 5% low-fat Milk). Similar antibodies described above were next used to detect VSVG CAS9 and GAG MLV for each fractions. Results indicate that CAS9 VLPs sedimented at a density between 1.14 and 1.21 with a peak at 1.17.

Example 6: Loading of Guide RNAs in the CAS9 Virus-Derived Particles

Example 6 shows that the CAS9 virus-derived particles efficiently integrate guide RNAs. Northern blot directed against the conserved region of the guideRNA using total RNA extracted from producer cells (lanes 2 to 4) or the corresponding purified VLPs (lanes 5 to 7). Lane 1. Control sample corresponding to total RNA of cells that do not produce VLPs. Lane 2. Total RNA from cells expressing the Gag/Cas9 fusion, viral envelope and guideRNA. Lane 3. Total RNA from cells expressing the Gag/Cas9 fusion, viral envelope and a modified guideRNA with a longer stem structure. Lane4. Total RNA from cells expressing wild-type Cas9 and the guideRNA in absence of Gag. Lanes 5, 6 and 7. Total RNA extracted from the supernatant of the corresponding producer cells (Lane 5 corresponds to the supernatant of cells from lane 2 and so on) after clearing cellular debris and filtrating on a 0.8 m filter. Lane7 shows that when the Gag/Cas9 fusion is not expressed, the guideRNA is not efficiently incorporated within particles. Interestingly, the modified guideRNA with a longer stem structure (lanes 3 and 6) does not appear to be incorporated more efficiently into VLPs than the wild-type guideRNA (lanes 2 and 5).

Example 7: Comparison of MLV-Based Virus-Derived Particles with HIV-Based Virus-Derived Particles FIG. 14A illustrates a schematic representation of the coding cassettes designed for the production of MLV-based VLPs or HIV-1-based VLPs. Both cassettes were incorporated in an eucaryotic expression vector equipped with the early hCMV promoter, the rabbit-Bglobin intron and the rabbit pA signal. Both systems were optimized by exploration and test of diverse proteolytic sites separating the GAG cassette from the Cas9 gene. MLV based VLPs were produced as described in the Materials and Methods section while HIV-1 based VLPs were produced similarly except that an HIV-1 helper construct (construct of SEQ ID NO. 33) encoding GAG POL Tat Rev proteins was transfected instead of the MLV GAG POL plasmid. Production of HIV-1 VLPs follows the same procedure as compared with MLV-based VLPs.

FIG. 14B illustrates the test of concentrated VLPs engineered to incorporate a guide RNA targeting the GFP gene were used to transduce 30000 HEK293T cells expressing GFP. HIV-1 and MLV-based particles were produced with the same loaded gRNA (target sequence: CGAG-GAGCTGTTCACCGGGG—SEQ ID NO. 35). Recipient cells were plated the day before in a 96-w plate. Transduction medium was supplemented with polybrene (4 ug/ml). 72 hours after treatment with 3 increasing doses of each VLP-batch, fluorescence intensities were measured by a Fluorometer (Excitation 488, Emission 535). Fluorescence decrease was evident in VLPs-treated cells as compared with control non-treated cells (C), revealing the cleavage of the GFP gene within recipient cells. Results indicate that HIV-1 based VLPs are efficient in delivering the CRISPR/CAS9 system to a level slightly less efficient than MLV-based VLPs in these recipient cells (1.5-2 fold less efficient).

FIG. 14C illustrates the cleavage of the WASP gene in primary human T cells stimulated with IL7. For this experiment, two guide RNAs targeting the human WASP gene were incorporated within HIV-1 or MLV-based VLPs before treatment of freshly purified T-cells stimulated with IL7. WASP deletion by CRISPR-CAS9 was next measured by PCR in recipient cells 24 hours after treatment. Gel analysis performed using the ImageJ software allowed a quantification of double-cutting efficiencies for MLV-based VLPs (32%) and HIV-1-based VLPs (6%).

Example 8: CRISPR Delivery into Thy1-GFP Mouse Embryos by Cas9-Containing Virus-Derived Particles Cas9 VLPs incorporating a guide RNA targeting the GFP gene were produced and highly purified before injection into the zona pellucida of mouse embryos (stage 1-cell). Heterozygous embryos were all carrying the Thy1-GFP allele responsible for GFP expression in motoneurons. The aim of the study is to evaluate the capacity of VLPs to cleave GFP within embryos and to generate animals altered in their Thy1-GFP cassette after reimplantation of VLP-treated embryos into female mice. Few nanoliters of a preparation (6.5 uM Cas9) were used for two rounds of injections performed without performing the cell membrane as depicted in A. No embryo died upon this injection protocol. After reimplantion we obtained a total of 20 animals (F0). Genomic DNAs from newborns-fingers were extracted and analysed by a T7-endonuclease assay revealing the cleavage of the GFP cassette. As shown in B, 6 animals amongst 20 were positive for the assay (arrow) and 4/9 for the first injection experiment (left panel): animals 5,7,8,12 and animal 40 and 45 (weak) for the second injection. Animals 7 8 and 12 were next crossed with wt-C57B6 animals to evaluate the transmission of the cleaved GFP allele to descendants. Roughly half of the F1-descendance was noted to be heterozygous for the Thy1-GFP allele (for all 3 founders) as expected. The state of the Thy1-GFP allele in heterozygous F1 mice was next measured by a T7-endonuclease assay shown in C*.GFP was shown to be altered in all F1 heterozygous descendants of mice 7 and mice 12 and 33% of descendants of mice 8. Sequencing of the Thy1-GFP allele was next performed on the allele of animals #78 #79 #21 and #22 and chromatograms were compared to a sequence obtained for a Thy1-GFP non treated animal. TIDE software was used for this purpose and provided histograms describing the nature of indels for each animal and the % of sequence alteration. Results given in D E F and G indicate the % of GFP alteration in F1-mice*. Altogether these date show that Cas9-VLPs can assist animal transgenesis and be used as CRISPR-delivering agents to alter genes into mammal embryos without transfer of genetic material nor harming the egg-cell.

Protocol of T7-Endonuclease Assay:

Mouse genomic DNAs were extracted from mouse fingers using the Nucleospin Tissue Kit (Macherey Nagel). 3 ul of DNA template were next used in a 50 ul-PCR reaction (PCR conditions are: 95° C. 5 min followed by 3 cycles of (95° 30 sec-64° 30 sec-72° 30 sec) and 25 cycles of (95° 30 sec-57° 30 sec-72° 30 sec) followed by 5 min at 72° C. using primers:

```
                              (Thy1 primer-SEQ ID NO. 39)
    Forward:   5'-TCTGAGTGGCAAAGGACCTTAGG (GFP primer-SEQ ID NO. 40)
    Reverse:   5'-GAAGTCGTGCTGCTTCATGTGGTCGG
```

Thy1-GFP Amplicons were next submitted to the T7 endonuclease assay (NEB) as described by the manufacturer in a 40 ul reaction tube. (neb.com/protocols/2014/08/11/determining-genome-targeting-efficiency-using-t7-endonuclease-i) Digestions were finally loaded on a 2.5%-agarose gel.

** TIDE software is a free online tool: tide.nki.nl/. Chromatograms sequence (abi files) were uploaded into the software and the TIDE runs performed without modification of default settings. TIDE histograms are given

*** % is never complete due to the fact that the chosen Thy1-GFP line carries several copies of GFP/allele (6 to 10). Results should be reproduced in a mouse line bearing one single constitutive GFP copy per allele, which is under preparation.

Other sequences

GAG-Cas9 Amino acid sequence;

(SEQ ID NO. 22)

```
MGQAVTTPLSLTLDHWKDVERTAHNLSVEVRKRRWVTFCSAEWPTFNVGWPRDGTFNP
DIITQVKIKVFSPGPHGHPDQVPYIVTWEAIAVDPPPWVRPFVHPKPPLSLPPSAPSLPPEPP
LSTPPQSSLYPALTSPLNTKPRPQVLPDSGGPLIDLLTEDPPPYRDPGPPSPDGNGDSGEVA
PTEGAPDPSPMVSRLRGRKEPPVADSTTSQAFPLRLGGNGQYQYWPFSSSDLYNWKNNN
PSFSEDPAKLTALIESVLLTHQPTWDDCQQLLGTLLTGEEKQRVLLEARKAVRGEDGRPT
QLPNDINDAFPLERPDWDYNTQRGRNHLVHYRQLLLAGLQNAGRSPTNLAKVKGITQGP
NESPSAFLERLKEAYRRYTPYDPEDPGQETNVAMSFIWQSAPDIGRKLERLEDLKSKTLG
DLVREAEKIFNKRETPEEREERIRRETEEKEERRAEDVQREKERDRRRHREMSKLLATV
VSGQRQDRQGGERRRPQLDHDQCAYCKEKGHWARDCPKKPRGPRGPRPQASLLTRSSL
YPALTPTGDYKDDDDKMAPKKKRKVGIHGVPAADKKYSIGLDIGTNSVGWAVITDEYK
VPSKKFKVLGNTDRHSIKKNLIGALLFDSGETAEATRLKRTARRRYTRRKNRICYLQEIFS
NEMAKVDDSFFHRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLFEENPINASGVDA
KAILS ARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEHH
QDLTLLKALVRQQLPEKYKEIFFDQSKNGYAGYIDGGASQEEFYKFIKPILEKMDGTEELL
VKLNREDLLRKQRTFDNGSIPHQIHLGELHAILRRQEDFYPFLKDNREKIEKILTFRIPYYV
GPLARGNSRFAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIE
ERLKTYAHLFDDKVMKQLKRRRYTGWGRLSRKLINGIRDKQSGKTILDFLKSDGFANRN
FMQLIHDDSLTFKEDIQKAQVSGQGDSLHEHIANLAGSPAIKKGILQTVKVVDELVKVMG
RHKPENIVIEMARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDKNRGKSDNVP
SEEVVKKMKNYWRQLLNAKLITQRKFDNLTKAERGGLSELDKAGFIKRQLVETRQITKH
VAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSKES
ILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELAL
PSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQ
SITGLYETRIDLSQLGGDKRPAATKKAGQAKKKKARA
```

VSV-G Amino acid sequence :

(SEQ ID NO. 23)

```
MKCLLYLAFLFIGVNCKFTIVFPHNQKGNWKNVPSNYHYCPSSSDLNWHNDLIGTAIQV
KMPKSHKAIQADGWMCHASKWVTTCDFRWYGPKYITQSIRSFTPSVEQCKESIEQTKQG
TWLNPGFPPQSCGYATVTDAEAVIVQVTPHHVLVDEYTGEWVDSQFINGKCSNYICPTV
HNSTTWHSDYKVKGLCDSNLISMDITFFSEDGELSSLGKEGTGFRSNYFAYETGGKACK
MQYCKHWGVRLPSGVWFEMADKDLFAAARFPECPEGSSISAPSQTSVDVSLIQDVERILD
YSLCQETWSKIRAGLPISPVDLSYLAPKNPGTGPAFTIINGTLKYFETRYIRVDIAAPILSRM
VGMISGTTTERELWDDWAPYEDVEIGPNGVLRTSSGYKFPLYMIGHGMLDSDLHLSSKA
QVFEHPHIQDAASQLPDDESLFFGDTGLSKNPIELVEGWFSSWKSSIASFFFIIGLIIGLFLVL
RVGIHLCIKLKHTKKRQIYTDIEMNRLGK
```

GAG PRO POL Amino acid sequence :

(SEQ ID NO. 24)

```
MGQAVTTPLSLTLDHWKDVERTAHNLSVEVRKRRWVTFCSAEWPTFNVGWPRDGTFNP
DIITQVKIKVFSPGPHGHPDQVPYIVTWEAIAVDPPPWVRPFVHPKPPLSLPPSAPSLPPEPP
LSTPPQSSLYPALTSPLNTKPRPQVLPDSGGPLIDLLTEDPPPYRDPGPPSPDGNGDSGEVA
PTEGAPDPSPMVSRLRGRKEPPVADSTTSQAFPLRLGGNGQYQYWPFSSSDLYNWKNNN
PSFSEDPAKLTALIESVLLTHQPTWDDCQQLLGTLLTGEEKQRVLLEARKAVRGEDGRPT
QLPNDINDAFPLERPDWDYNTQRGRNHLVHYRQLLLAGLQNAGRSPTNLAKVKGITQGP
NESPSAFLERLKEAYRRYTPYDPEDPGQETNVAMSFIWQSAPDIGRKLERLEDLKSKTLG
DLVREAEKIFNKRETPEEREERIRRETEEKEERRAEDVQREKERDRRRHREMSKLLATV
VSGQRQDRQGGERRRPQLDHDQCAYCKEKGHWARDCPKKPRGPRGPRPQASLLTDDT
LDDQGGQGQEPPPEPRITLRVGGQPVTFLVDTGAQHSVLTQNPGPLSDKSAWVQGATGG
KRYRWTTDRRVHLATGKVTHSFLHVPDCPYPLLGRDLLTKLKAQIHFEGSGAQVVGPM
```

| Other sequences |
|---|
| GQPLQVLTLNIEDEYRLHETSKGPDVPLGSTWLSDFPQAWAETGGMGLAVRQAPLIIPLK<br>ATSTPVSIKQYPMSQEARLGIKPHIQRLLDQGILVPCQSPWNTPLLPVKKPGTNDYRPVQD<br>LREVNKRVEDIHPTVPNPYNLLSGLPPSHQWYTVLDLKDAFFCLRLHPTSQSLFAFEWRD<br>PEMGISGQLTWTRLPQGFKNSPTLFDEALHRDLADFRIQHPDLILLQYVDDLLLAATSELD<br>CQQGTRALLQTLGDLGYRASAKKAQICQKQVKYLGYLLKEGQRWLTEARKETVMGQP<br>TPKTPRQLREFLGTAGFCRLWIPGFAEMAAPLYPLTKTGTLFEWGPDQQKAYQEIKQALL<br>TAPALGLPDLTKPFELFVDEKQGYAKGVLTQKLGPWRRPVAYLSKKLDPVAAGWPPCL<br>RMVAAIAVLTKDAGKLTMGQPLVILAPHAVEALVKQPPDRWLSNARMTHYQALLLDTD<br>RVQFGPIVALNPATLLPLPEEGLQHDCLDILAEAHGTRPDLTDQPLPDADHTWYTDGSSF<br>LQEGQRKAGAAVTTETEVVWAKALPAGTSAQRAELIALTQALKMAEGKKLNVYTDSRY<br>APATAHIHGEIYRRRGLLTSEGKEIKNKDEILALLKALFLPKRLSIIHCPGHQKGNRAEARG<br>NRMADQAAREVATRETPETSTLLIENSAPYTHEHFHYTVTDIKDLTKLGATYDDAKKCW<br>VYQGKPVMPDQFTFELLDFLHQLTHLSFSKTKALLERNYCPYYMLNRDRTLKDITETCQ<br>ACAQVNASKSAVKQGTRVRGHRPGTHWEIDFTEVKPGLYGYKYLLVFIDTFSGWVEAFP<br>TKKETAKVVTKKLLEEIFPRFGMPQVLGTDNGPAFVSKVSQTVADLLGVDWKLHCAYRP<br>QSSGQVERMNRTIKETLTKLTLATGSRDWVLLLPLALYRARNTPGPHGLTPYEILYGAPP<br>PLVNFPDPDMAKVTHNPSLQAHLQALYLVQHEVWRPLAAAYQEQLDRPVVPHPFRVGD<br>TVWVRRHQTKNLEPRWKGPYTVLLTTPTALKVDGIAAWIHAAHVKAADTRIEPPSESTW<br>RVQRSQNPLKIRLTRGTS* |

BAEV-G Amino acid sequence (SEQ ID NO. 25)

```
MGFTTKIIFLYNLVLVYAGFDDPRKAIELVQKRYGRPCDCSGGQVSEPPSDRVSQVTCSG
KTAYLMPDQRWKCKSIPKDTSPSGPLQECPCNSYQSSVHSSCYTSYQQCRSGNKTYYTA
TLLKTQTGGTSDVQVLGSTNKLIQSPCNGIKGQSICWSTTAPIHVSDGGGPLDTTRIKSVQ
RKLEEIHKALYPELQYHPLAIPKVRDNLMVDAQTLNILNATYNLLLMSNTSLVDDCWLC
LKLGPPTPLAIPNFLLSYVTRSSDNISCLIIPPLLVQPMQFSNSSCLFSPSYNSTEEIDLGHVA
FSNCTSITNVTGPICAVNGSVFLCGNNMAYTYLPTNWTGLCVLATLLPDIDIIPGDEPVPIP
AIDHFIYRPKRAIQFIPLLAGLGITAAFTTGATGLGVSVTQYTKLSNQLISDVQILSSTIQDL
QDQVDSLAEVVLQNRRGLDLLTAEQGGICLALQEKCCFYVNKSGIVRDKIKTLQEELERR
RKDLASNPLWTGLQGLLPYLLPFLGPLLTLLLLLTIGPCIFNRLTAFINDKLNIIHAM
```

GAGmlv-CAS9 sequence :

(SEQ ID NO. 26)

```
ATGGGCCAGGCTGTTACCACCCCCTTAAGTTTGACTTTAGACCACTGGAAGGATGTCGAACGGACAGCCCACA
ACCTGTCGGTAGAGGTTAGAAAAAGGCGCTGGGTTACATTCTGCTCTGCAGAATGGCCAACCTTCAACGTCGG
ATGGCCACGAGACGGCACTTTTAACCCAGACATTATTACACAGGTTAAGATCAAGGTCTTCTCACCTGGCCCAC
ATGGACATCCGGATCAGGTCCCCTACATCGTGACCTGGGAAGCTATAGCAGTAGACCCCCCTCCCTGGGTCAG
ACCCTTCGTGCACCCTAAACCTCCCCTCTCTCTTCCCCCTTCAGCCCCTCTCTCTCCCACCTGAACCCCCACTCTCGA
CCCCGCCCCAGTCCTCCCTCTATCCGGCTCTCACTTCTCCTTTAAACACCAAACCTAGGCCTCAAGTCCTTCCTGA
TAGCGGAGGACCACTCATTGATCTACTCACGGAGGACCCTCCGCCTTACCGGGACCCAGGGCCACCCTCTCCT
GACGGGAACGGCGATAGCGGAGAAGTGGCCCCTACAGAAGGAGCCCCTGACCCTTCCCCAATGGTATCCCGC
CTGCGGGGAAGAAAGAACCCCCCGTGGCGGATTCTACTACCTCTCAGGCGTTCCCCCTTCGCCTGGGAGGGA
ATGGACAGTATCAATACTGGCCATTTTTCCTCCTCTGACCTCTATAACTGGAAGATAACAACCCCTCTTTCTCCG
AGGACCCAGCTAAATTGACAGCTTTGATCGAGTCCGTTCTCCTTACTCATCAGCCCACTTGGGATGACTGCCAA
CAGCTATTAGGGACCCTGCTGACGGGAGAAGAAAAACAGCGAGTGCTCCTAGAGGCCCGAAAGGCGGTTCG
AGGGGAGGACGGACGCCCAACTCAGCTGCCCAATGACATTAATGATGCTTTTCCCTTGGAACGTCCCGACTGG
GACTACAACACCCAACGAGGTAGGAACCACCTAGTCCACTATCGCCACCAGTTGCTCCTAGCGGGTCTCCAAAACG
CGGGCAGAAGCCCCCACCAATTTGGCCAAGGTAAAAGGGATAACCCAGGGACCTAATGAGTCTCCCTCAGCCTT
TTTAGAGAGACTCAAGGAGGCCTATCGCAGATACACTCCTTATGACCCTGAGGACCCAGGGCAAGAAACCAAT
GTGGCCATGTCATTCATCTGGCAGTCCGCCCCgGATATCGGGCGAAAGTTAGAGCGGTTAGAAGATTTGAAGA
GTAAGACCTTAGGAGACTTAGTGAGGGAAGCTGAAAAGATCTTTAATAAACGGAAAGCCCCGGAAGAAAGAG
AGGAACGTATTAGGAGAGAAACAGAGGAAAAGGAAGAACGCCGTAGGGCAGAGGATGTGCAGAGAGAGAA
GGAGAGGGACCGCAGAGACATAGAGAAATGAGTAAGTTGCTGGCTACTGTCGTTAGCGGGCAGAGACAGG
ATAGACAGGGAGGAGAGCGAAGGAGGCCCCAACTCGACCACGACCAGTGTGCCTACTGCAAAGAAAGGGA
CATTGGGCTAGAGATTGCCCCAAGAAGCCAAGAGGACCCCGGGGACCCACGAGCCCCCAGGCCTCCCTCCTGacgc
gtagttccctgtatccagccctcacacctaccggtGATTACAAAGACGATGACGATAAGATGGCCCCAAAGAAGAAGCGGA
AGGTCGGTATCCACGGAGTCCCAGCAGCCGACAAGAAGTACAGCATCGGCCTGGACATCGGCACCAACTCTG
TGGGCTGGGCCGTGATCACCGACGAGTACAAGGTGCCCAGCAAGAAATTCAAGGTGCTGGGCAACACCGACC
GGCACAGCATCAAGAAGAACCTGATCGGAGCCCTGCTGTTCGACAGCGGCGAAACAGCCGAGGCCACCCGGC
TGAAGAGAACCGCCAGAAGAAGATACACCAGACGGAAGAACCGGATCTGCTATCTGCAAGAGATCTTCAGCA
ACGAGATGGCCAAGGTGGACGACAGCTTCTTCCACAGACTGGAAGAGTCCTTCCTGGTGGAAGAGGATAAGA
AGCACGAGCGGCACCCCATCTTCGGCAACATCGTGGACGAGGTGGCCTACCACGAGAAGTACCCCACCATCTA
CCACCTGAGAAAGAAACTGGTGGACAGCACCGACAAGGCCGACCTGCGGCTGATCTATCTGGCCCTGGCCCA
CATGATCAAGTTCCGGGGCCACTTCCTGATCGAGGGCGACCTGAACCCCGACAACAGCGACGTGGACAAGCT
GTTCATCCAGCTGGTGCAGACCTACAACCAGCTGTTCGAGGAAAACCCCATCAACGCCAGCGGCGTGGACGCC
AAGGCCATCCTGTCTGCCAGACTGAGCAAGAGCAGACGGCTGGAAAATCTGATCGCCCAGCTGCCCGGCGAG
AAGAAGAATGGCCTGTTCGGCAACCTGATTGCCCTGAGCCTGGGCCTGACCCCCAACTTCAAGAGCAACTTCG
ACCTGGCCGAGGATGCCAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCCATCCTGCTGAGCGACAT
CCTGAGAGTGAACACCGAGATCACCAAGGCCCCCCTGAGCGCCTCTATGATCAAGAGATACGACGAGCACCAC
CAGGACCTGACCCTGCTGAAAGCTCTCGTGCGGCAGCAGCTGCCTGAGAAGTACAAAGAGATTTTCTTCGACC
AGAGCAAGAACGGCTACGCCGGCTACATTGACGGCGGAGCCAGCCAGGAAGAGTTCTACAAGTTCATCAAGC
CCATCCTGGAAAAGATGGACGGCACCGAGGAACTGCTCGTGAAGCTGAACAGAGAGGACCTGCTGCGCAAG
CAGCGGACCTTCGACAACGGCAGCATCCCCCACCAGATCCACCTGGGAGAGCTGCACGCCATTCTGCGGCGGC
AGGAAGATTTTTACCCATTCCTGAAGGACAACCGGGAAAAGATCGAGAAGATCCTGACCTTCCGCATCCCCTA
```

-continued

Other sequences

CTACGTGGGCCCTCTGGCCAGGGGAAACAGCAGATTCGCCTGGATGACCAGAAAGAGCGAGGAAACCATCAC
CCCCTGGAACTTCGAGGAAGTGGTGGACAAGGGCGCTTCCGCCCAGAGCTTCATCGAGCGGATGACCAACTTC
GATAAGAACCTGCCCAACGAGAAGGTGCTGCCCAAGCACAGCGTGCTGTACGAGTACTTCACCGTGTATAACG
AGCTGACCAAAGTGAAATACGTGACCGAGGGAATGAGAAAGCCCGCCTTCCTGAGCGGCGAGCAGAAAAAG
GCCATCGTGGACCTGCTGTTCAAGACCAACCGGAAAGTGACCGTGAAGCAGCTGAAAGAGGACTACTTCAAG
AAAATCGAGTGCTTCGACTCCGTGAAATCTCCGGCGTGGAAGATCGGTTCAACGCCTCCCTGGGCACATACC
ACGATCTGCTGAAAATTATCAAGGACGACTTCCTGGACAATGAGGAAAACGAGGACATTCTGGAAGATA
TCGTGCTGACCCTGACACTGTTTGAGGACAGAGAGATGATCGAGGAACGGCTGAAAACCTATGCCCACCTGTT
CGACGACAAAGTGATGAAGCAGCTGAAGCGGCGGAGATACACCGGCTGGGGCAGGCTGAGCCGGAAGCTGA
TCAACGGCATCCGGGACAAGCAGTCCGGCAAGACAATCCTGGATTTCCTGAAGTCCGACGGCTTCGCCAACAG
AAACTTCATGCAGCTGATCCACGACGACAGCCTGACCTTTAAAGAGGACATCCAGAAAGCCCAGGTGTCCGGC
CAGGGCGATAGCCTGCACGAGCACATTGCCAATCTGGCCGGCAGCCCCGCCATTAAGAAGGGCATCCTGCAG
ACAGTGAAGGTGGTGGACGAGCTCGTGAAAGTGATGGGCCGGCACAAGCCCGAGAACATCGTGATCGAAAT
GGCCAGAGAGAACCAGACCACCCAGAAGGGACAGAAGAACAGCCGCGAGAGAATGAAGCGGATCGAAGAG
GGCATCAAAGAGCTGGGCAGCCAGATCCTGAAAGAACACCCCGTGGAAAACACCCAGCTGCAGAACGAGAA
GCTGTACCTGTACTACCTGCAGAATGGGCGGGATATGTACGTGGACCAGGAACTGGACATCAACCGGCTGTCC
GACTCGATGTGGACCATATCGTGCCTCAGAGCTTTCTGAAGGACGACTCCATCGACAACAAGGTGCTGACCA
GAAGCGACAAGAACCGGGGCAAGAGCGACAACGTGCCCTCCGAAGAGGTCGTGAAGAAGATGAAGAACTAC
TGGCGGCAGCTGCTGAACGCCAAGCTGATTACCCAGAGAAAGTTCGACAATCTGACCAAGGCCGAGAGAGGC
GGCCTGAGCGAACTGGATAAGGCCGGCTTCATCAAGAGACGGCTGGTGGAAACCCGGCAGATCACAAAGCAC
GTGGCACAGATCCTGGACTCCGGATGAACACTAAGTACGACGAGAATGACAAGCTGATCCGGGAAGTGAAA
GTGATCACCCTGAAGTCCAAGCTGGTGTCCGATTTCCGGAAGGATTTCCAGTTTTACAAAGTGCGCGAGATCA
ACAACTACCACCACGCCCACGACGCCTACCTGAACGCCGTCGTGGGAACCGCCCTGATCAAAAAGTACCCTAA
GCTGGAAAGCGAGTTCGTGTACGGCGACTACAAGGTGTACGACGTGCGGAAGATGATCGCCAAGAGCGAGC
AGGAAATCGGCAAGGCTACCGCCAAGTACTTCTTCTACAGCAACATCATGAACTTTTTCAAGACCGAGATTACC
CTGGCCAACGGCGAGATCCGGAAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAGTGAATATCGTGAAAAAGACCGA
GGTGCAGACAGGCGGCTTCAGCAAAGAGTCTATCCTGCCCAAGAGGACAGCGATAAGCTGATCGCCAGAAA
GAAGGACTGGGACCCTAAGAAGTACGGCGGCTTCGACAGCCCCACCGTGGCCTATTCTGTGCTGGTGGTGGC
CAAAGTGGAAAAGGGCAAGTCCAAGAAACTGAAGAGTGTGAAAGAGCTGCTGGGGATCACCATCATGGAAA
GAAGCAGCTTCGAGAAGAATCCCATCGACTTTCTGGAAGCCAAGGGCTACAAAGAAGTGAAAAAGGACCTGA
TCATCAAGCTGCCTAAGTACTCCCTGTTCGAGCTGGAAAACGGCCGGAAGAGAATGCTGGCCTCTGCCGGCGA
ACTGCAGAAGGGAAACGAACTGGCCCTGCCCTCCAAATATGTGAACTTCCTGTACCTGGCCAGCCACTATGAG
AAGCTGAAGGGCTCCCCCGAGGATAATGAGCAGAAACAGCTGTTTGTGGAACAGCACAAGCACTACCTGGAC
GAGATCATCGAGCAGATCAGCGAGTTCTCCAAGAGAGTGATCCTGGCCGACGCTAATCTGGACAAAGTGCTGT
CCGCCTACAACAAGCACCGGGATAAGCCCATCAGAGAGCAGGCCGAGAATATCATCCACCTGTTTTACCCTGAC
CAATCTGGGAGCCCCTGCCGCCTTCAAGTACTTTGACACCACCATCGACCGGAAGAGGTACACCAGCACCAAA
GAGGTGCTGGACGCCACCCTGATCCACCAGAGCATCACCGGCCTGTACGAGACACGGATCGACCTGTCTCAGC
TGGGAGGCGACAAGCGTCCTGCTGCTACTAAGAAAGCTGGTCAAGCTAAGAAAAAGAAAGCTAGAGCTTGA

BAEV-G Baboon envelope RLESS variant BAEVRless: (also noted BRL in the
text and figures) referenced in Girard-GagnepainAet al. 2014. Blood. 2014
Aug 21 ;124(8):1221 -31. doi: 10.1182/blood-2014-02-558163. Epub 2014 Jun
20).

SEQ ID NO. 27 atgggctttaccaccaagattattttctgtataacctggtgctggtgtatgcgggctttgatgatccgcgcaaagcgattgaactggtgcagaaac
gctatggccgccgtgcgattgcagcggcggccaggtgagcgaaccgccgagcgatcgcgtgagccaggtgacctgcagcggcaaaaccgcgt
atctgatgccggatcagcgctggaaatgcaaaagcattccgaaagataccagcccgagcggcccgctgcaggaatgcccgtgcaacagctatc
agagcagcgtgcatagcagctgctataccagctatcagcagtgccgcagcggcaacaaaacctattataccgcgaccctgctgaaaaacccagac
cggcggcaccagcgatgtgcaggtgctgggcagcaccaacaaactgattcagagcccgtgcaacgcattaaaggccagagcatttgctggag
cacca ccgcgccgattcatgtgagcgatggcggcggcccgctggataccacccgcattaaaagcgtgcagcgcaaactggaagaaattcataa
agcgctgtatccggaactgcagtatcatccgctggcgattccgaaagtgcgcgataaacctgatggtggatgcgcagaccctgaacattctgaacg
cgacctataacctgctgctgatgagcaacaccagcctggtgattgctggctggtgaaactgggccccgccgaccccgctggcgattccg
aactttctgctgagctatgtgacccgcagcagcgataacattagctgcctgattattccgcgcgctgctggtgcagccgatgcagtttagcaacagc
agctgcctgtttagcccgagctataacagcaccgaagaaattgatctgggccatggcgtttagcaactgcaccagcattaccaacgtgaccgg
cccgatttgcgcggtgaacggcagcgtgtttctgtgcggcaacaacatggcgtatacctatctgccgaccaactggaccggcctgtgcgtgctggc
gaccctgctgccggatattgatattattccgggcgatgaaccggtgccgattccggcgattgatcatttatttatcgcccgaaacgcgcgattcag
tttattccgctgctggcggcctgggcattaccgcggcgtttaccaccgcgaccggcctgggcgtgagcgtgaccagtatacccaaactgag
caaccagctgattagcgatgtgcagattctgagcagcaccattcaggatctgcaggatcaggtggatagcctggcggaagtggtgctgcagaac
cgccgcggcctggatctgctgaccgcggaacagggcggcatttgcctggcgctgcaggaaaaatgctgcttttatgtgaacaaaagcggcattgt
gcgcgataaaattaaaccctgcaggaagaactggaacgccgccgcaaagatctggcgagcaacccgctgtggaccggcctgcagggcctgct
gccgtatctgctgccgtttctgggcccgctgctgaccctgctgctgctgctgaccattggcccgtgcattttttaaccgcctgaccgcgtttattaacga
taaactgaacattattcatgcgatgtaa VSV-G sequence:

(SEQ ID NO 28)
ATGAAGTGCCTTTTGTACTTAGCCTTTTTATTCATTGGGGTGAATTGCAAGTTCACCATAGTTTTTCCACACAAC
CAAAAAGGAAACTGGAAAAATGTTCCTTCTAATTACCATTATTGCCCGTCAAGCTCAGATTTAAATTGGCATAA
TGACTTAATAGGCACAGCCTTACAAGTCAAATGCCCAAGAGTCACAAGGCTATTCAAGCAGACGGTTGGATG
TGTCATGCTTCCAAATGGGTCACTACTTGTGATTTCCGCTGGTATGGACCGAAGTATATAACACATTCCATCCG
ATCCTTCACTCCATCTGTAGAACAATGCAAGGAAAGCATTGAACAAGAAACAAGGCCATTGCAGACGGCGGTTGGAT
GGCTTCCTCCTCAAAGTTGTGGATATGCAACTGTGACGGATGCCGAAGCAGTGATTGTCCAGGTGACTCCTC
ACCATGTGCTGGTTGATGAATACACAGGAGAATGGGTTGATTCACAGTTCATCAACGGAAAATGCAGCAATTA
CATATGCCCCACTGTCCATAACTCTACAACCTGGCATTCTGACTATAAGGTCAAGGGCTATGTGATTCTAACCCT
CATTTCCATGGACATCACCTTCTTCTCAGAGGACGGAGAGCTATCATCCCTGGGAAAAGGAGGGCACAGGGTTC
AGAAGTAACTACTTTGCTTATGAAACTGGAGGCAAGGCCTGCAAAATGCAATACTGCAAGCATTGGGGAGTCA
GACTCCCATCAGGTGTCTGGTTCGAGATGGCTGATAAGGATCTCTTTGCTGCAGCCAGATTCCCTGAATGCCCA

| Other sequences |
|---|
| GAAGGGTCAAGTATCTCTGCTCCATCTCAGACCTCAGTGGATGTAAGTCTAATTCAGGACGTTGAGAGGATCTT<br>GGATTATTCCCTCTGCCAAGAAACCTGGAGCAAAATCAGAGCGGGTCTTCCAATCTCTCCAGTGGATCTCAGCT<br>ATCTTGCTCCTAAAAACCCAGGAACCGGTCCTGCTTTCACCATAATCAATGGTACCCTAAAATACTTTGAGACCA<br>GATACATCAGAGTCGATATTGCTGCTCCAATCCTCTCAAGAATGGTCGGAATGATCAGTGGAACTACCACAGA<br>AAGGGAACTGTGGGATGACTGGGCACCATATGAAGACGTGGAAATTGGACCCAATGGAGTTCTGAGGACCA<br>GTTCAGGATATAAGTTTCCTTTATACATGATTGGACATGGTATGTTGGACTCCGATCTTCATCTTAGCTCAAAGG<br>CTCAGGTGTTCGAACATCCTCACATTCAAGACGCTGCTTCGCAACTTCCTGATGATGAGAGTTTATTTTTTGGTG<br>ATACTGGGCTATCCAAAAATCCAATCGAGCTTGTAGAAGGTTGGTTCAGTAGTTGGAAAAGCTCTATTGCCTCT<br>TTTTTCTTTATCATAGGGTTAATCATTGGACTATTCTTGGTTCTCCGAGTTGGTATCCATCTTTGCATTAAATTAA<br>AGCACACCAAGAAAAGACAGATTTATACAGACATAGAGATGAACCGACTTGGAAAGTAA |

| Cleavage site: |
|---|

Amino acid: SSLYPALTP (SEQ. ID NO 29)

Nucleic acid: agttccctgtatccagccctcacacct (SEQ ID NO 30)

Cas9 Amino acid sequence (SEQ ID NO. 31)

MAPKKKRKVGIHGVPAADKKYSIGLDIGTNSVGWAVITDEYKVPSKKFKVLGNTDRHSIKKNLIGALLFDSGETAEAT
RLKRTARRRYTRRKNRICYLQEIFSNEMAKVDDSFFHRLEESFLVEEDKKHERHPIFGNIVDEVAYHEKYPTIYHLRKKL
VDSTDKADLRLIYLALAHMIKFRGHFLIEGDLNPDNSDVDKLFIQLVQTYNQLFEENPINASGVDAKAILSARLSKSRR
LENLIAQLPGEKKNGLFGNLIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKHSLLYEYFTVYNELTKVKYVTEGMRKP
AFLSGEQKKAIVDLLFKTNRKVTVKQLKEDYFKKIECFDSVEISGVEDRFNASLGTYHDLLKIIKDKDFLDNEENEDILED
IVLTLTLFEDREMIEERLKTYAHLFDDKVMKQLKRRRYTGWGRLSRKLINGIRDKQSGKTILDFLKSDGFANRNFMQL
IHDDSLTFKEDIQKAQVSGQGDSLHEHIANLAGSPAIKKGILQTVKVVDELVKVMGRHKPENIVIEMARENQTTQKG
QKNSRERMKRIEEGIKELGSQILKEHPVENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNLTKAERGGLSELDKAGFIKRQLVETRQI
TKHVAQILDSRMNTKYDENDKLIREVKVITLKSKLVSDFRKDFQFYKVREINNYHHAHDAYLNAVVGTALIKKYPKLE
SEFVYGDYKVYDVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKGKSKKLKSVK
ELLGITIMERSSFEKNPIDFLEAKGYKEVKKDLIIKLPKYSLFELENGRKRMLASAGELQKGNELALPSKYVNFLYLASHY
EKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGDKRPAATKKAGQAKKKKA

Cas9 Nucleic acid sequence (SEQ ID NO. 32)

ATGGCCCCAAAGAAGAAGCGGAAGGTCGGTATCCACGGAGTCCCAGCAGCCGACAAGAAGTACAGCATCGG
CCTGGACATCGGCACCAACTCTGTGGGCTGGGCCGTGATCACCGACGAGTACAAGGTGCCCAGCAAGAAATT
CAAGGTGCTGGGCAACACCGACCGGCACAGCATCAAGAAGAACCTGATCGGAGCCCTGCTGTTCGACAGCGG
CGAAACAGCCGAGGCCACCCGGCTGAAGAGAACCGCCAGAAGAAGATACACCAGACGGAAGAACCGGATCT
GCTATCTGCAAGAGATCTTCAGCAACGAGATGGCCAAGGTGGACGACTTCTTCCACAGACTGGAAGAGTC
CTTCCTGGTGGAAGAGGATAAGAAGCACGAGCGGCACCCCATCTTCGGCAACATCGTGGACGAGGTGGCCTA
CCACGAGAAGTACCCCACCATCTACCACCTGAGAAAGAAACTGGTGGACAGCACCGACAAGGCCGACCTGCG
GCTGATCTATCTGGCCCTGGCCCACATGATCAAGTTCCGGGGCCACTTCCTGATCGAGGGCGACCTGAACCCC
GACAACAGCGACGTGGACAAGCTGTTCATCCAGCTGGTGCAGACCTACAACCAGCTGTTCGAGGAAAACCCA
TCAACGCCAGCGGCGTGGACGCCAAGGCCATCCTGTCTGCCAGACTGAGCAAGAGCAGACGGCTGGAAAATC
TGATCGCCCAGCTGCCCGGCGAGAAGAAGAATGGCCTGTTCGGCAACCTGATTGCCCTGAGCCTGGGCCTGAC
CCCCAACTTCAAGAGCAACTTCGACCTGGCCGAGGATGCCAAACTGCAGCTGAGCAAGGACACCTACGACGAC
GACCTGGACAACCTGCTGGCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCCCCTGAGCGCCTCTATGAT
CAAGAGATACGACGAGCACCACCAGGACCTGACCCTGCTGAAAGCTCTCGTGCGGCAGCAGCTGCCTGAGAA
GTACAAAGAGATTTTCTTCGACCAGAGCAAGAACGGCTACGCCGGCTACATTGACGGCGGAGCCAGCCAGGA
AGAGTTCTACAAGTTCATCAAGCCCATCCTGGAAAAGATGGACGGCACCGAGGAACTGCTCGTGAAGCTGAAC
AGAGAGGACCTGCTGCGGAAGCAGCGGACCTTCGACAACGGCAGCATCCCCCACCAGATCCACCTGGGAGAG
CTGCACGCCATTCTGCGGCGGCAGGAAGATTTTTACCCATTCCTGAAGGACAACCGGGAAAAGATCGAGAAG
ATCCTGACCTTCCGCATCCCCTACTACGTGGGCCCTCTGGCCAGGGGAAACAGCAGATTCGCCTGGATGACCA
GAAAGAGCGAGGAAACCATCACCCCCTGGAACTTCGAGGAAGTGGTGGACAAGGGCGCTTCCGCCCAGAGCT
TCATCGAGCGGATGACCAACTTCGATAAGAACCTGCCCAACGAGAAGGTGCTGCCCAAGCACAGCCTGCTGTA
CGAGTACTTCACCGTGTATAACGAGCTGACCAAAGTGAAATACGTGACCGAGGGAATGAGAAAGCCCGCCTTC
CTGAGCGGCGAGCAGAAAAAGGCCATCGTGGACCTGCTGTTCAAGACCAACCGGAAAGTGACCGTGAAGCAG
CTGAAAGAGGACTACTTCAAGAAAATCGAGTGCTTCGACTCCGTGGAAATCTCCGGCGTGGAAGATCGGTTCA
ACGCCTCCCTGGGCACATACCACGATCTGCTGAAAATTATCAAGGACAAGGACTTCCTGGACAATGAGGAAAA
CGAGGACATTCTGGAAGATATCGTGCTGACCCTGACACTGTTTGAGGACAGAGAGATGATCGAGGAACGGCT
GAAAACCTATGCCCACCTGTTCGACGACAAAGTGATGAAGCAGCTGAAGCGGCGGAGATACACCGGCTGGGG
CAGGCTGAGCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAAGAGGACATC
CAGAAAGCCCAGGTGTCCGGCCAGGGCGATAGCCTGCACGAGCACATTGCCAATCTGGCCGGCAGCCCCGCC
ATTAAGAAGGGCATCCTGCAGACAGTGAAGGTGGTGGACGAGCTCGTGAAAGTGATGGGCCGGCACAAGCC
CGAGAACATCGTGATCGAAATGGCCAGAGAGAACCAGACCACCCAGAAGGGACAGAAGAACAGCCGCGAGA
GAATGAAGCGGATCGAAGAGGGCATCAAAGAGCTGGGCAGCCAGATCCTGAAAGAACACCCCGTGGAAAAC
ACCCAGCTGCAGAACGAGAAGCTGTACCTGTACTACCTGCAGAATGGGCGGGATATGTACGTGGACCAGGAA
CTGGACATCAACCGGCTGTCCGACTACGATGTGGACCATATCGTGCCTCAGAGCTTTCTGAAGGACGACTCCAT
CGACAACAAGGTGCTGACCAGAAGCGACAAGAACCGGGGCAAGAGCGACAACGTGCCCTCCGAAGAGGTCG

-continued

Other sequences

TGAAGAAGATGAAGAACTACTGGCGGCAGCTGCTGAACGCCAAGCTGATTACCCAGAGAAAGTTCGACAATC
TGACCAAGGCCGAGAGAGGCGGCCTGAGCGAACTGGATAAGGCCGGCTTCATCAAGAGACAGCTGGTGGAA
ACCCGGCAGATCACAAAGCACGTGGCACAGATCCTGGACTCCCGGATGAACACTAAGTACGACGAGAATGAC
AAGCTGATCCGGGAAGTGAAAGTGATCACCCTGAAGTCCAAGCTGGTGTCCGATTTCCGGAAGGATTTCCAGT
TTTACAAAGTGCGCGAGATCAACAACTACCACCACGCCCACGACGCCTACCTGAACGCCGTCGTGGGAACCGC
CCTGATCAAAAAGTACCCTAAGCTGGAAAGCGAGTTCGTGTACGGCGACTACAAGGTGTACGACGTGCGGAA
GATGATCGCCAAGAGCGAGCAGGAAATCGGCAAGGCTACCGCCAAGTACTTCTTCTACAGCAACATCATGAAC
TTTTTCAAGACCGAGATTACCCTGGCCAACGGCGAGATCCGGAAGCGGCCTCTGATCGAGAcAAACGGCGAA
ACCGGGGAGATCGTGTGGGATAAGGGCCGGGATTTTGCCACCGTGCGGAAAGTGCTGAGCATGCCCCAAGTG
AATATCGTGAAAAAGACCGAGGTGCAGACAGGCGGCTTCAGCAAAGAGTCTATCCTGCCCAAGAGGAACAGC
GATAAGCTGATCGCCAGAAAGAAGGACTGGGACCCTAAGAAGTACGGCGCTTCGACAGCCCCACCGTGGCC
TATTCTGTGCTGGTGGTGGCCAAAGTGGAAAAGGGCAAGTCCAAGAAACTGAAGAGTGTGAAAGAGCTGCTG
GGGATCACCATCATGGAAAGAAGCAGCTTCGAGAAGAATCCCATCGACTTTCTGGAAGCCAAGGGCTACAAA
GAAGTGAAAAAGGACCTGATCATCAAGCTGCCTAAGTACTCCCTGTTCGAGCTGGAAAACGGCCGGAAGAGA
ATGCTGGCCTCTGCCGGCGAACTGCAGAAGGGAAACGAACTGGCCCTGCCCTCCAAATATGTGAACTTCCTGT
ACCTGGCCAGCCACTATGAGAAGCTGAAGGGCTCCCCCGAGGATAATGAGCAGAAACAGCTGTTTGTGGAAC
AGCACAAGCACTACCTGGACGAGATCATCGAGCAGATCAGCGAGTTCTCCAAGAGAGTGATCCTGGCCGACG
CTAATCTGGACAAAGTGCTGTCCGCCTACAACAAGCACCGGGATAAGCCCATCAGAGAGCAGGCCGAGAATA
TCATCCACCTGTTTACCCTGACCAATCTGGGAGCCCCTGCCGCCTTCAAGTACTTTGACACCACCATCGACCGGA
AGAGGTACACCAGCACCAAAGAGGTGCTGGACGCCACCCTGATCCACCAGAGCATCACCGGCCTGTACGAGA
CACGGATCGACCTGTCTCAGCTGGGAGGCGACAAGCGTCCTGCTGCTACTAAGAAAGCTGGTCAAGCTAAGA
AAAAGAAAGCTAG

HIV-1 encapsidation construct "p8.91" (encoding HIV-1 Gag-Pol-Tat-Rev)

(SEQ ID NO. 33)

ttgattattgactagttattaatagtaatcaattacgggtcattagttcatagcccatatatggagttccgcgttacataacttacggtaaatggcc
cgcctggctgaccgcccaacgacccccgcccattgacgtcaataatgacgtatgttcccatagtaacgccaatagggactttccattgacgtcaat
gggtggagtatttacggtaaactgcccacttggcagtacatcaagtgtatcatatgccaagtacgccccctattgacgtcaatgacggtaaatggc
ccgcctggcattatgcccagtacatgaccttatgggactttcctacttggcagtacatctacgtattagtcatcgctattaccatggtgatgcggtttt
ggcagtacatcaatgggcgtggatagcggtttgactcacggggatttccaagtctccaccccattgacgtcaatgggagtttgttttggcaccaaa
atcaacgggactttccaaaatgtcgtaacaactccgccccattgacgcaaatgggcggtaggcgtgtacggtgggaggtctatataagcagagct
cgtttagtgaaccgtcagatcgcctggagacgccatccacgctgttttgacctccatagaagacaccgggaccgatccagcctccgcggccggga
acggtgcattggaacgcggattccccgtgccaagagtgacgtaagtaccgcctatagagtctctataggcccaccccccttggcttcttatgcgacgga
tcgatcccgtaataagcttcgaggtccgcggccggccgcgttgacgcgcacggcaagaggcgaggggcggcgactggtgagagatgggtgcga
gagcgtcagtattaagcggggagaattagatcgatgggaaaaaattcggttaaggccagggggaaagaaaaatataaattaaaacatata
gtatgggcaagcaggagctagaacgattcgcagttaatcctggcctgttagaaacatcagaaggctgtagacaaatactgggacagctacaac
catcccttcagacaggatcagaagaacttagatcattatataatacagtagcaaccctctattgtgtgcatcaaaggatagagataaaagacacc
aaggaagctttagacaagatagaggaagagcaaaacaaaagtaagaaaaaagcacagcaagcagcagctgacacaggacacagcaatcag
gtcagccaaaattaccctatagtgcagaacatccaggggcaaatggtacatcaggccatatcacctagaactttaaatgcatgggtaaaagtagt
agaagagaaggcttttcagcccagaagtgatacccatgttttcagcattatcagaaggagccaccccacaagatttaaacaccatgctaaacaca
gtggggggacatcaagcagccatgcaaatgttaaaagagaccatcaatgaggaagctgcagaatgggatagagtgcatccagtgcatgcagg
gcctattgcaccaggccagatgagagaaccaaggggaagtgacatagcaggaactactagtacccttcaggaacaaataggatggatgacaca
taatccacctatcccagtaggagaaatctataaaagatggataatcctgggattaaataaaatagtaagaatgtatagccctaccagcattctgg
acataagacaaggaccaaaggaacccttagagactatgtagaccgattctataaaactctaagagccgagcaagcttcacaagaggtaaaaa
attggatgacagaaaccttgttggtccaaaatgcgaacccagattgtaagactatttttaaaagcattgggaccaggagcgacactagaagaaat
gatgacagcatgtcagggagtggggggacccggccataaagcaagagttttggctgaagcaatgagccaagtaacaaattccagctaccataat
gatacagaaaggcaattttaggaaccaaagaaagactgttaagtgtttcaattgtggcaaagaagggcacatagccaaaaattgcagggcccct
aggaaaaagggctgttggaaatgtggaaaggaaggacaccaaatgaaagattgtactgagagacaggctaattttttagggaagatctggcctt
cccacaagggaaggccagggaattttcttcagagcagaccagagccaacagccccaccagaagagagcttcaggtttggggaagagacaaca
actccctctcagaagcaggagccgatagacaaggaactgtatcctttagcttccctcagatcactctttggcagcgacccctcgtcacaataaga
tagggggggcaattaaaggaagctctattagatacaggagcagatgatacagtattagaagaaatgaatttgccaggaagatggaaaccaaaa
tgatagggggaattggaggttttatcaaagtaagacagtatgatcagatactcatagaaatctgcggacataaagctataggtacagtattagta
ggacctacacctgtcaacataattggaagaaatctgttgactcagattggctgcactttaaattttcccattagtcctattgagactgtaccagtaa
aattaaagccaggaatggatggcccaaaagttaaacaatggccattgacagaagaaaaaataaaagcattagtagaaatttgtacagaaatgg
aaaaggaagggaaaatttcaaaaattgggcctgaaaatccatacaatactccagtatttgccataaagaaaaaagacagtactaaatggagaa
aattagtagatttcagagaacttaataagagaactcaagatttctgggaagttcaattaggaataccacatcctgcagggttaaaacagaaaaa
atcagtaacagtactggatgtgggcgatgcatatttttcagttcccttagataaagacttcaggaagtatactgcatttaccatacctagtataaac
aatgagacaccagggattagatatcagtacaatgtgcttccacagggatggaaaggatcaccagcaatattccagtgcagcatgacaaaaatct
tagagccttttagaaaacaaaatccagacatagttatctatcaatacatggatgatttgtatgtaggatctgacttagaaatagggcagcataga
acaaaaatagaggaactgagacaacatctgttgaggtggggatttaccacaccagacaaaaaacatcagaaagaacctccattcctttggatgg
gttatgaactccatcctgataaatggacagtacagcctatagtgctgccagaaaaggacagctggactgtcaatgacatacagaaattagtggg
aaaattgaattgggcaagtcagatttatgcagggattaaagtaaggcaattatgtaaactccttagaggaaccaaagcactaacagaagtagta
ccactaacagaagaagcagagctagaactggcagaaaacagggagattctaaaagaaccggtacatggagtgtattatgacccatcaaaaga
cttaatagcagaaatacagaagcaggggcaagggccaatggacatatcaaatttatcaagagccatttaaaaatctgaaaacaggaaagtatgc
aagaatgaagggtgcccacactaatgatgtgaaacaattaacagaggcagtacaaaaaatagccacagaaagcatagtaatatggggaaaga
ctcctaaatttaaattacccatacaaaaggaaacatgggaagcatggtggacagagtattggcaagccacctggattcctgagtgggagtttgtc
aatacccctcccttagtgaaattatggtaccagttagagaaagaacccatagtaggagcagaaacttctatgtagatggggcagctaataggg
aaactaaattaggaaaagcaggatatgttactgacagaggaagacaaaaagttgtccccctaacggacacaacaaatcagaagactgagtta
caagcaatttatctagctttgcaggattcgggattagaagtaaacatagtgacagactcacaatatgcattgggaatcattcaagcacaaccaga
taagagtgaatcagagttagtcagtcaaataatagagcagttaataaaaaaggaaaaagtctacctggcatgggtaccagcacacaaaggaat
tggaggaaatgaacaagtagataaattggtcagtgctggaatcaggaaagtactatttttagatggaatagataaggcccaagaagaacatga
gaaatatcacagtaattggagagcaatggctagtgattttaacctaccacctgtagtagcaaaagaaatagtagccagctgtgataaatgtcagc
taaaaggggaagccatgcatggacaagtagactgtagcccaggaatatggcagctagattgtacacatttagaaggaaaagttatcctggtagc
agttcatgtagccagtggatatatagaagcagaagtaattccagcagagacagggcaagaaacagcatacttcctcttaaaattagcaggaaga
tggccagtaaaaacagtacatacagacaatggcagcaattttcaccagtactacagttaaggccgcctgttggtgggcgggatcaagcaggaat
ttggcattccctacaatccccaaagtcaaggagtaatagaatctatgaataaagaattaagaaaattataggacaggtaagagatcaggctga
acatcttaagacagcagtacaaatggcagtattcatccacaattttaaaagaaaaggggggattggggggtacagtgcaggggaaagaatagt

Other sequences

```
agacataatagcaacagacatacaaactaaagaattacaaaaacaaattacaaaaattcaaaattttcgggtttattacagggacagcagaga
tccagtttggaaaggaccagcaaagctcctctgaaaggtgaaggggcagtagtaatacaagataatagtgacataaaagtagtgccaagaag
aaaagcaaagatcatcagggattatggaaaacagatggcaggtgatgattgtgtggcaagtagacaggatgaggattaacacatggaattctg
caacaactgctgtttatccatttcagaattgggtgtcgacatagcagaataggcgttactcgacagaggagagcaagaaatggagcagtagat
cctagactagagccctggaagcatccaggaagtcagcctaaaactgcttgtaccaattgctattgtaaaaagtgttgctttcattgccaagtttgtt
tcatgacaaaagccttaggcatctcctatggcaggaagaagcggagacagcgacgaagagctcatcagaacagtcagactcatcaagcttctct
atcaaagcagtaagtagtacatgtaatgcaacctataatagtagcaatagtagcattagtagtagcaataataatagcaatagttgtgtggtcca
tagtaatcatagaatataggaaaatggccgctgatcttcagacctggaggaggagatatgagggacaattggagaagtgaattatataaatata
aagtagtaaaaattgaaccattaggagtagcacccaccaaggcaaagagaagagtggtcagagagaaaaaagagcagtgggaataggagc
tttgttccttgggttcttgggagcagcaggaagcactatgggcgcagcgtcaatgacgctgacggtacaggccagacaattattgtctggtatagt
gcagcagcagaacaatttgctgagggctattgaggcgcaacagcatctgttgcaactcacagtctggggcatcaagcagctccaggcaagaatc
ctggctgtgaaagatacctaaaggatcaacagctcctggggatttggggttgctctggaaaactcatttgcaccactgctgtgccttggaatgct
agttggagtaataaatctctggaacagatttggaatcacacgacctggatggagtgggacagagaaattaacaattacacaagcttaatacact
ccttaattgaagaatcgcaaaaccagcaagaaaagaatgaacaagaattattggaattagataaatgggcaagtttgtggaattggtttaacat
aacaaattggctgtgtatataaaattattcataatgatagtaggaggcttggtaggtttaagaatagttttgctgtactttctatagtgaatagag
ttaggcagggatattcaccattatcgtttcagacccacctcccaaccccgagggggacccgacaggcccgaaggaatagaagaagaaggtggag
agagagacagagacagatccattcgattagtgaacggatcctggcacttatctgggacgatctgcggagcctgtgcctcttcagctaccaccgct
tgagagacttactcttgattgtaacgaggattgtggaacttctgggacgcaggggtggggaagccctcaaatattggtgaatctcctacaatatt
ggagtcaggagctaaagaatagtgctgttagcttgctcaatgccacagccatagcagtagctgagggggacagatagggttatagaagtagtaca
aggagcttgtagagctattcgccacatacctagaagaataagacagggcttggaaaggattttgctataagctcgaggccgccccggtgaccttc
agacctggcactggaggtggcccggcagaagcgcggcatcgtggatcagtgctgcaccagcatctgctctctctaccaactggagaactactgc
aactaggccaccactaccctgtccaccctctgcaatgaataaaacctttgaaagagcactacaagttgtgtgtacatgcgtgcatgtgcatatg
tggtgcgggggaacatgagtggggctggctggagtggcgatgataagctgtcaaacatgagaattaattcttgaagacgaaagggcctcgtga
tacgcctatttttataggttaatgtcatgataataatggtttcttagtctagaattaattccgtgtattctatagtgtcacctaaatcgtatgtgtatga
tacataaggttatgtattaattgtagccgcgttctaacgacaatatgtacaagcctaattgtgtagcatctggcttactgaagcagaccctatcatct
ctctcgtaaactgccgtcagagtcggtttggttggacgaaccttctgagtttctggtaacgccgtcccgcacccggaaatggtcagcgaaccaatc
agcagggtcatcgctagccagatcctctacgccggacgcatcgtggccggcatcaccggcgccacaggtgcggttgctggcgcctatatcgccga
catcaccgatggggaagatcgggctcgccacttcgggctcatgagcgcttgtttcggcgtgggtatggtggcaggccccgtggccgggggactgt
tgggcgccatctccttgcatgcaccattccttgcggcggcggtgctcaacgcctcaacctactactgggctgcttcctaatgcaggagtcgcataa
gggagagcgtcgaatggtgcactctcagtacaatctgctctgatgccgcatagttaagccagccccgacacccgccaacacccgctgacgcgccc
tgacgggcttgtctgctcccggcatccgcttacagacaagctgtgaccgtctccgggagctgcatgtgtcagaggttttcaccgtcatcaccgaaa
cgcgcgagacgaaagggcctcgtgatacgcctatttttataggttaatgtcatgataataatggtttcttagacgtcaggtggcacttttcggggaa
atgtgcgcggaacccctatttgtttatttttctaaatacattcaaatatgtatccgctcatgagacaataaccctgataaatgcttcaataatattga
aaaaggaagagtatgagtattcaacatttccgtgtcgcccttattcccttttttgcggcattttgccttcctgtttttgctcacccagaaacgctggtg
aaagtaaaagatgctgaagatcagttgggtgcacgagtgggttacatcgaactggatctcaacagcggtaagatccttgagagttttcgccccga
agaacgttttccaatgatgagcacttttaaagttctgctatgtggcgcggtattatcccgtattgacgccgggcaagagcaactcggtcgccgcata
cactattctcagaatgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaacatgggggatcatg
taactcgccttgatcgttgggaaccggagctgaatgaagccataccaaacgacgagcgtgacaccacgatgcctgtagcaatggcaacaacgtt
gcgcaaactattaactggcgaactacttactctagcttcccggcaacaattaatagactggatggaggcggataaagttgcaggaccacttctgc
gctcggcccttccggctggctggtttattgctgataaatctggagccggtgagcgtgggtctcgcggtatcattgcagcactggggccagatggta
agccctcccgtatcgtagttatctacacgacggggagtcaggcaactatggatgaacgaaatagacagatcgctgagataggtgcctcactgatt
aagcattggtaactgtcagaccaagtttactcatatatactttagattgatttaaaacttcatttttaatttaaaaggatctaggtgaagatccttttt
gataatctcatgaccaaaatcccttaacgtgagttttcgttccactgagcgtcagacccgtagaaaagatcaaaggatcttcttgagatcctttttt
tctgcgcgtaatctgctgcttgcaaacaaaaaaaccaccgctaccagcggtggtttgtttgccggatcaagagctaccaactctttttccgaaggt
aactggcttcagcagagcgcagataccaaatactgttcttctagtgtagccgtagttaggccaccacttcaagaactctgtagcaccgcctacata
cctcgctctgctaatcctgttaccagtggctgctgccagtggcgataagtcgtgtcttaccgggttggactcaagacgatagttaccggataaggcg
cagcggtcgggctgaacggggggttcgtgcacacagcccagcttggagcgaacgacctacaccgaactgagatacctacagcgtgagctatga
gaaagcgccacgcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtgatgctcgtcaggggggcggagcctatg
gaaaaacgccagcaacgcggcctttttacggttcctggccttttgctggccttttgctcacatgttctttcctgcgttatcccctgattctgtggataac
cgtattaccgcctttgagtgagctgataccgctcgccgcagccgaacgaccgagcgcagcgagtcagtgagcgaggaagcggaagagcgccca
atacgcaaaccgcctctccccgcgcgttggccgattcattaatgcagctgtggaatgtgtgtcagttagggtgtggaaagtccccaggctccccag
caggcagaagtatgcaaagcatgcatctcaattagtcagcaaccaggtgtggaaagtccccaggctccccagcaggcagaagtatgcaaagca
tgcatctcaattagtcagcaaccatagtcccgcccctaactccgcccatcccgcccctaactccgcccagttccgcccattctccgccccatggctg
actaatttttttatttatgcagaggccgaggccgcctcggcctctgagctattccagaagtagtgaggaggcttttttggaggcctaggcttttgca
aaaagcttggacacaagacaggcttgcgagatatgtttgagaataccactttatcccgcgtcagggagaggcagtgcgtaaaaagacgcggact
catgtgaaatactggttttagtgcgccagatctctataatctcgcgcaacctattttcccctcgaacacttttaagccgtagataaacaggctggg
acacttcacatgagcgaaaaatacatcgtcacctgggacatgttgcagatccatgcacgtaaactcgcaagccgactgatgccttctgaacaatg
gaaaggcattattgccgtaagccgtggcggtctgtaccgggtgcgttactggcgcgtgaactgggtattcgtcatgtcgataccgtttgtatttcca
gctacgatcacgacaaccagcgcgagcttaaagtgctgaaacgcgcagaaggcgatggcgaaggcttcatcgttattgatgacctggtggatac
cggtggtactgcggttgcgattgaaaatgtatccaaaagcgcactttgtccaccatcttcgcaaaaccggttcgtcccgctggtgatgatgactat
gttgttgatatcccaagatacctgattgaacagcgtgggatatggggcgtcgtattcgtcccgccaatctccgtcgctaatctttcaacgcct
ggcactgccgggcgttgttctttttaacttcaggcgggttacaatagtttccagtaagtattctggaggctgcatccatgacacaggcaaacctgag
cgaaaccctgttcaaacccgctttaaacatcctgaaacctcgacgctagtccgccgctttaatcacggcgcacaaccgcctgtgcagtcggccct
tgatggtaaaaccatccctcactggtatcgcatgattaaccgtctgatgtggatctggcgcggcattgacccacgcgaaatcctcgacgtccagc
acgtattgtgatgagcgatgccgaacgtaccgacgatgatttatacgatacggtgattggctaccgtggcggcaactggatttatgagtgggcccc
ggatctttgtgaaggaaccttacttctgtggtgtgacataattggacaaactacctacagagatttaaagctctaaggtaaatataaaattttttaac
ccggatctttgtgaaggaaccttacttctgtggtgtgacataattggacaaactacctacagagatttaaagctctaaggtaaatataaaattttta
```

| Other sequences |
|---|
| agtgtataatgtgttaaactactgattctaattgtttgtgtattttagattccaacctatggaactgatgaatgggagcagtggtggaatgcctttaa<br>tgaggaaaacctgttttgctcagaagaaatgccatctagtgatgatgaggctactgctgactctcaacattctactcctccaaaaaagaagagaa<br>aggtagaagaccccaaggactttccttcagaattgctaagttttttgagtcatgctgtgtttagtaatagaactcttgcttgctttgctattta caeca<br>caaaggaaaaagctgcactgctataccaagaaaattatggaaaaatattctgtaacctttataagtaggcataacagttataatcataacatactg<br>ttttttcttactccacacaggcatagagtgtctgctattaataactatgctcaaaaattgtgtacctttagcttttttaatttgtaaaggggttaataag<br>gaatatttgatgtatagtgccttgactagagatcataatcagccataccacatttgtagaggttttacttgctttaaaaaacctcccacacctccccc<br>tgaacctgaaacataaaatgaatgcaattgttgttgttgggctgcaggaattaattcgagctcgcccgaca |

HIV-1 GAG-CAS9-encoding nucleic acid "KLAP229"

(SEQ ID NO. 34)

```
GCGGCCGCTCTAGAGAGCTTGGCCCATTGCATACGTTGTATCCATATCATAATATGTACATTTATATTGGCTCAT
GTCCAACATTACCGCCATGTTGACATTGATTATTGACTAGTTATTAATAGTAATCAATTACGGGGTCATTAGTTC
ATAGCCCATATATGGAGTTCCGCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAGTACGCCCCCTATTGACG
TCAATGACGGTAAATGGCCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAATGGGCGTGGATAGCGGTT
TGACTCACGGGGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCATAGAA
GACACCGGGACCGATCCAGCCTCCGGTCGACCGATCCTGAGAACTTCAGGGTGAGTTTGGGGACCCTTGATTG
TTCTTTCTTTTTCGCTATTGTAAAATTCATGTTATATGGAGGGGCAAAGTTTTCAGGGTGTTGTTTAGAATGGG
AAGATGTCCCTTGTATCACCATGGACCCTCATGATAATTTTGTTTCTTTCACTTTCTACTCTGTTGACAACCATTG
TCTCCTCTTATTTTCTTTTCATTTTCTTGTAACTTTTTCTGTTAAACTTTTAGCTTGCATTTGTAACGAATTTTTAAATT
CACTTTTGTTTATTTTGTCAGATTGTAAGTACTTTCTCTAATCACTTTTTTTTCAAGGCAATCAGGGTATATTATATT
GTACTTCAGCACAGTTTTAGAGAACAATTGTTATAATTAAATGATAAGGTAGAATATTTCTGCATATAAATTCTG
GCTGGCGTGGAAATATTCTTATTGGTAGAAACAACTACATCCTGGTCATCATCCTGCCTTTCTCTTTATGGTTAC
AATGATATACACTGTTTGAGATGAGGATAAAATACTCTGAGTCCAAACCGGGCCCTCTGCTAACCATGTTCAT
GCCTTCTTCTTTTTCCTACAGCTCCTGGGCAACGTGCTGGTTATTGTGCTGTCTCATCATTTTGGCAAAGAATTCc
tcgagatgggtgcgagagcgtcggtattaagcggggagaattagataaatgggaaaaaattcggttaaggccaggggaaagaaacaatat
aaactaaaacatatagtatgggcaagcagggagctagaacgattcgcagttaatcctggcctttagagacatcagaaggctgtagacaaatac
tgggacagctacaaccatcccttcagacaggatcagaagaacttagatcattatataataacaatagcagtcctctattgtgtgcatcaaaggata
gatgtaaaagacaccaaggaagccttagataagatagaggaagagcaaaacaaaagtaagaaaaaggcacagcaagcagcagctgacaca
ggaaacaacagccagtCAGCCAAAATTACCCTATAGTGCAGAACctccaggggcaaatggtacatcaggccatatcacctagaa
ctttaaatgcatgggtaaaagtagtagaagagaaggctttcagcccagaagtaatacccatgttttcagcattatcagaaggagccaccccacaa
gatttaaataccatgctaaacacagtggggggacatcaagcagccatgcaaatgttaaaagagaccatcaatgaggaagctgcagaatgggat
agattgcatccagtgcatgcagggcctattgcaccaggccagatgagagaaccaaggggaagtgacatagcaggaactactagtacccttcag
gaacaaataggatggatgacacataatccacctatcccagtaggagaaatctataaaagatggataatcctgggattaaataaaatagtaaga
atgtatagccctaccagcattctggacataagacaaggaccaaaggaaccctttagagactatgtagaccgattctataaaactctaagagccg
agcaagcttcacaagaggtaaaaaattggatgacagaaaccttgttggtccaaaatgcgaacccagattgtaagactattttaaaagcattggg
accaggagcgacactagaagaaatgatgacagcatgtcagggagtgggggggacccggccatAAAGCAAGAGTTTTGGCTGAAGCA
ATGAGCcaagtaacaaatccagctaccataatgatacagaaaggcaattttaggaaccaaagaaagactgttaagtgtttcaattgtggcaa
agaagggcacatagccaaaaattgcagggcccctaggaaaaagggctgttggaaatgtggaaaggaaggacaccaaatgaaagattgtactG
AGAGACAGGCTAATTTTTTAGGGAAGATCtggccttcccacaagggaAGGCCAGGGAATTTTCTTCAGAGCAGACCA
gagccaacagccccaccagaagagagcttcaggtttggggaagagacaacaactccctctcagaagcaggagccgatagacaaggaactgta
tcctttagcttccctcagatcactctttggcagcgacccctcgtcacaaCCGGGGACCACGACCCCAGGcAAAGCAAGAGTTTTG
GCTGAAGCAATGAGCaccggtGATTACAAAGACGATGACGATAAGATGGCCCCAAAGAAGAAGCGGAAGGTCG
GTATCCACGGAGTCCCAGCAGCCGACAAGAAGTACAGCATCGGCCTGGACATCGGCACCAACTCTGTGGGCT
GGGCCGTGATCACCGACGAGTACAAGGTGCCCAGCAAGAAATTCAAGGTGCTGGGCAACACCGACCGGCACA
GCATCAAGAAGAACCTGATCGGAGCCCTGCTGTTCGACAGCGGCGAAACAGCCGAGGCCACCCGGCTGAAGA
GAACCGCCAGAAGAAGATACACCAGACGGAAGAACCGGATCTGCTATCTGCAAGAGATCTTCAGCAACGAGA
TGGCCAAGGTGGACGACAGCTTCTTCCACAGACTGGAAGAGTCCTTCCTGGTGGAAGAGGATAAGAAGCACG
AGCGGCACCCCATCTTCGGCAACATCGTGGACGAGGTGGCCTACCACGAGAAGTACCCCACCATCTACCACCT
GAGAAAGAAACTGGTGGACAGCACCGACAAGGCCGACCTGCGGCTGATCTATCTGGCCCTGGCCCACATGAT
CAAGTTCCGGGGCCACTTCCTGATCGAGGGCGACCTGAACCCCGACAACAGCGACGTGGACAAGCTGTTCATC
CAGCTGGTGCAGACCTACAACCAGCTGTTCGAGGAAAACCCCATCAACGCCAGCGGCGTGGACGCCAAGGCC
ATCCTGTCTGCCAGACTGAGCAAGAGCAGACGGCTGGAAAATCTGATCGCCCAGCTGCCCGGCGAGAAGAAG
AATGGCCTGTTCGGCAACCTGATTGCCCTGAGCCTGGGCCTGACCCCCAACTTCAAGAGCAACTTCGACCTGGC
CGAGGATGCCAAACTGCAGCTGAGCAAGGACACCTACGACGACGACCTGGACAACCTGCTGGCCCAGATCGG
CGACCAGTACGCCGACCTGTTTCTGGCCGCCAAGAACCTGTCCGACGCCATCCTGCTGAGCGACATCCTGAGA
GTGAACACCGAGATCACCAAGGCCCCCCTGAGCGCCTCTATGATCAAGAGATACGACGAGCACCACCAGGACC
TGACCCTGCTGAAAGCTCTCGTGCGGCAGCAGCTGCCTGAGAAGTACAAAGAGATTTTCTTCGACCAGAGCAA
GAACGGCTACGCCGGCTACATTGACGGCGGAGCCAGCCAGGAAGAGTTCTACAAGTTCATCAAGCCCATCCTG
GAAAAGATGGACGGCACCGAGGAACTGCTCGTGAAGCTGAACAGAGAGGACCTGCTGCGGAAGCAGCGGAC
CTTCGACAACGGCAGCATCCCCCACCAGATCCACCTGGGAGAGCTGCACGCCATTCTGCGGCGGCAGGAAGAT
TTTTACCCATTCCTGAAGGACAACCGGGAAAAGATCGAGAAGATCCTGACCTTCCGCATCCCCTACTACGTGGG
CCCTCTGGCCAGGGGAAACAGCAGATTCGCCTGGATGACCAGAAAGAGCGAGGAAACCATCACCCCCTGGAA
CTTCGAGGAAGTGGTGGACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCGTGTATAACGAGCTGACC
AAAGTGAAATACGTGACCGAGGGAATGAGAAAGCCCGCCTTCCTGAGCGGCGAGCAGAAAAAGGCCATCGT
GGACCTGCTGTTCAAGACCAACCGGAAAGTGACCGTGAAGCAGCTGAAAGAGGACTACTTCAAGAAAATCGA
GTGCTTCGACTCCGTGGAAATCTCCGGCGTGGAAGATCGGTTCAACGCCTCCCTGGGCACATACCACGATCTG
CTGAAAATTATCAAGGACAAGGACTTCCTGGACAATGAGGAAAACGAGGACATTCTGGAAGATATCGTGCTG
ACCCTGACACTGTTTGAGGACAGAGAGATGATCGAGGAACGGCTGAAAACCTATGCCCACCTGTTCGACGACA
AAGTGATGAAGCAGCTGAAGCGGCGGAGATACACCGGCTGGGGCAGGCTGAGCCGGAAGCTGATCAACGGC
ATCCGGGACAAGCAGTCCGGCAAGACAATCCTGGATTTCCTGAAGTCCGACGGCTTCGCCAACAGAAACTTCA
TGCAGCTGATCCACGACGACAGCCTGACCTTTAAAGAGGACATCCAGAAAGCCCAGGTGTCCGGCCAGGGCG
```

| Other sequences |
|---|
| ATAGCCTGCACGAGCACATTGCCAATCTGGCCGGCAGCCCCGCCATTAAGAAGGGCATCCTGCAGACAGTGAA
GGTGGTGGACGAGCTCGTGAAAGTGATGGGCCGGCACAAGCCCGAGAACATCGTGATCGAAATGGCCAGAG
AGAACCAGACCACCCAGAAGGGACAGAAGAACAGCCGCGAGAGAATGAAGCGGATCGAAGAGGGCATCAA
AGAGCTGGGCAGCCAGATCCTGAAAGAACACCCCGTGGAAAACACCCAGCTGCAGAACGAGAAGCTGTACCT
GTACTACCTGCAGAATGGGCGGGATATGTACGTGGACCAGGAACTGGACATCAACCGGCTGTCCGACTACGA
TGTGGACCATATCGTGCCTCAGAGCTTTCTGAAGGACGACTCCATCGACAACAAGGTGCTGACCAGAAGCGAC
AAGAACCGGGGCAAGAGCGACAACGTGCCCTCCGAAGAGGTCGTGAAGAAGATGAAGAACTACTGGCGGCA
GCTGCTGAACGCCAAGCTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCACAAAGCACGTGGCACA
GATCCTGGACTCCCGGATGAACACTAAGTACGACGAGAATGACAAGCTGATCCGGGAAGTGAAAGTGATCAC
CCTGAAGTCCAAGCTGGTGTCCGATTTCCGGAAGGATTTCCAGTTTTACAAAGTGCGCGAGATCAACAACTACC
ACCACGCCCACGACGCCTACCTGAACGCCGTCGTGGGAACCGCCCTGATCAAAAAGTACCCTAAGCTGGAAAG
CGAGTTCGTGTACGGCGACTACAAGGTGTACGACGTGCGGAAGATGATCGCCAAGAGCGAGCAGGAAATCG
GCAAGGCTACCGCCAAGTACTTCTTCTACAGCAACATCATGAACTTTTTCAAGACCGAGATTACCCTGGCCAAC
GGCGAGATCCGGAAGCGGCCTCTGATCGAGACAAACGGCGAAACCGGGGAGATCGTGTGGGATAAGGGCCG
GGATTTTGCCACCGTGCGGAAAGTGCTGAGCATGCCCCAAGTGAATATCGTGAAAAAGACCGAGGTGCAGAC
AGGCGGCTTCAGCAAAGAGTCTATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTGTGCTGGTGGTGGCCAAAGTGGA
AAAGGGCAAGTCCAAGAAACTGAAGAGTGTGAAAGAGCTGCTGGGGATCACCATCATGGAAAGAAGCAGCT
TCGAGAAGAATCCCATCGACTTTCTGGAAGCCAAGGGCTACAAAGAAGTGAAAAAGGACCTGATCATCAAGCT
GCCTAAGTACTCCCTGTTCGAGCTGGAAAACGGCCGGAAGAGAATGCTGGCCTCTGCCGGCGAACTGCAGAA
GGGAAACGAACTGGCCCTGCCCTCCAAATATGTGAACTTCCTGTACCTGGCCAGCCACTATGAGAAGCTGAAG
GGCTCCCCCGAGGATAATGAGCAGAAACAGCTGTTTGTGGAACAGCACAAGCACTACCTGGACGAGATCATC
GAGCAGATCAGCGAGTTCTCCAAGAGAGTGATCCTGGCCGACGCTAATCTGGACAAAGTGCTGTCCGCTACA
ACAAGCACCGGGATAAGCCCATCAGAGAGCAGGCCGAGAATATCATCCACCTGTTTACCCTGACCAATCTGGG
AGCCCCTGCCGCCTTCAAGTACTTTGACACCACCATCGACCGGAAGAGGTACACCAGCACCAAAGAGGTGCTG
GACGCCACCCTGATCCACCAGAGCATCACCGGCCTGTACGAGACACGGATCGACCTGTCTCAGCTGGGAGGC
GACAAGCGTCCTGCTACTAAGAAAGCTGGTCAAGCTAAGAAAAAGAAAGCTAGAGCTTGATATCCTGCAG
ACGCGTAGGATCCGTCGAGGAATTCACTCctCAGGTGCAGGCTGCCTATCAGAAGGTGGTGGCTGGTGTGGCC
AATGCCCTGGCTCACAAATACCACTGAGATCTTTTTCCCTCTGCCAAAAATTATGGGGACATCATGAAGCCCCTT
GAGCATCTGACTTCTGGCTAATAAAGGAAATTTATTTTCATTGCAATAGTGTGTTGGAATTTTTTGTGTCTCTCA
CTCGGAAGGACATATGGGAGGGCAAATCATTTAAAACATCAGAATGAGTATTTGGTTTAGAGTTTGGCAACAT
ATGCCCATATGCTGGCTGCCATGAACAAAGGTTGGCTATAAAGAGGTCATCAGTATATGAAACAGCCCCCTGC
TGTCCATTCCTTATTCCATAGAAAAGCCTTGACTTGAGGTTAGATTTTTTTATATTTTGTTTTGTGTTATTTTTT
CTTTAACATCCCTAAAATTTTCCTTACATGTTTTACTAGCCAGATTTTTCCTCCTCTCCTGACTACTCCCAGTCATA
GCTGTCCCTCTTCTCTTATGGAGATCCCTCGACGGATCGGCCGCAATTCGTAATCATGTCATAGCTGTTTCCTGT
GTGAAATTGTTATCCGCTCACAATTCCACACAACATACGAGCCGGAAGCATAAAGTGTAAAGCCTGGGGTGCC
TAATGAGTGAGCTAACTCACATTAATTGCGTTGCGCTCACTGCCCGCTTTCCAGTCGGGAAACCTGTCGTGCCA
GCTGCATTAATGAATCGGCCAACGCGCGGGGAGAGGCGGTTTGCGTATTGGGCGCTCTTCCGCTTCCTCGCTC
ACTGACTCGCTGCGCTCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGCCAGGAACCGTAAA
AAGGCCGCGTTGCTGGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTTATCGCCACTGGCAG
CAGCCACTGGTAACAGGATTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCTGACGCTCAGTGGAACGAAAACTC
ACGTTAAGGGATTTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGTGAGGCACCTATC
TCAGCGATCTGTCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAGTAAGTTGGCCGCAGT
GTTATCACTCATGGTTATGGCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTGCTCTTGCCCGGCGTCAATA
CGGGATAATACCGCGCCACATAGCAGAACTTTAAAAGTGCTCATCATTGGAAAACGTTCTTCGGGGCGAAAAC
TCTCAAGGATCTTACCGCTGTTGAGATCCAGTTCGATGTAACCCACTCGTGCACCCAACTGATCTTCAGCATCTT
TTACTTTCACCAGCGTTTCTGGGTGAGCAAAAACAGGAAGGCAAAATGCCGCAAAAAAGGGAATAAGGGCGA
CACGGAAATGTTGAATACTCATACTCTTCCTTTTTCAATATTATTGAAGCATTTATCAGGGTTATTGTCTCATGA
GCGGATACATATTTGAATGTATTTAGAAAAATAAACAAATAGGGGTTCCGCGCACATTTCCCCGAAAAGTGCC
ACCTAAATTGTAAGCGTTAATATTTTGTTAAAATTCGCGTTAAATTTTTGTTAAATCAGCTCATTTTTTAACCAAT
AGGCCGAAATCGGCAAAATCCCTTATAAATCAAAAGAATAGACCGAGATAGGGTTGAGTGTTGTTCCAGTTTG
GAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGAAGGGAAGAAAGC
GAAAGGAGCGGGCGCTAGGGCGCTGGCAAGTGTAGCGGTCACGCTGCGCGTAACCACCACACCCGCCGCGCT
TAATGCGCCGCTACAGGGCGCGTCCCATTCGCCATTCAGGCTGCGCAACTGTTGGGAAGGGCGATCGGTGCG
GGCCTCTTCGCTATTACGCCAGCTGGCGAAAGGGGGATGTGCTGCAAGGCGATTAAGTTGGGTAACGCCAGG
GTTTTCCCAGTCACGACGTTGTAAAACGACGGCCAGTGAGCGCGCGTAATACGACTCACTATAGGGCGAATTG
GAGCTCCACCGCGGTG |

| Sequences | | |
|---|---|---|
| SEQ ID NO. | Type | Description |
| 1 | Nucleic acid | YFPgRNA1f primer |
| 2 | Nucleic acid | YFPgRNA1r primer |
| 3 | Nucleic acid | YFPgRNA2f primer |
| 4 | Nucleic acid | YFPgRNA2r primer |
| 5 | Nucleic acid | hMyd88gRNA1f primer |
| 6 | Nucleic acid | hMyd88gRNA1r primer |
| 7 | Nucleic acid | hMyd88gRNA2f primer |
| 8 | Nucleic acid | hMyd88gRNA2r primer |
| 9 | Nucleic acid | mMyd88gRNA1f primer |
| 10 | Nucleic acid | mMyd88gRNA1r primer |
| 11 | Nucleic acid | mMyd88gRNA2f primer |
| 12 | Nucleic acid | mMyd88gRNA2r primer |
| 13 | Nucleic acid | DDX3gRNA1f primer |
| 14 | Nucleic acid | DDX3gRNA1r primer |
| 15 | Nucleic acid | YFPf primer |
| 16 | Nucleic acid | YFPr primer |
| 17 | Nucleic acid | hMyd88f2 primer |
| 18 | Nucleic acid | hMyd88r1 primer |
| 19 | Nucleic acid | mMyd88f2 primer |
| 20 | Nucleic acid | mMyd88r2 primer |
| 21 | Nucleic acid | Flag-DDX3 primer |
| 22 | Amino acid | GAG-Cas9 fusion protein |
| 23 | Amino acid | VSV-G protein |
| 24 | Amino acid | GAG PRO POL polyprotein |
| 25 | Amino acid | BAEV-G protein |
| 26 | Nucleic acid | encoding Gag-Cas9 fusion protein |
| 27 | Nucleic acid | encoding BAEV-G |
| 28 | Nucleic acid | encoding VSV-G protein |
| 29 | Amino acid | cleavage sequence |
| 30 | Nucleic acid | encoding the cleavage sequence of SEQ ID NO. 29 |
| 31 | Amino acid | Cas9 protein |
| 32 | Nucleic acid | encoding Cas9 protein |
| 33 | Nucleic acid | HIV encapsidation construct (may be termed "p8.91") |
| 34 | Nucleic acid | encoding HIV-1 GAG-CAS9 polypeptide (may be termed "KLAP229") |
| 35 | Nucleic acid | target sequence |
| 36 | Nucleic acid | primer |
| 37 | Nucleic acid | primer |
| 38 | Nucleic acid | target sequence |
| 39 | Nucleic acid | primer |
| 40 | Nucleic acid | primer |

What is claimed is:

1. A retrovirus-derived particle comprising one or more Cas protein(s), wherein the one or more Cas protein(s) is inside of said particle as a cleavable fusion protein comprising:
   (i) a retroviral gag protein,
   (ii) a proteolysis cleavage site, and
   (iii) the one or more Cas protein(s),
   wherein the proteolysis cleavage site is located between the retroviral gag protein and the one or more Cas protein(s),
   wherein the retrovirus-derived particle is substantially devoid of any nucleic acid encoding a viral protein, and
   wherein the one or more Cas protein(s) is complexed with one or more CRISPR-Cas system guide RNA(s).

2. The retrovirus-derived particle of claim 1, wherein the Cas protein is Cas9 or a homolog or a derivative thereof.

3. The retrovirus-derived particle of claim 1, wherein the Cas protein is Cas9.

4. The retrovirus-derived particle of claim 3, wherein the Cas9 is from *Streptococcus pyogenes* (spCas9).

5. The retrovirus-derived particle of claim 1, wherein the Cas protein is present as a cleavable fusion protein comprising a proteolysis cleavage site located between the viral structural protein and the Cas protein.

6. The retrovirus-derived particle of claim 1, which is a lentivirus-derived particle.

7. The retrovirus-derived particle of claim 3, which is a lentivirus-derived particle.

8. The retrovirus-derived particle of claim 1, wherein the retrovirus-derived particle is devoid of any nucleic acid encoding a viral protein.

9. The retrovirus-derived particle of claim 1, wherein the retrovirus-derived particle is substantially devoid of any encoding nucleic acid.

10. The retrovirus-derived particle of claim 1, wherein the CRISPR-Cas guide RNA(s) comprise:
    a first CRISPR-Cas guide RNA that hybridizes with a first target sequence of a target nucleic acid, and
    a second CRISPR-Cas guide RNA that hybridizes with a second target sequence of the target nucleic acid.

11. The retrovirus-derived particle of claim 1, wherein the retrovirus-derived particle is selected from the group consisting of Moloney murine leukemia virus-derived vector particles, Bovine immunodeficiency virus-derived particles, Simian immunodeficiency virus-derived vector particles, Feline immunodeficiency virus-derived vector particles, Human immunodeficiency virus-derived vector particles, Equine infection anemia virus-derived vector particles, Caprine arthritis encephalitis virus-derived vector particles, and Baboon endogenous virus-derived vector particles.

12. The retrovirus-derived particle of claim 11, wherein the retrovirus-derived particle is a Moloney murine leukemia virus-derived vector particle.

13. The retrovirus-derived particle of claim 11, where the retrovirus-derived particle is a Human immunodeficiency virus-derived vector particle.

14. The retrovirus-derived particle of claim 11, where the retrovirus-derived particle is a Baboon endogenous virus-derived vector particle.

15. The retrovirus-derived particle of claim 1, wherein the retrovirus-derived particle further comprises a viral protease.

16. The retrovirus-derived particle of claim 1, wherein the retrovirus-derived particle is devoid of any viral protease.

* * * * *